(12) United States Patent
Abel et al.

(10) Patent No.: US 11,904,083 B2
(45) Date of Patent: Feb. 20, 2024

(54) TREATMENT ASPECTS FOR REDUCING THE CARBON DIOXIDE CONTENT IN THE BLOOD

(71) Applicant: FRESENIUS MEDICAL CARE DEUTSCHLAND GMBH, Bad Homburg (DE)

(72) Inventors: Petra Abel, Friedberg (DE); Jurgen Klewinghaus, Oberursel (DE); Rolf Zander, Mainz (DE)

(73) Assignee: FRESENIUS MEDICAL CARE DEUTSCHLAND GMBH, Bad Homburg (DE)

( * ) Notice: Subject to any disclaimer, the term of this patent is extended or adjusted under 35 U.S.C. 154(b) by 356 days.

(21) Appl. No.: 16/954,217

(22) PCT Filed: Dec. 21, 2018

(86) PCT No.: PCT/EP2018/086750
§ 371 (c)(1),
(2) Date: Jun. 16, 2020

(87) PCT Pub. No.: WO2019/122407
PCT Pub. Date: Jun. 27, 2019

(65) Prior Publication Data
US 2020/0338253 A1 Oct. 29, 2020

(30) Foreign Application Priority Data

Dec. 22, 2017 (DE) ...................... 10 2017 131 192.0

(51) Int. Cl.
| | | |
|---|---|---|
| *A61M 1/36* | (2006.01) | |
| *A61M 1/34* | (2006.01) | |
| *A61M 1/16* | (2006.01) | |

(52) U.S. Cl.
CPC ........ *A61M 1/3627* (2013.01); *A61M 1/1629* (2014.02); *A61M 1/1696* (2013.01);
(Continued)

(58) Field of Classification Search
CPC .............. A61K 2300/00; A61K 31/185; A61K 31/198; A61K 31/495; A61K 45/06;
(Continued)

(56) References Cited

U.S. PATENT DOCUMENTS

| | | |
|---|---|---|
| 4,770,774 A | 9/1988 | Ida et al. |
| 5,041,387 A | 8/1991 | Zander et al. |

(Continued)

FOREIGN PATENT DOCUMENTS

| | | |
|---|---|---|
| DE | 3321200 C2 | 10/1991 |
| DE | 19622184 A1 | 12/1997 |

(Continued)

OTHER PUBLICATIONS

International Search Report and Written Opinion issued in corresponding International Patent Application No. PCT/EP2018/086750 (with English translation of International Search Report) dated Jul. 1, 2019 (14 pages).

*Primary Examiner* — Dirk R Bass
(74) *Attorney, Agent, or Firm* — Kilyk & Bowersox, P.L.L.C.

(57) ABSTRACT

The present disclosure relates to various aspects of a procedure for reducing the carbon dioxide content in blood during the treatment of patients. A first aspect of the present disclosure relates to a buffer solution for use in reducing the carbon dioxide content in the blood when treating a patient suffering from pulmonary insufficiency or the complete failure of lung function, wherein the fluid is in gas exchange with a portion of the patient's blood conducted through an (Continued)

extracorporeal circuit. The first aspect of the present disclosure further relates to an apparatus for the extracorporeal reduction of the carbon dioxide content in the blood using said buffer solution. A second aspect of the present disclosure relates to a system for extracorporeal blood treatment, likewise using said buffer solution and the apparatus, and furthermore to a treatment apparatus for extracorporeal blood treatment comprising the aforementioned system. A third aspect of the present disclosure relates to a functional unit for performing extracorporeal blood treatment, a blood-guiding apparatus for interacting with the functional unit for performing an extracorporeal blood treatment using the aforementioned buffer solution, which comprises a blood treatment element, wherein the blood treatment element is the aforementioned apparatus for the extracorporeal reduction of the carbon dioxide content in the blood. In a fourth aspect, the present disclosure relates to a treatment system comprising the aforementioned apparatus for the extracorporeal reduction of the carbon dioxide content in blood as well as a balancing device. In a fifth aspect, the present disclosure relates to a treatment system comprising the aforementioned apparatus for the extracorporeal reduction of the carbon dioxide content in blood as well as a means for reducing the pressure of the aforementioned buffer solution used in said treatment system.

17 Claims, 14 Drawing Sheets

(52) U.S. Cl.
CPC ......... *A61M 1/3462* (2013.01); *A61M 1/3496* (2013.01); *A61M 1/3679* (2013.01); *A61M 2202/0225* (2013.01); *A61M 2205/02* (2013.01); *A61M 2205/3331* (2013.01)

(58) Field of Classification Search
CPC .............. A61M 1/1629; A61M 1/1696; A61M 1/1698; A61M 1/3462; A61M 1/3496; A61M 1/3627; A61M 1/3679; A61M 2202/0225; A61M 2205/02; A61M 2205/3331; A61P 43/00
See application file for complete search history.

(56) References Cited

U.S. PATENT DOCUMENTS

| | | | |
|---|---|---|---|
| 9,759,229 B2 | 9/2017 | Baumgartner et al. | |
| 10,201,649 B2 | 2/2019 | Haag et al. | |
| 10,265,453 B2 | 4/2019 | Flieg et al. | |
| 2007/0108128 A1* | 5/2007 | Kopperschmidt | A61M 1/3434 210/90 |
| 2008/0093276 A1* | 4/2008 | Roger | A61M 1/28 210/104 |
| 2012/0226258 A1 | 9/2012 | Otto et al. | |
| 2013/0087210 A1* | 4/2013 | Brandl | A61M 1/3624 137/115.01 |
| 2016/0271311 A1 | 9/2016 | Matheis | |

FOREIGN PATENT DOCUMENTS

| | | | | |
|---|---|---|---|---|
| DE | 10034098 A1 | 1/2002 | | |
| EP | 3377141 B1 * | 10/2020 | ............. | A61K 31/00 |
| WO | 90/11787 A1 | 10/1990 | | |
| WO | 2014113740 A1 | 7/2014 | | |
| WO | 2017085291 A1 | 5/2017 | | |

* cited by examiner

TREATMENT ASPECTS FOR REDUCING THE CARBON DIOXIDE CONTENT IN THE BLOOD This application is a National Stage Application of PCT/EP2018/086750, filed Dec. 21, 2018, which claims priority to German Patent Application No. 10 2017 131 192.0, filed Dec. 22, 2017.

TECHNICAL BACKGROUND

The present disclosure relates to various aspects of a procedure for reducing the carbon dioxide content in blood during the treatment of patients. A first aspect of the present disclosure relates to a buffer solution for use in reducing the carbon dioxide content in the blood when treating a patient suffering from pulmonary insufficiency or the complete failure of lung function, wherein the fluid is in gas exchange with a portion of the patient's blood conducted through an extracorporeal circuit. The first aspect of the disclosure further relates to an apparatus for the extracorporeal reduction of the carbon dioxide content in the blood using said buffer solution. A second aspect of the disclosure relates to a system for extracorporeal blood treatment, likewise using said buffer solution and the apparatus, and furthermore to a treatment apparatus for extracorporeal blood treatment comprising the aforementioned system. A third aspect of the disclosure relates to a functional unit for performing an extracorporeal blood treatment, a blood-guiding apparatus for interacting with the functional unit for performing extracorporeal blood treatment using the aforementioned buffer solution, which comprises a blood treatment element, wherein the blood treatment element is the aforementioned apparatus for the extracorporeal reduction of the carbon dioxide content in the blood. In a fourth aspect, the invention relates to a treatment system comprising the aforementioned apparatus for the extracorporeal reduction of the carbon dioxide content in blood as well as a balancing device. In a fifth aspect, the invention relates to a treatment system comprising the aforementioned apparatus for the extracorporeal reduction of the carbon dioxide content in blood as well as a means for reducing the pressure of the aforementioned buffer solution used in said treatment system.

PRIOR ART

The central task of the lungs is the gas exchange of oxygen ($O_2$) and carbon dioxide ($CO_2$). Oxygen is thereby absorbed and carbon dioxide released and, in the normal state, optimum conditions prevail in the lungs for this.

The diffusion of oxygen and carbon dioxide in the lungs occurs over a very large area of 80 to 120 $m^2$ and at a low blood film thickness and sufficiently long enough contact time. In cases in which the lung is not functional such as, for example, during heart surgery, or when the lung is so severely damaged that it is unable to adequately perform its gas exchange function such as, for example, in patients with acute respiratory distress syndrome (ARDS), medical procedures which replace or assist the absent or insufficient gas exchange function are required.

The devices used today to assist or completely replace the gas exchange function of the lungs are membrane oxygenators in which extracorporeally guided blood is separated from the gas phase via a membrane. Oxygen is provided for saturating the blood via said membrane and carbon dioxide is released from the blood into the gas phase. The basic construction and mode of operation of a membrane oxygenator are known from the prior art and are explained in more detail in, for example, the EP 0 465 506 81 patent specification.

The term "extracorporeally guided blood" or the formulation "blood conducted through an extracorporeal circuit" respectively in conjunction with the described prior art and the present disclosure denotes the portion of a patient's blood located in an extracorporeal circuit for the purpose of reducing the carbon dioxide content in order to enable gas exchange with an elimination medium there.

Modern oxygenators use microporous polypropylene hollow fibers (i.e. hollow fibers made of PP, polypropylene) or microporous hollow fibers made of PMP (polymethylpentene) for the purpose of gas exchange between extracorporeal blood and elimination medium. The blood flows past the outside of these hollow fibers in counterflow while an oxygen/air mixture flows through the inside of the fibers. Some of these oxygenators have been further developed to the effect of being optimized with respect to eliminating $CO_2$ from patient blood. For example, EP 2 777 801 A2 describes an apparatus for the at least partial elimination of $CO_2$ from patient blood in which a hollow fiber arrangement having an active fiber length, through which both gas and blood can flow, is provided in the housing, whereby the ratio of active fiber length and minimum blood passage distance through the hollow fiber arrangement is not to exceed a specific value.

Technical Problem

The normal physiological values on the arterial side/mixed venous side when reducing $CO_2$ in the lungs are as follows:
  a) on the mixed venous side
    pH=7.369
    carbon dioxide partial pressure $pCO_2$=46 mmHg
    oxygen partial pressure $pO_2$=40 mmHg
    oxygen saturation $sO_2$=73%
  b) on the arterial side:
    pH=7.4
    carbon dioxide partial pressure $pCO_2$=40 mmHg
    oxygen partial pressure $pO_2$=90 mmHg
    oxygen saturation $sO_2$=96%

After $O_2$ uptake of 250 ml/min, the $pCO_2$ has thus decreased from 46 mmHg to 40 mmHg and the $pO_2$ increased from 40 mmHg to 90 mmHg. In so doing, thus at a pressure difference of $\Delta pCO_2$=6 mmHg, 212 ml of $CO_2$ is removed.

The affinity of the elimination medium used on the elimination side for the uptake of $CO_2$ is crucial to the $CO_2$ diffusion from the blood to the elimination side. The higher the affinity on the elimination side compared to the blood, the more successful the diffusion. The prevailing storage capacity is crucial to the elimination side convection. The higher the capacity on the elimination side, the lower the flow necessary there for the $CO_2$ removal.

The gases (air or mixtures of air and oxygen, nitrogen or noble gases) typically used as the elimination medium in membrane oxygenators have a fairly low affinity on the elimination side for a performance comparable to that of the lungs in $CO_2$ diffusion from the blood to the elimination side. Moreover, the storage capacity is too low to maintain the convection on the elimination side and must be offset by a high flow (high gas flow rate).

Lung physiology compensates for all of this with an extremely large surface area of 80-120 $m^2$ as well as an optimal geometry to the gas exchange surfaces in the form of spherical alveoli having a diameter of 50 to 250 μm.

The disadvantage of using membrane oxygenators as known from the prior art in eliminating carbon dioxide from blood is that the devices are only imperfectly imitating the human lungs. The blood layer is considerably thicker in membrane oxygenators and there is only a diffusion surface of approximately 2 to 10 $m^2$ compared to the very large surface area of up to 120 $m^2$ in the lungs.

Accordingly, there has been a need for a means by which better $CO_2$ diffusion and convection and thus more effective $CO_2$ reduction can be achieved in patients suffering from pulmonary insufficiency or the complete failure of lung function.

SOLUTION TO THE TASK

Figure 1:
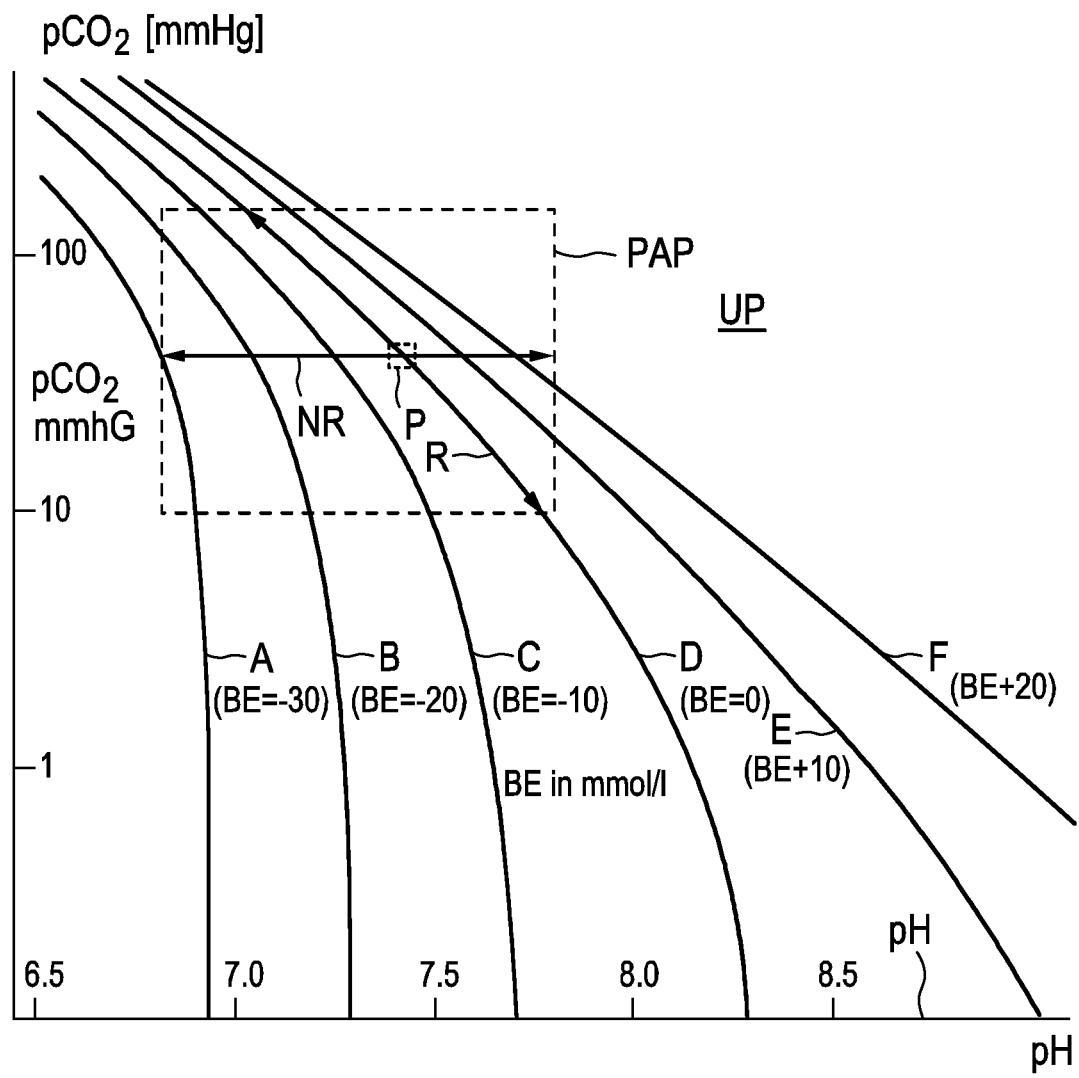
FIG. 1 shows the dependency of the plasma pH value on the respective respiratory load R, ($CO_2$ load) of the blood (cHb=159 g/l, BE=0 mmol).

It has become apparent that considerable advantages are associated with replacing the gases typically used as elimination medium in membrane oxygenators with a fluid having particularly suitable properties for this purpose.

Therefore, the present disclosure proposes the use of a buffer solution for reducing the carbon dioxide content in blood during the treatment of a patient suffering from pulmonary insufficiency or the complete failure of lung function, whereby the buffer solution is an aqueous solution in gas exchange with the blood of the patient conducted in an extracorporeal circuit and contains a buffer A and a buffer B, wherein buffer A consists of at least one buffer substance having a pK value of 7.9±0.2 at 37° C., and buffer B consists of at least one buffer substance having a pK value of 6.9±0.2 at 37° C., and wherein the solution has a post-titration pH value in the range of 8.25 to 8.35 at a carbon dioxide partial pressure of $pCO_2$=0.2 mmHg±0.2.

It has namely become apparent that the desired high affinity for the uptake of $CO_2$ and the capacity required on the elimination side for the $CO_2$ removal can best be provided by a fluid which corresponds to the greatest extent possible to the electrolytic buffer properties of the blood.

The DE 33 212 00 C2 patent specification describes the use of a synthetic fluid as a blood substitute or as a solution for organ preservation, whereby said solution largely corresponds to the electrolytic buffer properties of blood. This is achieved by the solution comprising at least one buffer having a pK value of approximately 7.9 and one buffer having a pK value of approximately 6.9. The known prior art buffer solutions were at that time developed so as to simulate the behavior of natural blood as optimally as possible in terms of the ratio of the pH value and the carbon dioxide partial pressure ($pCO_2$) of the blood. The present disclosure, it can now be shown for the first time that these buffer solutions can also be advantageously used in a completely different context.

In particular, it has been shown that the herein disclosed buffer solution can be used with great advantage to reduce the carbon dioxide content in blood when treating a patient suffering from pulmonary insufficiency or the complete failure of lung function when the buffer solution is in gas exchange with the blood of a patient conducted through an extracorporeal circuit. The reason for this is it being apparent that the herein disclosed used buffer solution has a 6-fold higher affinity for the uptake of $CO_2$ compared to the gases usually used as elimination medium and an 11-fold higher affinity in this regard to water.

The new realization which forms the basis of the present disclosure consists particularly of the fact that the herein disclosed used buffer solution not only affords a very high $CO_2$ affinity (ml/l/mmHg) but also extremely high transport capacity (ml/l) for $CO_2$. The $CO_2$ transport capacity of the herein disclosed used buffer solution can even exceed the transport capacity of natural blood.

For example, at a predetermined pH of 7.4 and a carbon dioxide partial pressure ($pCO_2$) of 40 mmHg, the buffer solution can transport 18.7% more $CO_2$ than natural blood. At a hematocrit of 45%, the bicarbonate concentration is namely 20 mmol/l, consisting of 24 mmol/l bicarbonate in the plasma and 15 mmol/l bicarbonate in the erythrocytes. If the free carbonic acid concentration of 1.2 mmol/l is included, this results in a $CO_2$ transport of 475 ml/l in natural blood. On the other hand, 564 ml/l can be achieved in the case of the herein disclosed buffer solution.

According to the disclosure, buffer A consists of at least one buffer substance having a pK value of 7.9±0.2 at a temperature of 37° C. and buffer B consists of at least one buffer substance and a pK value of 6.9±0.2 at a temperature of 37° C. The solution is adjusted to a pH in the range of 8.25 to 8.35 at a carbon dioxide partial pressure of $pCO_2$=0.2 mmHg±0.2 by titration. In one particular embodiment, the pH value at a carbon dioxide partial pressure of $pCO_2$=0.2 mmHg±0.2 is adjusted to the value of 8.285±0.02 by titration. In one very specific embodiment, the pH value is adjusted to the value of 8.285.

The present disclosure also encompasses variants in which the buffer combination is obtained by two components being produced from a single buffer substance—e.g. by chemical reaction—these exhibiting pK values according to the disclosure after solution in water.

The present disclosure furthermore also encompasses multi-component systems in which the buffer solution consists of more than two buffer substances. One example of an embodiment for a multi-component system containing three components comprises an additional third buffer substance, its pK value being between the pK values of the two other buffer substances.

In certain embodiments of the present disclosure, the buffer solution can also contain at least one buffer C and one buffer D in addition to buffer A and buffer B, whereby buffer C and buffer D each consist of at least one buffer substance, wherein their pK values are substantially equidistantly disposed between the pK values of 6.9±0.2 and 7.9±0.2 at 37° C. In these embodiments of the present disclosure as well, the finished buffer solution has a post-titration pH value in the range of 8.25 to 8.35 at a carbon dioxide partial pressure of $pCO_2$=0.2 mmHg±0.2. In one specific embodiment, the pH value at a carbon dioxide partial pressure of $pCO_2$=0.2 mm Hg±0.2 is adjusted to the value of 8.285±0.02 by titration. In one very specific embodiment, the pH value is adjusted to the value of 8.285.

The buffer solution preferably has a particularly high effective carbon dioxide affinity. Particularly preferential is for the effective carbon dioxide affinity to be greater than that of natural blood. In certain embodiments, the effective carbon dioxide affinity is at least 10 ml/l/mmHg, preferably more than 15 ml/l/mmHg, at a carbon dioxide partial pressure of 40 mmHg. In alternative embodiments, the effective carbon dioxide affinity is at least 20 ml/l/mmHg, preferably ≥25 ml/l/mmHg, even more preferably ≥30 ml/l/mmHg, at a $pCO_2$ of 10 mmHg. Preferential among these are the embodiments in which the $pCO_2$ of the buffer solution is in the range of 0 to 10 mm Hg.

The buffer solution preferably has a particularly high carbon dioxide transport capacity. Particularly preferential is for the effective carbon dioxide transport capacity to be greater than that of natural blood. One advantage of the herein disclosed used buffer solution over natural blood consists in particular of the buffer solution not containing erythrocytes whereas blood consists of $CO_2$-rich plasma and low-$CO_2$ erythrocytes at the given $pCO_2$. At a $pCO_2$ of 40 mmHg, the carbon dioxide transport capacity in certain embodiments of the herein disclosed buffer solution amounts to at least 500 ml/l or more and in alternative embodiments, the carbon dioxide transport capacity at a $pCO_2$ of 10 mmHg amounts to at least 250 ml/l or more.

In certain embodiments, the $pCO_2$ of the herein disclosed used buffer solution is at most 0.2 mmHg±0.2 and thus in the range of the fractional concentration in the inspiration air.

A substantial feature of the present disclosure is that of the buffer substances used in the buffer solution having suitable pK values. In particular, the buffer solution needs to have a buffer A and a buffer B, wherein buffer A consists of at least one buffer substance having a pK value of 7.9±0.2 at 37° C. and buffer B consists of at least one buffer substance having a pK value of 6.9±0.2 at 37° C.

All buffer substances having the abovementioned properties are in principle suitable for the purpose of realizing the present disclosure. For example, the buffer substances herein disclosed used in the buffer solution can be selected from among the following: BICINE (N, N-bis-(2-hydroxyethyl) glycine), BES (N, N-bis-(2-hydroxyethyl)-2-aminoethanesulfonic acid), TAPS (N-tris-(hydroxymethyl)methyl-3-aminopropanesulfonic acid), TRICIN (N-tris-(hydroxymethyl) methylglycine), TRIS (tris-(hydroxymethyl) aminomethane), Imidazole (1,3-Diazole), HEPES (2-(4-(2-hydroxyethyl)-1-piperazine)ethanesulfonic acid) and sodium phosphate ($Na_2HPO_4$), without the disclosure being limited in any form to these specific buffer substances.

In one particular embodiment of the present disclosure, the buffer solution used contains the following components:

| Buffer A | Tris | 36.0 mmol/l |
| --- | --- | --- |
| Buffer B | Na$_2$HPO$_4$ | 34 mmol/l |
| Titer | HCl | 12.0 mmol/l |

The herein disclosed buffer solution described in the present application can be a component of an apparatus for the extracorporeal reduction of carbon dioxide content in blood as an elimination medium. Accordingly, the present disclosure also comprises an apparatus which has a first delimited region for receiving extracorporeal blood and a second delimited region for receiving the herein disclosed buffer solution, wherein the first and second region adjoining each other in a contact zone are only separated by a membrane, via which gas exchange can occur between the blood and the buffer solution.

In a specifically designed embodiment of the herein disclosed apparatus, the first delimited region for receiving the extracorporeal blood has an inlet port and an outlet port for the blood and is configured such that the blood can flow through the region from the inlet port to the outlet port in a first flow direction. The second delimited region for receiving the buffer solution has in this embodiment an inlet port and an outlet port for the buffer solution and is configured such that the buffer solution can flow through the region from the inlet port to the outlet port in a second flow direction.

In certain embodiments of the present disclosure, the flow directions in the individual regions are oriented such that the first flow direction of the first region and the second flow direction of the second region run opposite to each other.

The herein disclosed apparatus has an exchange surface via which gas exchange can occur through the membrane in the contact zone. In certain embodiments, the exchange surface extends over at least 0.3 m$^2$, in particular at least 0.6 m$^2$, particularly at least 1 m$^2$, preferably at least 2 m$^2$. In certain embodiments, the exchange surface extends over at most 5 m$^2$, preferably at most 3 m$^2$.

Preferably, the exchange surface is a gas-permeable membrane as is known from the prior art. As described in EP 2 777 801 A1, such a membrane can consist for example of microporous (e.g. PP=polypropylene) or diffusive hollow fibers (e.g. PMP=polymethylpentene). These hollow fibers can be arranged in parallel aligned mats and the hollow fiber arrangement can either have a cylindrical or an approximate cuboid shape.

In a further embodiment, the herein disclosed apparatus is characterized in that the membrane, via which the gas exchange occurs, comprises polysulfone and optionally polyvinylpyrrolidone. In the context of the present disclosure, the term "polysulfone" is to be understood as a generic term for polymers characterized by sulfonic groups in the polymer chain. Polysulfone (PSU) and polyether sulfone (PES) are known polysulfone agents.

In a further embodiment, the herein disclosed apparatus is characterized in that the membrane which separates the first delimited region and the second delimited region from each other is formed from a plurality of hollow fibers. The term "hollow fiber" is to be understood as a hollow fiber consisting of a membrane material. Corresponding hollow fibers, in particular hollow fibers comprising polysulphone and polyvinyl-pyrrolidone, are known to the person skilled in the art in the field of therapeutic extracorporeal blood treatment. The hollow fibers are arranged such that a membrane (also referred to as "hollow fiber membrane") is formed from the hollow fibers separating a first and a second region from one another. In this regard, one skilled in the art is familiar with filters based on such hollow fiber membranes (also referred to as "hollow fiber membrane filters"). The end regions of such hollow fiber membranes in a hollow fiber membrane filter are fixed in the hollow fiber membrane filter by means of a potting compound. The hollow fiber membranes are thereby open at the end such that the interior of the hollow fibers and the intermediate space between the hollow fibers in the hollow fiber membrane filter form a first and a second delimited region, wherein blood can access the first delimited region and the herein disclosed buffer solution can access the second delimited region.

In particular, "apparatus" in the context of the present disclosure is understood as a blood treatment apparatus which serves as a gas exchange apparatus for the extracorporeal blood treatment, as provided in particular for the gas exchange of CO$_2$, in order to effect the reduction of the carbon dioxide content in extracorporeally treated blood.

For removing CO$_2$ from blood, one embodiment of the present disclosure utilizes a membrane based on silicone-coated hollow fibers which comprises polysulphone and optionally polyvinylpyrrolidone. Such a hollow fiber membrane is described in DE10034098. The advantage of using such a hollow fiber membrane for the extracorporeal treatment of blood for reducing the carbon dioxide content is to be seen in that silicone has a higher CO$_2$ permeability compared to alternative polymers which can be used to form hollow fiber membranes. The inner and/or the outer surface of the hollow fibers can thereby be coated with silicone.

The flow rate at which the blood flows through the first delimited region ideally amounts to at most 20% by volume, particularly ideally at most 15% by volume, of the cardiac output of the patient for whom the carbon dioxide content in the blood is to be reduced extracorporeally with the apparatus. In certain embodiments, the flow rate at which the blood flows through the first delimited region amounts at most to 10% by volume of the cardiac output.

Based on the calculation basis for a patient with a body weight of 75 kg, the flow rate at which the blood flows through the first delimited region is in certain embodiments at least 100 ml/min, preferably at least 200 ml/min, or at least 500 ml/min, or preferably at least 600 ml/min, or particularly preferably at least 750 ml/min. Based on the calculation basis for a patient with a body weight of 7.5 kg, the flow rate is in certain embodiments at least 50 ml/min, preferably 60 ml/min, particularly preferably 750 ml/min.

Based on the calculation basis for a patient with a body weight of 75 kg, the flow rate at which the blood flows through the first delimited region is in certain embodiments at most 1000 ml/min, or at most 800 ml/min, preferably at most 700 ml/min, particularly preferably at most 600 ml/min. Based on the calculation basis for a patient with a body weight of 7.5 kg, the flow rate at which the blood flows through the first delimited region is in certain embodiments at most 80 ml/min, preferably at most 75 ml/min, particularly preferably at most 60 ml/min.

The flow rate at which the buffer solution flows through the second delimited region is, depending on its composition, only 10 to 100% by volume or only 50 to 100% by volume of the flow rate at which the blood flows through the first delimited region.

In certain embodiments, the apparatus has a device for enriching the extracorporeally guided blood with oxygen. Oxygenation of the blood can thereby ensue simultaneously with the CO$_2$ reduction, whereby the Christiansen-Douglas-Haldane effect can be utilized. Oxygenated blood then enables a better release of $CO_2$. The $SO_2$ can thus be increased in 10% of the exchanged blood, for example from 50% to 100%.

Preferably, the apparatus has a device for regenerating the buffer solution via which carbon dioxide taken from the blood can be removed again from the buffer solution. Particularly preferably, this ensues via the quantitative supply of optionally concentrated acid, whereby 98% of the carbon dioxide stored in the buffer solution in the form of bicarbonate is increasingly converted into carbon dioxide and can outgas in this form. Preferably, the device for regenerating the buffer solution consists of a means for supplying an acid to the buffer solution to be regenerated.

In an alternative embodiment, the buffer solution can also be regenerated in a further apparatus. The further apparatus is a regeneration apparatus. It can be composed of a first delimited region and a second delimited region, wherein the two delimited regions are only separated from one another by a membrane or a plurality of membranes, e.g. hollow fiber membranes, which form the membrane for delimiting the first delimited region and the second delimited region. The membrane is a membrane which brings the first delimited region and the second delimited region into a gas exchange relationship. The membrane(s), or hollow fiber membrane(s) respectively, of the regeneration apparatus can be designed as per the membrane in the apparatus for reducing the carbon dioxide content in blood according to one of the embodiments described herein. The regeneration apparatus is operated with a buffer solution which flows through the first delimited region, whereby a regeneration fluid or a regeneration gas flows through the second delimited region. The apparatus for reducing the carbon dioxide content in blood and the regeneration apparatus can be connected in series; i.e. the buffer solution first flows through the second delimited region of the apparatus for reducing the carbon dioxide content in blood and then through the first delimited region of the regeneration apparatus. The apparatus for reducing the carbon dioxide content in blood and the regeneration apparatus can also be configured together in one apparatus, wherein the apparatus for reducing the carbon dioxide content in blood then exhibits the features of the regeneration apparatus.

For original disclosure purposes, it is pointed out that all the features described in the present description, the drawings, the forms of use and embodiments which are able to be deduced by one skilled in the art, even if only having been described in conjunction with specific other features, can be combined both individually and in any combination with other features or feature groups disclosed herein, provided doing so has not been explicitly excluded or technical circumstances make such combinations impossible or pointless. The comprehensive explicit representation of all conceivable feature combinations is only omitted here for the sake of brevity and readability of the description.

Furthermore pointed out is that it is obvious to the person skilled in the art that the following exemplary embodiments and attached figures serve merely to indicate exemplary embodiments of the present disclosure.

FIGURES

Figure 2:
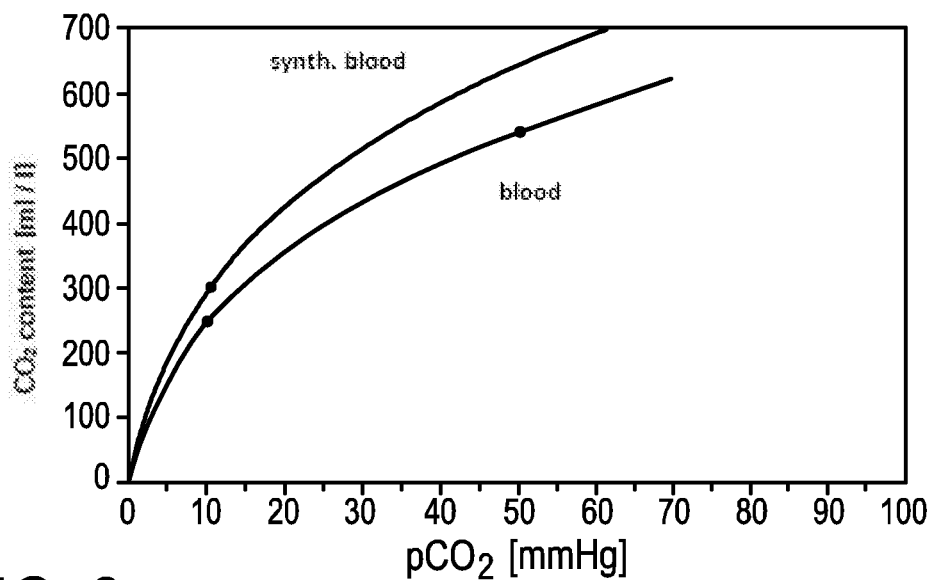
FIG. 2 shows a comparison between the $CO_2$ affinity and transport capacity of the herein disclosed buffer solution (synth. blood) and the $CO_2$ affinity and transport capacity of natural blood (blood) as a function of the respective carbon dioxide partial pressure.
Figure 3:
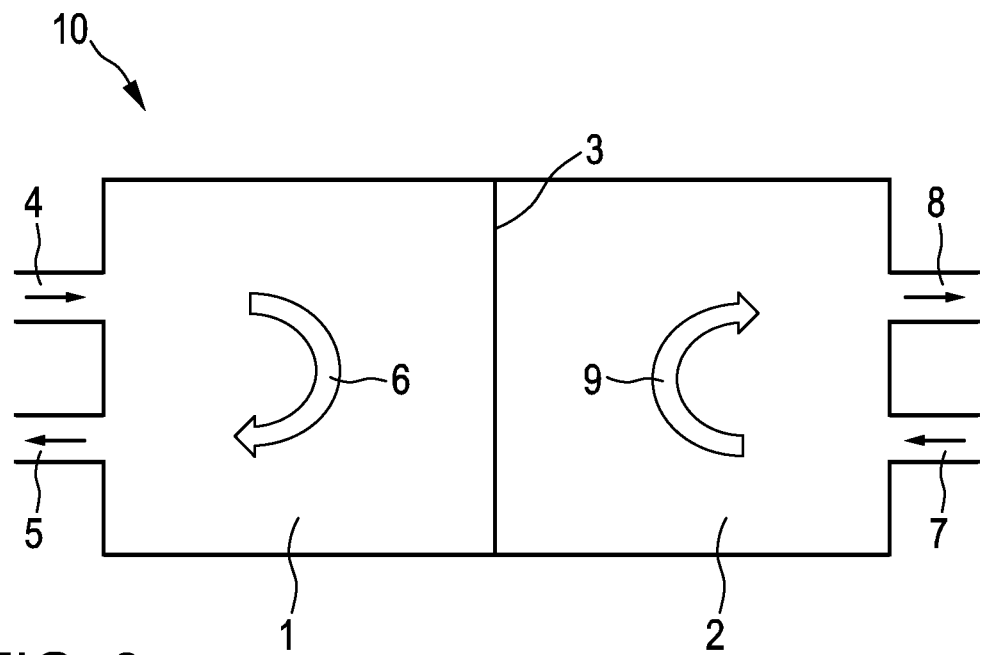
FIG. 3 schematically shows the basic structure of a specific embodiment of the herein disclosed apparatus for the extracorporeal reduction of carbon dioxide content in blood.

FIG. 1 shows the dependency of the plasma pH value on the respective respiratory load R, ($CO_2$ load) of the blood (cHb=159 g/l, BE=0 mmol), FIG. 2 shows a comparison between the $CO_2$ affinity and transport capacity of the herein disclosed buffer solution (synth. blood) and the $CO_2$ affinity and transport capacity of natural blood (blood) as a function of the respective carbon dioxide partial pressure, and FIG. 3 schematically shows the basic structure of a specific embodiment of the herein disclosed apparatus for the extracorporeal reduction of carbon dioxide content in blood.

To illustrate the present disclosure, FIG. 1 depicts the dependency of the plasma pH value on the respective respiratory load R, ($CO_2$ load) of the blood (cHb=159 g/l, BE=0 mmol).

The parameters of curves A to F are the different concentrations of the "non-volatile bases" present in the blood, substantially the "PP fraction" consisting of protein and phosphate which remains due to the non-respiratory load NR (usually referred to as BE). This PP fraction almost exclusively determines the buffering properties of the blood since it necessarily generates the bicarbonate fraction from the respectively present $CO_2$ concentration. This is particularly important to note because the bicarbonate is predominantly in the plasma, the PP fraction predominantly in the erythrocytes (also see DE 31 13 797 C2).

The resulting bicarbonate in turn considerably increases the buffering effect: At a $pCO_2$ value of 40 mmHg, the blood contains 20±0.2 mmol/l bicarbonate. This results in a pH value of 7.4. The respiratory buffer capacity thereby amounts to 25±0.2 mmol/l/pH, the non-respiratory buffer capacity 65±0.2 mmol/l/pH. As a result, 40% of the non-respiratory buffer capacity is represented by the PP fraction and 60% by the bicarbonate fraction.

The buffering properties of human blood depend on the pH value, the $CO_2$ partial pressure and the type of electrolyte supplied. The UP zone in the figure is the non-physiological, the PAP zone the pathophysiological, the P zone the physiological range of the variable pH-$pCO_2$; the dependencies of the buffering properties on the hemoglobin concentration or the hematocrit are thereby not taken into account.

Furthermore, it can be seen from FIG. 1 that with dwindling $pCO_2$, thus when only non-volatile bases (the PP fraction) remain in the blood, curve D, which also runs in physiological range P, intersects the abscissa at pH=8.285. The synthetic blood as herein disclosed used as a buffer solution therefore must exhibit this point of intersection. The intersection point can be regulated by suitable titration with NaOH or HCl.

FIG. 2 depicts a comparison between the $CO_2$ affinity and transport capacity of the herein disclosed buffer solution (synth. blood) and the $CO_2$ affinity and transport capacity of natural blood (blood) as a function of the respective $CO_2$ partial pressure. Hence, at a given $CO_2$ partial pressure, the herein disclosed buffer solution has a consistently higher $CO_2$ affinity and transport capacity than natural blood.

FIG. 3 is a highly schematic depiction of the basic structure of an herein disclosed apparatus for the extracorporeal reduction of carbon dioxide content in blood. Seen in the depiction is the first delimited region 1 for receiving extracorporeal blood and the second delimited region 2 for receiving the herein disclosed buffer solution. The first and the second region adjoining each other in a contact zone are only separated by a membrane 3 via which gas exchange can occur between the blood and the buffer solution.

The first delimited region 1 has a blood inlet port 4 and outlet port 5 for receiving the extracorporeal blood and is designed such that the blood can flow through the region from the inlet port 4 to the outlet port 5 in a first flow direction 6. The second delimited region 2 has a buffer solution inlet port 7 and outlet port 8 for receiving the buffer solution and is designed such that the buffer solution can flow through the region from the inlet port 7 to the outlet port 8 in a second flow direction 9. The first flow direction of the first region and the second flow direction of the second region are thereby oriented so as to run opposite to each other.

EMBODIMENTS

A. Various Embodiments of the Herein Disclosed Buffer Solution

1. Two-Component Buffer Systems

One embodiment of the buffer solution used according to the present disclosure is produced in the following manner:

| Buffer A | TRIS | 36.0 mmol/l |
|---|---|---|
| Buffer B | $Na_2HPO_4$ | 34.0 mmol/l | are weighed and titrated with HCl as the titer (12.0 mmol/l) in the absence of $CO_2$ to a pH value of 8.285.

2. Multi-Component Systems

Should the buffer solution consist of more than two components, the pK values of the two further buffer substances are, according to the present disclosure, equidistantly disposed between the pK values of $6.9 \pm 0.2$ and $7.9 \pm 0.2$.

One embodiment for a multi-component system containing three components comprises the following components:

| Buffer A | TRIS (pK = 7.9) | 23.5 mmol/l |
|---|---|---|
| Buffer B | HEPES (pK = 7.4) | 19.5 mmol/l |
| Buffer C | Phosphate (pK = 6.9) | 17.0 mmol/l |

In this variant of the present disclosure, the pK value of the additional third buffer substance lies in the middle between the pK values of the two other buffer substances.

Particularly favorable substance combinations can thus be selected for the respective purpose. The substance combination can thereby also be attained from a single substance being formed from multiple components—e.g. by chemical reaction—which, after solution in water, exhibit pK values as per the present disclosure.

B. Use of the Herein Disclosed Buffer Solution

Blood with a hemoglobin concentration of cHb=159 g/l, an oxygen partial pressure of $pO_2$=25 mmHg and an oxygen saturation of $sO_2$=50% is treated with a buffer solution according to the present disclosure in the membrane oxygenator.

With simultaneous oxygenation during $CO_2$ reduction, the Christiansen-Douglas-Haldane effect is partially utilized by adding oxygen to the extracorporeally guided blood. The $SO_2$ is thereby increased from 50% to 100% in 10% of the exchanged blood. The buffer solution used comprises the following components:

| Buffer A | TRIS | 36.0 mmol/l |
|---|---|---|
| Buffer B | Na2HPO4 | 34.0 mmol/l |
| Titer | HCl | 12.0 mmol/l |

Example 1

The partial pressure $pCO_2$ of venous blood to be treated is reduced from 50 mmHg to 10 mmHg in a counterflow at a flow rate of 1:1, and 300 ml/l $CO_2$ is thereby removed (see FIG. 2: blood). The buffer solution has taken up the same amount of $CO_2$ and its $CO_2$ partial pressure risen from 0 mmHg to 10.5 mmHg (see FIG. 2: synth. blood). A blood flow rate of 707 ml/min and an HZV of 14% is required.

Example 2

The partial pressure $pCO_2$ of venous blood to be treated is reduced from 50 mmHg to 10 mmHg with simultaneous oxygenation of $sO_2$ from 50% to 100% and in a counterflow at a flow rate of 1:1, and 321 ml/l $CO_2$ is thereby removed. The buffer solution has thereby taken up the same amount of $CO_2$ and its $CO_2$ partial pressure risen from 0 mmHg to 16 mmHg. A blood flow rate of 660 ml/min and an HZV of 13.2% is required.

Example 3

The partial pressure $pCO_2$ of venous blood to be treated is reduced from 55 mmHg (pulmonary dysfunction) to 10 mmHg with simultaneous oxygenation of $sO_2$ from 50% to 100% and in a counterflow at a flow rate of 1:1, and 342 ml/l $CO_2$ is thereby removed. The buffer solution has taken up the same amount of $CO_2$ and its $CO_2$ partial pressure risen from 0 mmHg to 18 mmHg. A blood flow rate of 620 ml/min and an HZV of 12.4% is required.

Example 4

The partial pressure $pCO_2$ of venous blood to be treated is reduced from 70 mmHg (hypercapnia) to 10 mmHg with simultaneous oxygenation of $sO_2$ from 50% to 100% and in a counterflow at a flow rate of 1:1, and 403 ml/l $CO_2$ is thereby removed. The buffer solution has taken up the same amount of $CO_2$ and its $CO_2$ partial pressure risen from 0 mmHg to 25 mmHg. A blood flow rate of 526 ml/min and an HZV of 10.5% is required.

LIST OF REFERENCE NUMERALS FOR FIGS. 1 TO 3

1 first delimited region
2 second delimited region
3 membrane
4 inlet port for the blood
5 outlet port for the blood
6 first flow direction
7 inlet port for the buffer solution
8 outlet port for the buffer solution
9 second flow direction
10 apparatus for the extracorporeal reduction of the carbon dioxide content in blood In a first aspect, the subject of the present disclosure is characterized by the features of the following forms of use 1 to 6 and embodiments 7 to 19:

Form of Use 1

The use of a buffer solution for reducing the carbon dioxide content in blood during the treatment of a patient suffering from pulmonary insufficiency or the complete failure of lung function, wherein the buffer solution is an aqueous solution in gas exchange with the blood of the patient conducted in an extracorporeal circuit and contains a buffer A and a buffer B, wherein buffer A consists of at least one buffer substance having a pK value of $7.9 \pm 0.2$ at 37° C., and buffer B consists of at least one buffer substance having a pK value of 6.9±0.2 at 37° C., and wherein the solution has a post-titration pH value in the range of 8.25 to 8.35 at a carbon dioxide partial pressure of pCO2=0.2 mmHg±0.2.

Form of Use 2

The use as described herein, characterized in that the buffer solution additionally contains at least one buffer C and/or one buffer D in addition to buffer A and buffer B, wherein buffer C and buffer D each consist of at least one buffer substance, the pK values of the buffer substances of buffer C and buffer D are substantially equidistantly disposed between the pK values of 6.9±0.2 and 7.9±0.2 at 37° C., wherein the pK values of the buffer substances of buffer C at a ±0.1 tolerance are at the same distance from the lower threshold value as the pK values of the buffer substances of buffer D are to the higher pK threshold value, and the solution has a post-titration pH value in the range of 8.25 to 8.35 at a carbon dioxide partial pressure of pCO2=0.2 mmHg±0.2.

Form of Use 3

The use as described herein, characterized in that the buffer solution has an effective carbon dioxide affinity of ≥10 ml/l/mmHg, preferably ≥15 ml/l/mmHg, at a $pCO_2$ of 40 mmHg and an effective carbon dioxide affinity of ≥20 ml/l/mmHg, preferably ≥25 ml/l/mmHg, even more preferably 30 ml/l/mmHg, at a $pCO_2$ of 10 mmHg.

Form of Use 4

The use as described herein, characterized in that the buffer solution has an effective carbon dioxide transport capacity of ≥500 ml/l at a pCO2 of 40 mmHg and an effective carbon dioxide transport capacity of ≥250 ml/l at a $pCO_2$ of 10 mmHg.

Form of Use 5

The use as described herein, characterized in that the buffer solution has a carbon dioxide partial pressure pCO2 of 0.2 mmHg±0.2.

Form of Use 6

The use as described herein, characterized in that the buffer solution contains the following components:

| Buffer A | TRIS | 36.0 mmol/l |
| Buffer B | Na$_2$HPO4 | 34.0 mmol/l |
| Titer | HCl | 12.0 mmol/l |

Embodiment 7

A buffer solution for use in the reduction of the carbon dioxide content in the blood of a patient suffering from pulmonary insufficiency or the complete failure of lung function, wherein the buffer solution has the features of the buffer solution used described herein.

Embodiment 8

An apparatus for the extracorporeal reduction of the carbon dioxide content in the blood (10), wherein the apparatus has a first delimited region (1) for receiving extracorporeal blood and a second delimited region (2) for receiving a buffer solution, wherein the first (1) and second region (2) adjoining each other in a contact zone are only separated by a membrane (3), via which gas exchange can occur between the blood and the buffer solution, and wherein the buffer solution has the features of the buffer solution as described herein.

Embodiment 9

The apparatus as described herein, characterized in that the membrane comprises at least one polymer selected from the group of polypropylene (PP), polymethylpentene (PMP), polysulfone (PSU) and optionally PVP or a mixture from the group of aforementioned polymers, in particular a mixture of polysulfone and polyvinylpyrrolidone.

Embodiment 10

The apparatus as described herein, characterized in that the membrane is formed from a plurality of hollow fibers.

Embodiment 11

The apparatus as described herein, characterized in that the membrane is coated with silicone, preferably that the membrane is formed with silicone-coated hollow fibers.

Embodiment 12

The apparatus as described herein, characterized in that the inner surface and/or the outer surface of the hollow fibers are coated with silicone.

Embodiment 13

The apparatus (10) according to claims 8 to 12 as described herein, characterized in that the first delimited region (1) for receiving the extracorporeal blood has an inlet port (4) and an outlet port (5) for the blood and is configured such that the blood can flow through the region from the inlet port (4) to the outlet port (5) in a first flow direction (6), and the second delimited region (2) for receiving the buffer solution has an inlet port (7) and an outlet port (8) for the buffer solution and is configured such that the buffer solution can flow through the region from the inlet port (7) to the outlet port (8) in a second flow direction (9), wherein the first flow direction (6) of the first region (1) and the second flow direction (9) of the second region (2) are oriented to run opposite to each other.

Embodiment 14

The apparatus (10) as described herein, characterized in that the exchange surface via which gas exchange can occur through the membrane (3) in the contact zone amounts to at least 0.3 m$^2$, particularly at least 0.6 m$^2$, particularly at least 1 m$^2$, preferentially at least 2 m$^2$.

Embodiment 15

The apparatus (10) as described herein, characterized in that the exchange surface via which gas exchange can occur through the membrane (3) in the contact zone amounts to at most 5 m$^2$, preferably at most 3 m$^2$.

Embodiment 16

The apparatus (10) as described herein, characterized in that the flow rate at which the blood flows through the first delimited region (1) amounts to at most 20% by volume, in particular at most 15% by volume, of the cardiac output of the patient for whom the carbon dioxide content in the blood is to be reduced extracorporeally with the apparatus.

Embodiment 17

The apparatus (10) as described herein, characterized in that the flow rate at which the blood flows through the second delimited region (2) amounts to 10 to 100% by volume, in particular 50 to 100% by volume, of the flow rate at which the blood flows through the first delimited region (1).

Embodiment 18

The apparatus (10) as described herein, characterized in that the apparatus comprises a device for regenerating the buffer solution, via which carbon dioxide taken from the blood can be removed again from the buffer solution.

Embodiment 19

The apparatus (10) as described herein, characterized in that the device for regenerating the buffer solution comprises means for supplying an acid to the buffer solution to be regenerated.

In a second aspect, the present disclosure relates to a system for the extra-corporeal blood treatment using a buffer solution and an apparatus for the extracorporeal reduction of the carbon dioxide content in blood in accordance with the first aspect of the present disclosure, wherein the system has a first inlet for introducing a bloodstream to be treated into the system, at least one blood treatment apparatus, as well as a first outlet for extracting a treated bloodstream from the system. The present disclosure further relates to a treatment apparatus having such a system as well as a kit comprising the components of the system. The present disclosure furthermore relates to a method for operating such a system and/or treatment apparatus with such a system. Furthermore, described is a method for extracorporeal blood treatment using such a system or such a treatment apparatus.

Systems for extracorporeal blood treatment are known in principle from the prior art. Systems are thereby also known which enable the combination of two different blood treatments. Corresponding methods for extracorporeal blood treatment using said systems are likewise known.

Known for example from WO 2015/067232 A1 is a system for peritoneal dialysis using an oxygenator arranged in an extracorporeal circuit.

DE 196 22 184 A1 describes a multifunctional device for multifunctional extracorporeal blood treatment, with which both a gas exchange treatment as well as a dialysis treatment are possible.

Further known, e.g. from EP 2 735 326 A1 or EP 0 236 0 509B1, is combining an extracorporeal dialysis treatment for continuous renal replacement therapy (CRRT) with an extracorporeal adsorption treatment for sepsis therapy in one common extracorporeal blood circuit.

EP 2 735 326 A1 discloses a system for blood treatment which comprises two dialyzers, each containing hollow fiber membranes, intended to be connected in series in an extracorporeal blood circuit for blood treatment and flowed through in succession, whereby one of the two dialyzers comprises an adsorbent material.

EP 0 236 0 509B1 likewise teaches arranging a dialyzer and an adsorber in series connection in an extracorporeal blood circuit for the combination of dialysis treatment and adsorption treatment.

Further known is combining an extracorporeal dialysis treatment for continuous renal replacement therapy with an extracorporeal gas exchange treatment for $CO_2$ removal from blood ($ECCO_2R$=ExtraCorporeal $CO_2$ Removal) or for extracorporeal ventilation with simultaneous oxygen enrichment (ECMO=ExtraCorporeal Membrane Oxygenation) in one common extracorporeal blood circuit.

Moreover, a blood treatment apparatus having a gas exchange apparatus is known from EP 2 461 847 B1 which enables an adsorption treatment in addition to gas exchange treatment, wherein the gas exchange apparatus comprises a carrier to that end which is coated with substances for the adsorptive removal of toxins of biological and chemical/synthetic origin, their metabolites and degradation products as present in blood, blood substitutes or solutions introduced into human and/or animal blood circulation.

In this context, it is a task of the present invention to provide an improved system for extracorporeal blood treatment, in particular an extracorporeal blood treatment system which is able to expand the possibilities of extracorporeal blood treatment and which provides additional treatment options, in particular on a flexible basis in each case depending on the respective treatment, without having to cannulate a further patient access or establish a further additional extracorporeal blood circuit. A further task of the present invention is that of providing a corresponding treatment apparatus, a corresponding kit, a corresponding method for operating such a system and/or a corresponding treatment apparatus as well as corresponding method for extracorporeal blood treatment.

These tasks are solved according to the present disclosure by a system for extracorporeal blood treatment having the features of embodiment 20, by a treatment apparatus having the features of embodiment 36, by a kit having the features of embodiment 37, by a method for operating such a system and/or treatment apparatus, as well as by a method for extracorporeal blood treatment using such a system or such a treatment apparatus. Advantageous embodiments of the present disclosure constitute the subject matter of the embodiments 21 to 35, the description and the figures and will be explained in greater detail in the following.

A system for extracorporeal blood treatment according to the present disclosure comprises a first inlet for introducing a bloodstream to be treated into the system, at least one first blood treatment apparatus, one second blood treatment apparatus, one third blood treatment apparatus, and a first outlet for extracting a treated bloodstream from the system.

The first blood treatment apparatus comprises an adsorber apparatus for removing at least one exogenous and/or at least one endogenous pathogen and/or a plasma separation apparatus for separating blood plasma from the other blood components, or is an adsorber apparatus and/or a plasma separation apparatus.

The second blood treatment apparatus is designed as a dialysis apparatus, in particular as a dialysis apparatus for renal replacement therapy, preferably continuous renal replacement therapy.

The third blood treatment apparatus is designed as an apparatus for the extracorporeal reduction of carbon dioxide content in blood (10) in accordance with one of the embodiments 8 to 19, particularly as a gas exchange apparatus for at least partially removing $CO_2$ from a bloodstream flowing through the first delimited region of the gas exchange apparatus and a buffer solution according to the features of at least one of the embodiments 1 to 6 flowing through the second delimited region of the gas exchange apparatus.

The first, second and third blood treatment apparatus are thereby sequentially connected in series between the first inlet and the first outlet of the system with respect to blood flow direction of a bloodstream to be treated in a functional application state of the system and a bloodstream to be treated can flow extracorporeally through same in succession. The sequential order of the arrangement of the blood treatment apparatus thereby preferably depends on the respective application.

An extracorporeal blood treatment in the context of the present disclosure is understood as a blood treatment occurring outside of a human or animal body, wherein extracorporeal blood treatment as such is generally known from the prior art.

A bloodstream in the context of the present disclosure is understood as a flow of mass comprising blood components.

A blood treatment apparatus in the context of the present disclosure is understood as an apparatus by means of which a blood mass, in particular a bloodstream, can be treated, i.e. its composition modified.

For extracorporeal blood treatment, a bloodstream to be treated, in particular blood to be treated; i.e. so-called whole blood containing all the components normally present in blood, or a bodily fluid to be treated having blood components such as plasma or the like, can be supplied to an herein disclosed system via the first inlet and can be discharged from the system via the system's first outlet.

In one embodiment of a system according to the present disclosure, the bloodstream to be treated can be supplied from, for example, a storage volume such as a preservation bag; i.e. a blood bag or the like, and/or the system supplied directly from a patient or animal to be treated.

The treated bloodstream can be discharged into a storage volume, for example likewise into an appropriate preservation bag or the like, and/or furnished to supply a separate transplant organ, and/or supplied directly to a patient or animal to be treated.

Particularly preferentially, a system for extracorporeal blood treatment according to the present disclosure is designed to be introduced into the human and/or animal blood circuit and in particular to be connected to the intracorporeal blood circuit of a patient or animal to be treated, thereby creating an extracorporeal blood circuit.

In one preferential embodiment of an herein disclosed system, the system is designed to have a veno-venous (VV) connection or an arterio-venous (AV) connection to the intracorporeal blood circuit of a patient or an animal. Depending on the application, the veno-venous or the arterio-venous connection of an herein disclosed system to the intracorporeal blood circuit of a patient or animal to be treated can be more advantageous. This depends in particular on the required blood treatment or the required blood treatments or required combination of blood treatments respectively. In a further embodiment, the herein disclosed system can also be connected to the intracorporeal blood circuit of a patient or animal via one or more artificially created blood access points such as, for example, a fistula or a shunt.

In a system for extracorporeal blood treatment according to the present disclosure, all variants relative to the sequential order of the arrangement of individual blood treatment apparatus in the direction of blood flow are in principle possible, wherein there is a total of 3!=6 arrangement possibilities, whereby some of these arrangement possibilities have particular advantages which will be explained in greater detail over the further course of this application.

Preferably, the first inlet and/or the first outlet of a system according to the present disclosure is/are formed by tubing lines with each preferably having at least one corresponding connection or, respectively, each preferably comprising one or more corresponding tubing lines, each in particular able to be connected to a blood vessel of a patient or animal to be treated and/or to a storage volume via a suitable access. The tubing lines of the present disclosure system can thereby form a tubing set, in particular an exchangeable tubing set.

Preferentially, an herein disclosed system for extracorporeal blood treatment comprises a supply line for introducing, in particular supplying, a bloodstream drawn from a patient and/or a bloodstream drawn from an animal and/or taken from a storage volume into the system and/or a return line for extracting, in particular removing, a treated bloodstream from the system and/or returning the treated bloodstream or a portion thereof into the intracorporeal blood circuit of a patient or animal to be treated and/or into a storage volume or a separate transplant organ.

In one preferential embodiment of an herein disclosed system, the system has at least one non-return valve in the return line in order to be able to block removal or respectively extraction of the treated bloodstream from the system, particularly in order to be able to prevent a return into the intracorporeal blood circuit of a patient or animal to be treated. The return line can further comprise a protective apparatus such as, for example, a filter or a magnetic apparatus in order to retain undesired particles and in particular prevent and/or inhibit said undesired particles from intruding into the intracorporeal blood circuit.

In the case of sepsis, additionally to continuous renal replacement therapy due to renal failure, respiration is often simultaneously indicated, particularly in intensive care patients. With a system according to the present disclosure, at least three blood treatments can be performed simultaneously and with only one extracorporeal blood circuit, these namely being a dialysis treatment, an adsorption treatment and/or a plasma separation and extracorporeal treatment for reducing the carbon dioxide content in the blood, particularly in conjunction with extracorporeal ventilation in place of or combined with mechanical ventilation requiring intubation or tracheotomy.

The extracorporeal treatment for the extracorporeal reduction of the carbon dioxide content in blood has the advantage over mechanical ventilation of also being able to treat patients with pulmonary insufficiency or complete failure of pulmonary function. Thus, particularly in cases affecting the lungs, as is frequently the case with sepsis, an extracorporeal treatment for reducing the carbon dioxide content in blood is more advantageous than mechanical ventilation. When combined with mechanical ventilation, the latter can become a less intensive process, which is less stressful for the patient.

The herein disclosed series connection of adsorber apparatus and/or plasma separation apparatus, dialysis apparatus and gas exchange apparatus, which is an apparatus for the extracorporeal reduction of carbon dioxide content in blood, furthermore makes only one extracorporeal blood circuit necessary. As a result, also patients with insufficient stability to simultaneous supply two extracorporeal blood circuits or whose state does not permit delayed extracorporeal blood treatment can simultaneously undergo an extracorporeal blood treatment comprising an adsorption treatment and/or a plasma separation, in particular a plasma treatment, a dialysis treatment and a gas exchange treatment, which is a treatment for the extracorporeal reduction of carbon dioxide content in the blood, with a system according to the present disclosure. In addition, fewer accesses are required with only one extracorporeal blood circuit. This thus reduces the stress on a patient as well as the risk of infection. In the sense of the present disclosure, a gas exchange apparatus is understood as an apparatus for the extracorporeal reduction of carbon dioxide content in blood according to the first aspect of the present disclosure, in particular an apparatus as defined in at least one of the embodiments 8 to 19. Furthermore, a treatment for the extracorporeal reduction of carbon dioxide content in blood is understood as being a gas exchange treatment in the context of the present disclosure.

By means of the sequential arrangement of an adsorber apparatus and/or a plasma separation apparatus, a dialysis apparatus and a gas exchange apparatus, a system according to the present disclosure for example simultaneously enables a sepsis treatment, a dialysis treatment with limited renal function or renal failure, as well as extra-corporeal ventilation.

An adsorber apparatus in the context of the present disclosure is an apparatus designed to remove from a bloodstream one or more components of the bloodstream flowing through said adsorber apparatus by means of adsorption. Adsorber apparatus are generally known from the prior art.

In one advantageous embodiment of an herein disclosed system, the first blood treatment apparatus is an adsorber apparatus, in particular an adsorber apparatus designed for endotoxin adsorption, cytokine adsorption and/or immuno-adsorption, or comprises such an adsorber apparatus. In particular, the adsorber apparatus is designed to remove at least one exogenous pathogen, e.g. to remove at least one pharmaceutical and/or at least one pharmaceutical substance and/or at least one plant toxin and/or organic toxin and/or other toxic substance and/or bacteria, viruses, fungi and/or other organisms and/or to remove at least one endogenous pathogen, e.g. to remove an immunocomplex and/or at least one immunoglobulin and/or at least one inflammatory response substance of the body (mediator) and/or antibodies and/or to remove at least one so-called pathogen-associated molecular pattern (PAMPs) and/or at least one so-called alarmin ("danger or damage-associated molecular pattern"—DAMPs).

A plasma separation apparatus in the context of the present disclosure is an apparatus by means of which blood plasma in a volume of blood introduced into the plasma separation apparatus can be at least partially separated from the other components of the volume of blood. A plasma separation apparatus in particular comprises a plasma filter and/or a centrifuge device or is designed as a plasma filter or centrifuge.

The dialysis apparatus of an herein disclosed system for extracorporeal blood treatment is preferentially designed to realize at least one method from among a group of different blood purification methods, preferably for continuous renal replacement therapy; i.e. CRRT treatment in particular for hemodialysis, hemofiltration, hemodiafiltration, hemoperfusion and/or for peritoneal dialysis, whereby dialysis apparatus of this type as well as the associated dialysis methods are likewise generally known from the prior art.

The gas exchange apparatus of an herein disclosed system is designed as an apparatus for the extracorporeal reduction of the carbon dioxide content in blood.

In one preferential embodiment of an herein disclosed system, the system, in particular the gas exchange apparatus, comprises membranes of hollow fibers coated with a silicone layer. In particular, the gas exchange apparatus can in one embodiment be designed as a (silicone-coated) hollow fiber membrane filter.

The gas exchange apparatus for the extracorporeal reduction of the carbon dioxide content comprises, according to the present disclosure, an apparatus in accordance with the first aspect of the disclosure, wherein the gas exchange apparatus has a first delimited region for receiving extracorporeal blood and a second delimited region for receiving the buffer solution described in accordance with the first aspect of the present disclosure, whereby the first and the second delimited region adjoining each other in a contact zone are only separated by a membrane via which gas exchange can occur between the blood and the buffer solution. The herein disclosed buffer solution described in the present application can be a component of the gas exchange apparatus for the extra-corporeal reduction of the carbon dioxide content in blood as an elimination medium.

In one specifically designed embodiment of the herein disclosed apparatus, the first delimited region for receiving the extracorporeal blood has an inlet port and an outlet port for the blood and is designed such that the blood can flow through the region from the inlet port to the outlet port in a first flow direction. The second delimited region for receiving the buffer solution has in this embodiment an inlet port and an outlet port for the buffer solution and is designed such that the buffer solution can flow through the region from the inlet port to the outlet port in a second flow direction.

Since in most applications there is insufficient pumping capacity of the heart or an implanted pump of a patient or animal to be treated to pump the flow of blood through the system or a veno-venous access for establishing the extracorporeal blood circuit for the extracorporeal blood treatment with an herein disclosed system is more advantageous; i.e. the bloodstream to be treated is taken from a vein and the treated bloodstream likewise returned to a vein, in one advantageous embodiment, the herein disclosed system comprises at least one first pump, in particular a first pump designed as a blood pump, for conveying at least a portion of a bloodstream to be treated, wherein the first pump is preferably arranged between the first inlet and the first blood treatment apparatus in the direction of blood flow and is in particular designed to convey the entire bloodstream to be treated. In other words, in one advantageous embodiment of an herein disclosed system, the first pump is preferably connected in series with the three blood treatment apparatus and is in particular arranged directly after the first inlet and ahead of the first blood treatment apparatus relative to the direction of blood flow.

In some cases, it can be more advantageous for the first pump to be arranged between the first blood treatment apparatus and the second blood treatment apparatus or between the second blood treatment apparatus and the third blood treatment apparatus or even after the third blood treatment apparatus, in each case in relation to the direction of blood flow in a functional usage of the herein disclosed system.

In one particularly preferential embodiment, an herein disclosed system comprises a plurality of pumps, in particular a plurality of pumps respectively designed as blood pumps for conveying the bloodstream to be treated, which are preferably connected in series with the treatment apparatus in the direction of blood flow and are in particular arranged in the blood flow direction such that the respective pressure conditions needed for optimal treatment are established at one or more of the blood treatment apparatus.

In one preferential embodiment, an herein disclosed system comprises a peristaltic pump as the first pump. In a particularly preferential embodiment, the herein disclosed system comprises a centrifugal pump as the first pump. This can be a diagonal pump configured as a rotor pump, wherein the pump preferably comprises a blood-guiding part decoupled from a drive part and the rotor of the pump is in particular supported via a ball bearing made in particular of ceramic or aluminum oxide preferably supported on a pin and preferably comprises permanent magnets on its underside facing the drive part and is able to be driven by means of magnetic coupling. Particularly preferential is for at least one pump to be designed such that there are only low shear stresses when flowing through the pump and the individual blood components, in particular the red blood cells, thus damaged as little as possible.

In one particularly preferential embodiment, a herein disclosed system comprises a pump designed in accordance with the blood pump described in DE 10 2010 024 650 A1. Preferably, the size of the blood pump, in particular its connection geometry, is thereby selected so as to be adapted to the respective bloodstream to be conveyed or to the volume of blood of the patient or animal to be treated respectively.

As the effectiveness of a hemofiltration blood treatment depends on a pressure gradient applied to the hemofilter, in particular on a hydrostatic pressure gradient between the two sides of the filter membrane, the so-called transmembrane pressure (TMP), it is advantageous relative to optimal hemofiltration blood treatment for an extracorporeal blood treatment system according to the present disclosure designed for hemofiltration or hemodiafiltration and/or a dialysis apparatus of a herein disclosed system designed for hemofiltration or hemodiafiltration to comprise at least one blood pump for conveying at least a portion of the bloodstream to be treated, by means of which a change in the bloodstream flow can be used to define a pressure established at least at one of the blood treatment apparatus and/or a resultant set pressure gradient, in particular a resulting transmembrane pressure on the dialysis membrane of the dialysis apparatus.

Preferentially, a system according to the present disclosure comprises a plurality of correspondingly designed and controllable pumps for setting a defined transmembrane pressure, in particular various correspondingly designed and controllable pumps such as, for example, one or more blood, dialysate, filtrate and/or substitute pumps, by means of which the blood flow can be set so as to result in a desired, defined transmembrane pressure on the hemofilter of the dialysis apparatus.

In a further advantageous embodiment of an herein disclosed system, the system comprises a further, in particular second, inlet for the addition of a first composition into the bloodstream, in particular into the bloodstream to be treated, wherein this further inlet is preferably arranged in the blood flow direction such that the first composition can be supplied to the bloodstream ahead of the first pump and/or ahead of the first of the three blood treatment apparatus, in particular ahead of the adsorber apparatus, in the direction of blood flow.

Preferentially, this further, in particular second, inlet is thereby designed for the addition of a liquid anticoagulant, in particular for the addition of an anticoagulant citrate solution. The herein disclosed system is thereby particularly preferentially designed such that the first composition, in particular an anticoagulant, can be supplied to the blood flow no later than ahead of a treatment section of the first treatment device; i.e. upstream of the first treatment device.

Particularly advantageously, the second inlet is thereby arranged such that the addition can occur upstream of the first pump; i.e. ahead of the first pump in the direction of blood flow. The risk of clotting within the system, in particular within an adsorber apparatus further downstream, can thus be reduced.

Clotting refers to the coagulation of blood components; i.e. a clumping of blood components.

A treatment section in the context of the present disclosure refers to a path of flow along which actual blood treatment occurs.

In some cases, it has proven advantageous for an herein disclosed system to comprise a further, in particular second, separate pump for conveying the first composition, in particular for pumping the first composition out of a first storage volume in which the first composition is accommodated into the bloodstream to be treated. The storage volume in which the first composition is preferably accommodated is in particular a preservation bag or an appropriate comparably designed container for storing the first composition, in particular a container enabling sterile storage of the composition along with sufficient shelf life.

Since hemofiltration and hemodiafiltration not only normally allow molecules from which the bloodstream to be treated is to be purified to pass through the filter membrane, the so-called hemofilter, of the dialysis apparatus but also some of the plasma fluid passes through the hemofilter and is also discharged as effluent, it is generally necessary in these cases; i.e. particularly in those cases in which the dialysis apparatus is designed for hemofiltration or for hemodiafiltration, to supply a substitute, usually a physiological substitution fluid, in particular an electrolyte solution, to the bloodstream to compensate for the resulting loss of fluid. The substitute can in principle be thereby supplied before and/or after the dialysis treatment. In some of these applications, it is more advantageous for the substitute to only be supplied to the bloodstream after the dialysis treatment; i.e. in particular only after the hemofilter, whereby in some cases it is particularly advantageous for it to be supplied only immediately prior to the treated blood mass flow being returned into the intracorporeal blood circuit of a patient or animal to be treated.

In hemodialysis; i.e. when the dialysis apparatus is designed for hemodialysis or hemodiafiltration, particularly when an anticoagulant citrate solution is added to the bloodstream, the bloodstream can be decalcified via the effluent, likewise needing to be compensated, wherein calcium loss thus resulting is preferably compensated downstream of the dialysis apparatus, in particular only after the last blood treatment apparatus.

In a further advantageous embodiment of an herein disclosed system, a herein disclosed system therefore has a further, in particular third, inlet for adding a second composition into the blood mass flow, in particular for adding a second composition into the treated blood mass flow, wherein said further inlet is preferably arranged in the blood flow direction such that the second composition can be supplied to the blood mass flow downstream of the dialysis apparatus in the direction of blood flow, in particular after the last blood treatment apparatus.

Said further, in particular third inlet is thereby in particular designed for the addition of a second composition in the form of a substitute for compensating for a loss of fluid occurring during hemofiltration or hemodiafiltration and/or for the addition of a second composition in the form of a liquid calcium solution for compensating for calcium loss occurring during hemodialysis.

That is to say, in other words, that in one preferred embodiment of an herein disclosed system for extracorporeal blood treatment, a second composition can be supplied to the blood mass flow preferably after the treatment section of the dialysis apparatus and/or after a dialysis procedure. Particularly preferentially, the second composition can be supplied to the bloodstream directly prior to its return into the intracorporeal blood circuit, in particular introduced directly into the return line.

In some cases, it has proven advantageous for a herein disclosed system to have a further pump, in particular a third pump, for conveying the second composition, which is in particular designed to pump the second composition from a second storage volume in which the second composition is accommodated into the bloodstream.

In some cases, however, it can also be advantageous for a further, in particular separate inlet to be provided for supplying the required substitute for compensating for a resulting loss in fluid or volume in the dialysis apparatus during hemofiltration or hemodiafiltration, in particular an additional inlet to the third inlet or to the inlet provided to compensate for a calcium loss respectively.

In some cases, it can be advantageous for the respective inlet for supplying the substitute to thereby be arranged in the direction of blood flow such that the substitute can be supplied to the bloodstream ahead of the gas exchange treatment in the blood flow direction, wherein the associated inlet is in particular arranged directly prior to the gas exchange apparatus relative to the blood flow direction in order to be able to compensate for any potential undesirable $CO_2$ loading of the substitute via the gas exchange apparatus. In some applications, is more advantageous only supply the substitute to the bloodstream after the dialysis and adsorption treatment so as to prevent a diluting effect which would reduce the effectiveness of the adsorption treatment (as a general rule, adsorption potency is dependent on concentration).

As already stated previously, the adsorber apparatus and/or the plasma separation device, the dialysis apparatus and the gas exchange apparatus can in principle be sequentially connected in series in any order in a herein disclosed system, whereby, however, certain arrangements; i.e. a specific sequence of flow through the individual treatment apparatus in the direction of blood flow, are particularly advantageous.

One particularly advantageous embodiment of a herein disclosed system for extracorporeal blood treatment results from the adsorber apparatus and/or the plasma separation apparatus being arranged ahead of the gas exchange apparatus in the direction of blood flow. Since a substitute, usually a physiological substitution fluid, preferably an electrolyte solution, which in some cases can be loaded with $CO_2$, is generally also to be supplied to the blood mass flow following an adsorption treatment to compensate for the volume lost during treatment, it is advantageous for the adsorber apparatus to be arranged ahead of the gas exchange apparatus in the blood flow direction since an undesired $CO_2$ loading effected by the substitution fluid can thereby be compensated for again by means of the gas exchange apparatus. As a result, improved $CO_2$ removal from the blood mass flow to be treated can thus be achieved compared to an arrangement of the gas exchange apparatus ahead of the adsorber apparatus.

In one alternative, in some cases likewise advantageous embodiment of a herein disclosed system, the adsorber apparatus and/or the plasma separation apparatus is/are arranged after the gas exchange apparatus in the direction of blood flow. Advantageous with this arrangement is being able to achieve an increase in the pressure gradient in the gas exchange apparatus, in particular on the gas exchange membrane, from the resulting back pressure at the adsorber apparatus, whereby the gas exchange can be improved.

In order to supply the needed substitute for compensating the volume loss occurring in the adsorber apparatus during the adsorption treatment, a system according to the present disclosure preferably has a further, in particular fourth inlet to the blood mass flow which is in particular arranged in the blood flow direction such that the substitute can be supplied to the blood mass flow following the absorption procedure in the blood flow direction, in particular after the treatment section in the adsorber apparatus, wherein the fourth inlet is in particular arranged directly after the adsorber apparatus in relation to the blood flow direction.

In some cases, however, it may also be (more) advantageous to arrange the fourth inlet ahead of the adsorber apparatus, in particular upstream of the gas exchange apparatus, in order to be able to compensate for undesired $CO_2$ loading of the bloodstream via the gas exchange apparatus caused by the substitution fluid required to compensate for the loss of fluid occurring during the adsorption treatment. This is particularly the case when the adsorber apparatus is arranged after the gas exchange apparatus in the blood flow direction; i.e. downstream of the gas exchange apparatus.

In a further advantageous embodiment of a herein disclosed system, the adsorber apparatus and/or the plasma separation device is/are arranged ahead of the dialysis apparatus in the direction of blood flow, particularly when the dialysis apparatus is designed for hemodialysis or hemodiafiltration and in particular comprises a dialyzer. The upstream arrangement of the adsorber apparatus; i.e. ahead of the dialysis apparatus in the blood flow direction, has the advantage of no dialysate-diluted bloodstream being supplied to the adsorber apparatus, whereby particularly high adsorption treatment efficiency can be achieved.

Furthermore, the downstream arrangement of the dialysis apparatus can compensate for non-specific ionic bonds or pH shifts occurring in the absorber.

In addition, due to its structure of small(est) hollow fibers, the bloodstream downstream arrangement of the dialysis apparatus can act as a safety system against an undesired intrusion of particles from the adsorber device.

If the dialysis apparatus of a system according to the present disclosure is designed for hemodialysis or hemodiafiltration and in particular comprises a dialyzer, a system according to the present disclosure, in particular the dialysis apparatus, preferably has a fifth inlet for supplying a dialysate; i.e. a dialysis fluid.

For the removal of effluent occurring in the dialysis apparatus during the dialysis treatment, a system according to the present disclosure preferably has a second outlet.

In one alternative embodiment of a herein disclosed system, the adsorber apparatus is arranged after the dialysis apparatus in the direction of blood flow, particularly when the dialysis apparatus is designed for hemofiltration or hemodiafiltration and preferably comprises a hemofilter. This sequential arrangement can be advantageous in some applications, in particular when particularly effective adsorption treatment is indicated, since in this case the bloodstream to be treated can be concentrated in the dialysis apparatus by hemofiltration, whereby the effectiveness of the adsorption treatment in the downstream arranged adsorber apparatus can be increased.

In this case, although the clotting risk of the system, particularly in the adsorber apparatus, increases relative to the previously described embodiments of a herein disclosed system, incipient clotting can in many cases be identified relatively reliably and promptly by the appropriate monitoring measures such as, for example, pressure sensor devices respectively arranged ahead of and after at least one blood treatment apparatus, by means of which the state of the respective blood treatment apparatus can be deduced. Thus, particularly in conjunction with the additional use of anticoagulants, the risk of clotting can in most cases be well controlled.

In a further advantageous embodiment of a the herein disclosed system, the dialysis apparatus is arranged ahead of the gas exchange apparatus in the blood flow direction, particularly when the dialysis apparatus is designed for hemodialysis or hemofiltration and requires the supply of a dialysate for dialysis treatment. In this case, an undesired $CO_2$ loading by a potentially $CO_2$-laden dialysate in the dialysis apparatus can be compensated for via the gas exchange apparatus arranged sequentially after the dialysis apparatus in the blood flow direction prior to the treated bloodstream being returned to the intracorporeal blood circuit of a patient or animal to be treated, which would not be the case with an arrangement of the dialysis apparatus after the gas exchange apparatus.

In an alternative yet also in some cases advantageous embodiment of a herein disclosed system, the dialysis apparatus is arranged after the gas exchange apparatus in the blood flow direction, whereby in this case, the dialysis apparatus is preferably designed for hemofiltration and comprises a hemofilter and is in particular not designed for hemodialysis.

The pressure gradient on the gas exchange apparatus between the blood side and the gas side can be increased by means of the hemofilter downstream of the gas exchange apparatus, whereby the efficiency of the gas exchange apparatus can be improved.

Should the dialysis apparatus be designed solely for hemofiltration and not for hemodialysis, particularly also not for hemodiafiltration, the disadvantage of undesired $CO_2$ loading as a result of bloodstream exchange with a conceivably $CO_2$-laden supplied dialysate as in possible in hemodialysis or hemodiafiltration, does not arise. In the latter case, the substitution solution for volume compensation can preferably already be added upstream of the gas exchanger in order to be able to at least partially, preferably fully, compensate for potential $CO_2$ loading via the gas exchange apparatus.

In a further advantageous embodiment of a herein disclosed system, the system comprises at least one pressure sensor device for determining a flow pressure of the bloodstream at least at one defined point in the system, wherein at least one pressure sensor device is preferably arranged directly in front of and/or directly after at least one treatment section of a blood treatment apparatus in the direction of blood flow.

If respective pressure sensor devices are provided before and after at least one treatment section, the drop in pressure over the treatment section can thereby be detected, from which the state of the associated blood treatment apparatus can be deduced. In particular, the extent to which a blood treatment apparatus is affected by clotting can thereby be assessed, whereby a suddenly increasing drop in pressure indicates that the respective blood treatment apparatus is affected by clotting.

In one preferential embodiment, a system according to the present disclosure comprises a control device, wherein the control device is in particular designed to control and/or regulate all of the system components of the herein disclosed system able to be controlled and/or regulated. That is to say, in other words, in one preferential embodiment, a system according to the present disclosure has a common controller for controlling all the blood treatment apparatus. The controller is thereby in particular designed to control one or more pumps, and/or to control inflow and/or outflow amounts of substances and/or compositions, and/or to evaluate the sensor data recorded by at least one sensor device and/or to monitor the herein disclosed system, particularly to control and/or regulate the bloodstream to be treated.

Preferentially, blockages or an interruption of the blood circuit can be detected with the aid of one or more pressure sensor devices and corresponding measures tripped such as, for example, the triggering of an alarm or the shutting off of the system, in particular a pump conveying the bloodstream.

Preferably, a system according to the present disclosure is thereby designed such that a defined transmembrane pressure as required for the highest possible effectiveness of a blood treatment is monitored in relation to a limit value for at least one of the blood treatment apparatus, in particular for the dialysis apparatus. Preferably, the flow of the bloodstream can be adjusted as a function of at least one sensor signal detected by a pressure sensor device such that a desired defined transmembrane pressure is set or respectively results so that an improved blood treatment can be achieved.

In a further advantageous embodiment of a herein disclosed system, a herein disclosed system preferably comprises at least one gas bubble detection device for detecting a gas bubble in the bloodstream. Preferably, the system is thereby designed such that upon a gas bubble being detected by the gas bubble detection device, a non-return valve arranged in particular in front of the first outlet, preferably in a return line, can be closed so as to prevent the gas bubble from returning into the intracorporeal circuit along with the treated bloodstream, in particular the intracorporeal blood circuit, of a patient or animal to be treated. Furthermore, preferably all the pumps serving to convey the bloodstream can additionally be switched off.

In a further advantageous embodiment of a herein disclosed system, a treatment section of at least one blood treatment apparatus is at least partially, preferably entirely, formed by an exchangeable treatment module, in particular a cartridge-like treatment module. Such a blood treatment apparatus configuration enables a flexible replacement of the respective treatment module, in particular a simple and flexible adapting of the individual treatment apparatus to the respectively required blood treatment.

For example, an endotoxin adsorber treatment module can thereby be easily exchanged for a cytokine adsorber treatment module having another functional adsorption layer or a special immune adsorber treatment module used or a hemofilter exchanged for a dialyzer or the like. The range of treatments possible with a system according to the present disclosure thereby increases considerably, whereby the economic efficiency of a system according to the present disclosure can be significantly increased.

In a further advantageous embodiment of a presently disclosed system, the system comprises at least one switchable bypass device for bypassing at least one blood treatment apparatus. A herein disclosed system can thereby if needed also be used for blood treatments which each require only the use of one or two of the three blood treatment apparatus of the system but does not, however, require flowing through all three blood treatment apparatus of a herein disclosed system. In this way, a required blood treatment which for example only requires an adsorption treatment and/or only plasma separation and a dialysis treatment can be carried out while bypassing the gas exchange apparatus. A dialysis treatment with subsequent gas exchange for $CO_2$ removal is likewise possible without simultaneous adsorption treatment. The range of treatment options can thereby be increased significantly with a herein disclosed system. Furthermore, treatment costs can be significantly reduced in a multitude of treatment cases because material consumption can be significantly lowered since three treatment modules are not in each case consumed. Moreover, a treatment apparatus can be removed from the system when it no longer fulfills its function because, for example, of being clotted or depleted such as e.g. a fully loaded adsorber.

Preferably, at least one bypass device comprises at least one bypass valve as well as an associated bypass line which is in particular fluidly connected or connectable to a main line, wherein the associated bypass line can be opened or closed in particular by means of a bypass valve such that a bloodstream to be treated can be selectively guided along the associated bypass line or can be selectively guided through the subsequent blood treatment apparatus or the subsequent blood treatment section respectively.

Preferentially, at least one bypass valve is thereby designed such that when the bypass valve is open, there is no flow through the downstream treatment section; i.e. the subsequent blood treatment apparatus can preferably be completely blocked and the entire bloodstream to be treated can be guided past the associated blood treatment apparatus via the associated bypass line; i.e. the blood treatment apparatus can be bypassed.

In the sense of the present disclosure, "bypassing a blood treatment apparatus" is in particular understood as a branching of the main line, in particular routing a bypass line around the blood treatment apparatus at a branching point upstream of the blood treatment apparatus or in the blood treatment apparatus and joining the bypass line back to the main line again downstream, in particular after the blood treatment apparatus or in the blood treatment apparatus.

When the bypass valve is in contrast closed, the bypass line is preferably blocked, in particular completely, so that the entire bloodstream to be treated flows through the subsequent treatment section or the subsequent blood treatment apparatus respectively.

In doing so, flow runs selectively through only the treatment apparatus required. The possible uses of a system according to the present disclosure can thereby be increased significantly. In particular, the utilization or utilization period respectively of a herein disclosed system can thereby be improved, whereby the economy efficiency can in turn be increased.

In order to set a defined flow rate of the bloodstream at least at one of the blood treatment apparatus, in particular to induce a desired defined transmembrane pressure, in particular for at least one associated treatment section, a herein disclosed system can comprise at least one further pump, arranged in particular in a section between a branching point and the subsequent junction into the main line and/or bypass line.

With an appropriate number and design of the individual pumps, an independent regulating of the blood flow rates can thereby be achieved in the individual treatment apparatus, wherein the system in particular comprises one or more correspondingly designed control devices to that end.

In one advantageous embodiment, at least one bypass device associated with a blood treatment apparatus is designed such that a recirculating blood flow can be effected via and/or through the associated device.

In a further advantageous embodiment of a herein disclosed system, at least one further blood treatment apparatus is arranged in the associated bypass line of at least one blood treatment apparatus, in particular such that a recirculating blood flow ensues from the associated blood treatment apparatus arranged in the main line and/or by the further blood treatment apparatus arranged in the bypass line.

In one alternative advantageous embodiment of a herein disclosed system, the first blood treatment apparatus is a plasma separation device which can preferably be bypassed by means of a bypass line, wherein a further blood treatment apparatus in the form of an adsorber apparatus is in particular arranged in the bypass line. The adsorber apparatus is thereby preferably arranged downstream of a pump arranged in the bypass line.

The treated blood discharged from the absorber apparatus, or the treated blood plasma discharged from the absorber apparatus respectively, can thereby be either supplied to the main line after the plasma separation apparatus or supplied to the plasma separation apparatus in recirculating manner.

In one alternative embodiment of a herein disclosed system, separated plasma can be discharged from the plasma separation apparatus, particularly by means of a pump, and fed to a plasma disposal container and fresh plasma, in particular from a storage apparatus, supplied via a further inlet, in particular the main line, preferably by means of a further pump.

In a further advantageous embodiment of a herein disclosed system, at least one component of the system comprises a biocompatible and preferably functional coating on a surface coming into contact with the bloodstream to be treated, in particular an antibacterial, anticoagulant and/or anti-inflammatory coating. Preferably, at least one lumen of the system, which is designed for a bloodstream to be treated and/or a treated bloodstream to flow through, is provided with a biocompatible and preferably functional coating, in particular an antibacterial, anticoagulant and/or anti-inflammatory coating.

Preferably, at least one surface of the herein disclosed system thereby has a coating containing heparin and/or albumin and heparin. In some cases, it may be advantageous for the system to in contrast have only heparin-free coatings as the system can thereby also be used to treat patients or animals with a heparin intolerance.

In an alternative and/or additional preferred embodiment of a herein disclosed system, at least one coating exhibits defined antibodies and/or one or more enzymes. An antibacterial coating is also conceivable.

In a further advantageous embodiment of a herein disclosed system, at least one protective layer is applied to protect the functional coating, wherein the protective layer preferably serves to enable sterilization and/or storage of individual coated components of the system without any significant loss of functionality of the functional coating.

In one particularly preferential embodiment of a herein disclosed system, the system comprises at least one surface having a coating formed using the SPS® technology from Leukocare AG.

A herein disclosed treatment apparatus for extracorporeal blood treatment comprises a system for extracorporeal blood treatment designed according to the present disclosure, wherein the first, the second and the third blood treatment apparatus of the system are in particular arranged in a common housing and/or are accommodated by a common base; i.e. by a common carrier device.

Preferably, the three blood treatment apparatus are thereby arranged in a common housing and/or are accommodated by a common base such as, for example, a common carrier device or the like. Particularly preferentially, each individual blood treatment apparatus is thereby replaceably secured in and/or on the common housing and/or base, in particular as respective replaceable modules. Thereby able to be provided is a particularly compact herein disclosed system which can at the same time be flexibly tailored and configured to each respective treatment case.

A herein disclosed kit and/or set for extracorporeal blood treatment has as components at least one first blood treatment apparatus, a second blood treatment apparatus, a third blood treatment apparatus and a tubing set having a first inlet for introducing a bloodstream to be treated and a first outlet for discharging a treated bloodstream via one or more tubes as well as in particular an installation and/or operating manual.

The first blood treatment apparatus is thereby an adsorber apparatus for removing at least one exogenous and/or at least one endogenous pathogen and/or a plasma separation apparatus for separating blood plasma from the other blood components or comprises a corresponding adsorber apparatus and/or plasma separation apparatus. The second blood treatment apparatus is designed as a dialysis apparatus, in particular as a dialysis apparatus for renal replacement therapy, and the third blood treatment apparatus is designed as a gas exchange apparatus formed as an apparatus for extracorporeally reducing the carbon dioxide content in blood in accordance with one of the embodiments 8 to 19, in particular as a gas exchange apparatus for the at least partial removal of $CO_2$ from a bloodstream flowing through the first delimited region of the gas exchange apparatus and a buffer solution flowing through the second delimited region of the gas exchange apparatus designed in accordance with the features of at least one of the forms of use 1 to 6. The components of the kit can be as herein disclosed connected to a system designed for extracorporeal blood treatment as per the present disclosure, in particular according to the installation and/or operating manual.

A particularly flexible system as herein disclosed which enables a combination of adsorber apparatus and/or plasma separation device, dialysis apparatus and gas exchange apparatus specifically tailored to the respective treatment case can thereby be easily provided.

That is to say, a herein disclosed system can be provided both in the form of a common treatment apparatus, with the three blood treatment apparatus of the system; i.e. the adsorber apparatus and/or the plasma separation device, the dialysis apparatus and the gas exchange apparatus being part of a common device, as well as in the form of a kit and/or set in which at least two of the three blood treatment apparatus are separate apparatus although are able to be connected into a herein disclosed system by means of a suitable tubing system having one or more hoses and able to be connected as herein disclosed sequentially in series such that each individual blood treatment apparatus can be flowed through sequentially in series.

A method according to the present disclosure for operating a herein disclosed system for extracorporeal blood treatment and/or a herein disclosed treatment apparatus is characterized by the following steps:
 providing an amount of blood to be treated,
 introducing a bloodstream to be treated into the system via the first inlet of the system,
 flowing through at least one of the blood treatment apparatus, and
 extracting the treated bloodstream via the first outlet of the system.

Preferably, if the system used for extracorporeal blood treatment is designed thereto and comprises at least one switchable bypass device, flow thereby only runs through the blood treatment apparatus required, the use of which is indicated for the respective treatment.

In one advantageous embodiment of a method according to the present disclosure for operating a herein disclosed system, the blood mass to be treated is provided in a container, in particular in a container or a bag, whereby the treated blood is preferably extracted to a container, in particular into a container or a bag. Alternatively, the treated blood can also be supplied to a separated organ intended for transplant or to a patient to be treated or to an animal to be treated.

A method according to the present disclosure for extracorporeal blood treatment with a herein disclosed system or a herein disclosed treatment apparatus is characterized by the steps:
 introducing the system into a blood circuit of a human or animal to be treated and establishing an extracorporeal blood circuit by connecting the first inlet of the system to a first blood vessel of the human or animal to be treated and connecting the first outlet of the system to the first blood vessel and/or a second blood vessel of the human or animal,
 withdrawing a bloodstream to be treated from the intracorporeal blood circuit of the human or animal and introducing the bloodstream to be treated into the system via the first inlet of the system,
 flowing through at least one of the blood treatment apparatus,
 extracting the treated bloodstream via the first outlet of the system and returning the treated bloodstream to the intracorporeal blood circuit of the human or animal.

Depending on the circumstances, the herein disclosed system can thereby be connected veno-venous or arterio-venous to the intracorporeal blood circuit of a human or animal to be treated or alternatively via at least one artificially created blood access point.

Particularly suitable for the veno-venous connecting of a herein disclosed system to an intracorporeal blood circuit of a human or animal to be treated is a double lumen cannula with concentrically arranged inlet and outlet such as, for example, the "NovaPort® twin" cannula for adult patients sold by the Novalung GmbH company; i.e. in a herein disclosed method for extracorporeal blood treatment, the system is introduced into a blood circuit of a human or animal to be treated and the extracorporeal blood circuit is preferably established using a double lumen cannula.

In addition to deriving from the embodiments 20 to 37 and the description, these and further features of the present disclosure also derive from the associated figures as well as the description of the figures, wherein all the cited and/or depicted features and feature combinations can be realized in an embodiment of the present disclosure not only in the combination as respectively indicated but also in other combinations or alone, provided same is technically feasible.

Some of the cited and/or depicted features or properties respectively of the present disclosure relate both to a herein disclosed system, a herein disclosed treatment apparatus, a herein disclosed kit, a herein disclosed method for operating the herein disclosed system and/or a herein disclosed treatment apparatus as well as to a herein disclosed method for extracorporeal blood treatment with a herein disclosed system or with a herein disclosed treatment apparatus, wherein some of these features and properties are only described once, for example only in conjunction with the herein disclosed system, although nonetheless apply within the scope of technically possible embodiments to both a herein disclosed system as well as a herein disclosed treatment apparatus, an herein disclosed kit, a herein disclosed method for operating such a system and/or a herein disclosed treatment apparatus as well as a herein disclosed method for extracorporeal blood treatment with such a system or herein disclosed treatment apparatus.

Figure 4:
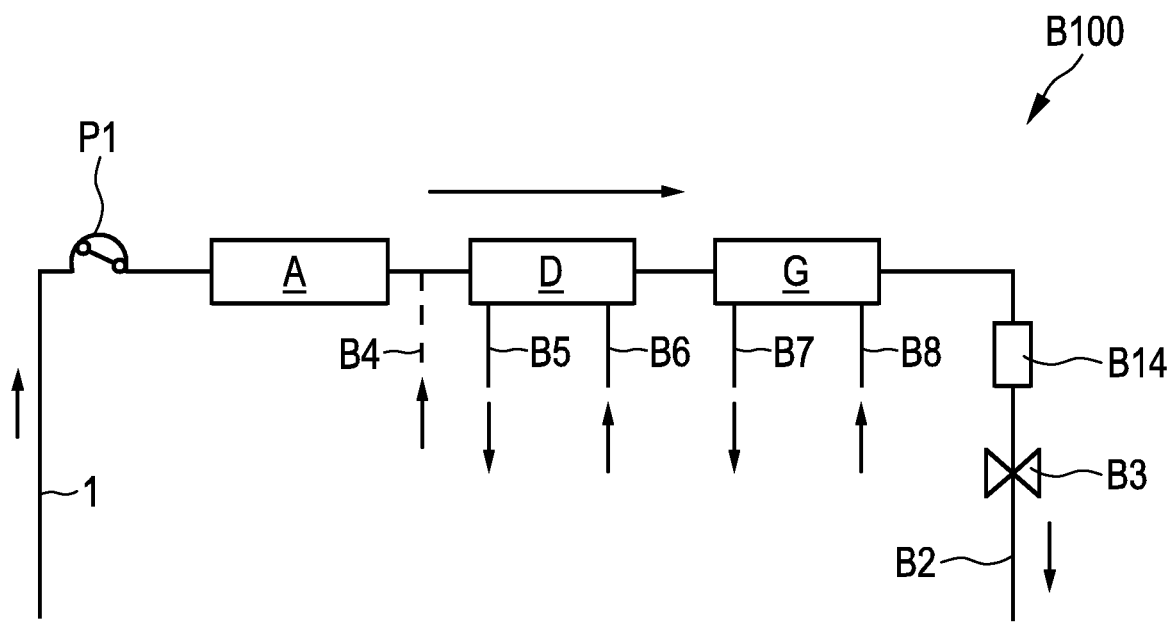
FIG. 4 is a schematic depiction of the basic structure of a first exemplary embodiment of a system according to the present disclosure.
Figure 5:
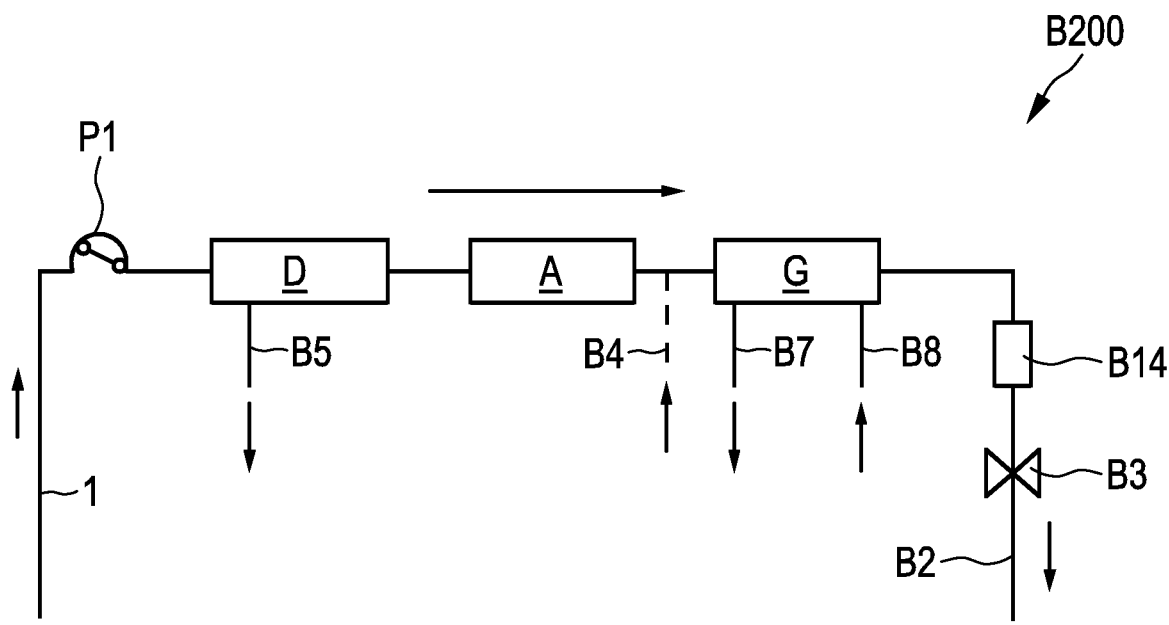
FIG. 5 is a schematic depiction of the basic structure of a second exemplary embodiment of a system according to the present disclosure.
Figure 6:
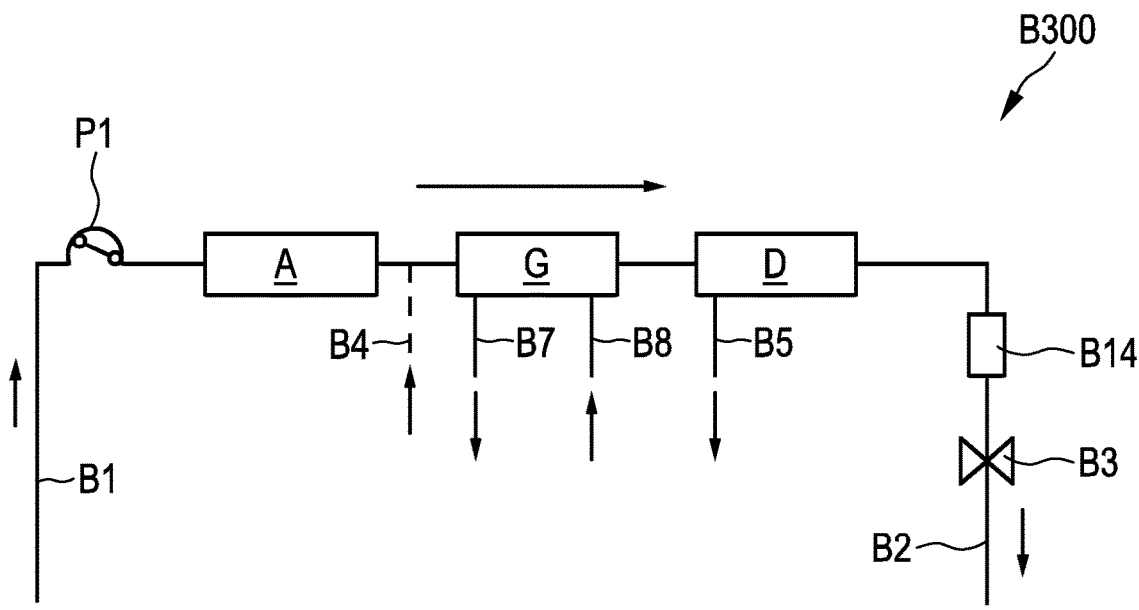
FIG. 6 is a schematic depiction of the basic structure of a third exemplary embodiment of a system according to the present disclosure.
Figure 7:
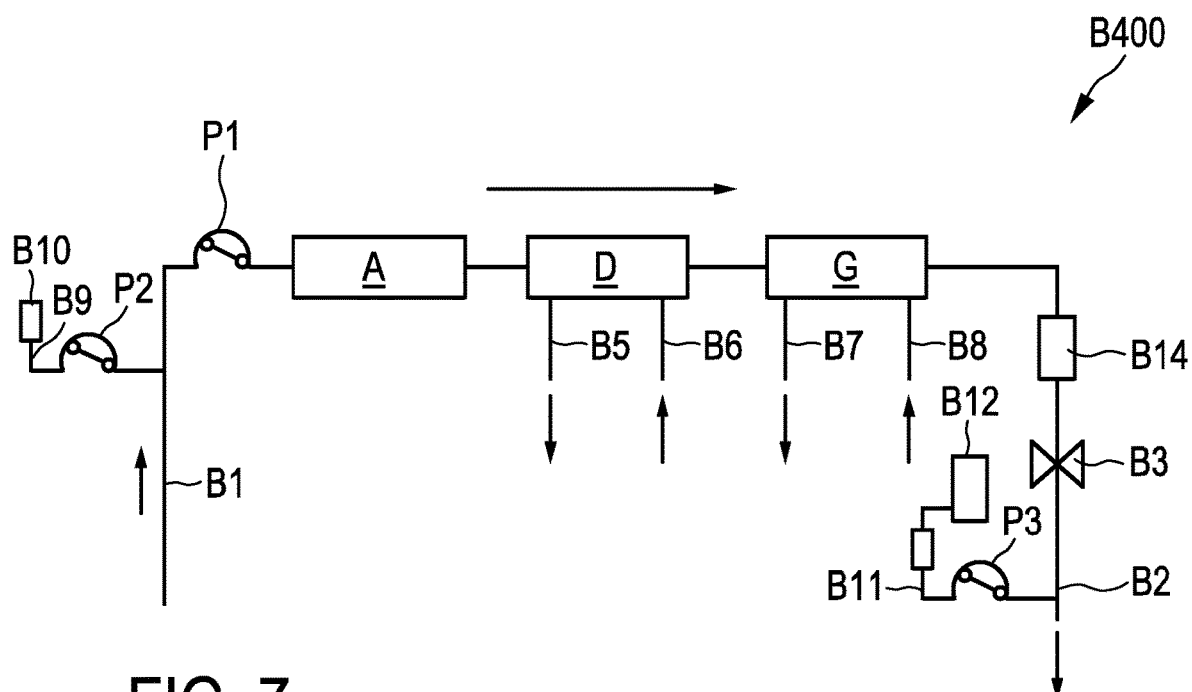
FIG. 7 is a schematic depiction of the basic structure of a fourth exemplary embodiment of a system according to the present disclosure.
Figure 8:
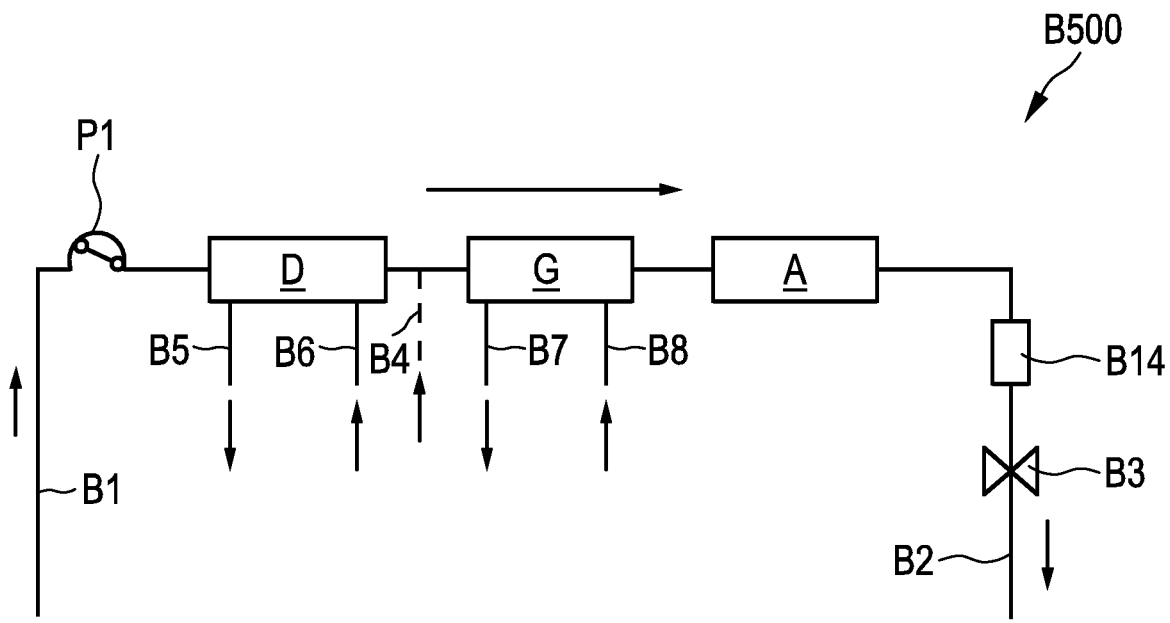
FIG. 8 is a schematic depiction of the basic structure of a fifth exemplary embodiment of a system according to the present disclosure.
Figure 9:
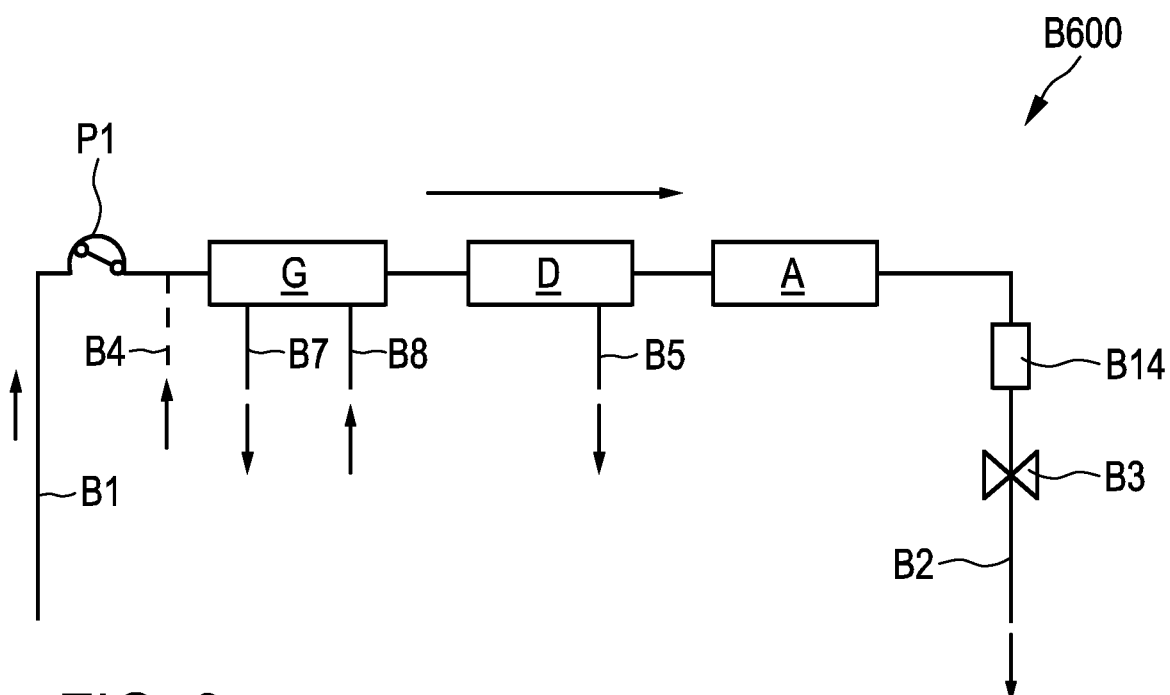
FIG. 9 is a schematic depiction of the basic structure of a sixth exemplary embodiment of a system according to the present disclosure.
Figure 10:
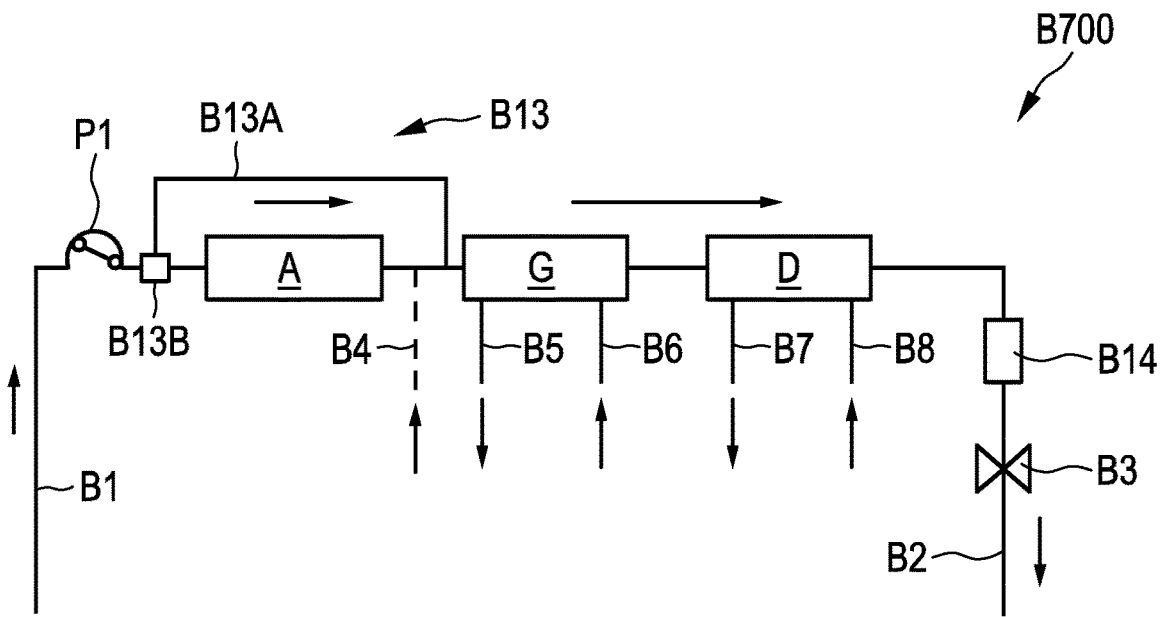
FIG. 10 is a schematic depiction of the basic structure of a seventh exemplary embodiment of a system according to the present disclosure.
Figure 11:
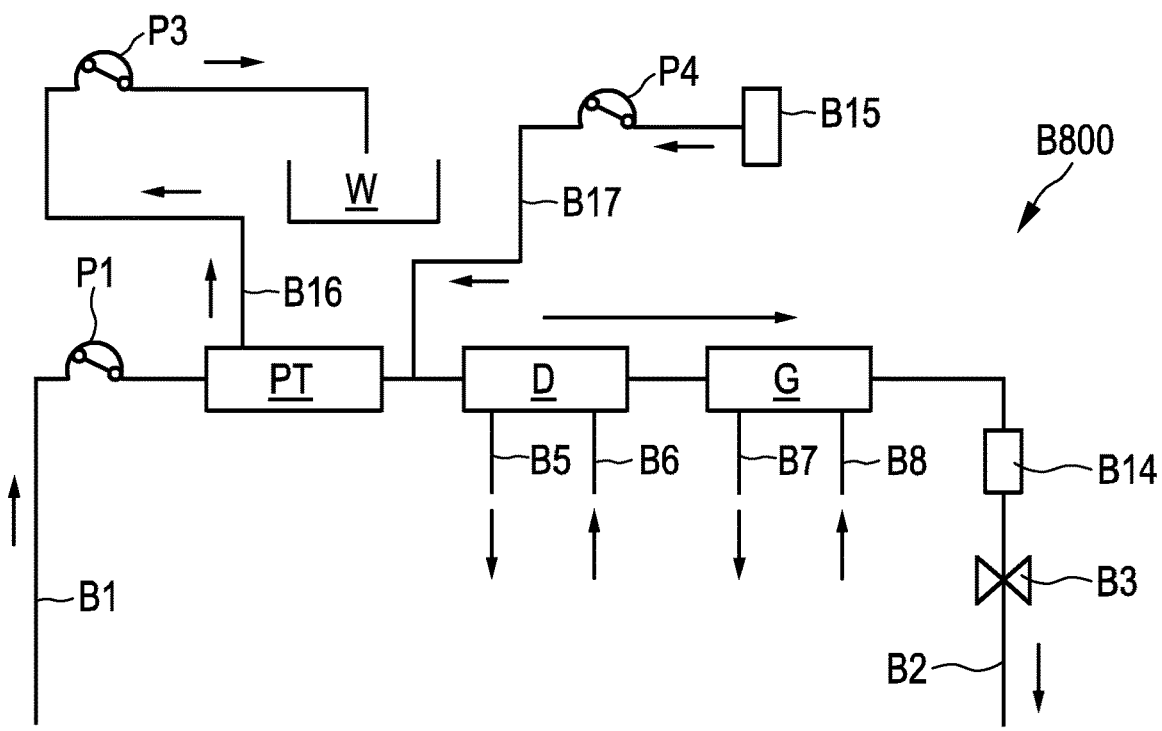
FIG. 11 is a schematic depiction of the basic structure of an eighth exemplary embodiment of a system according to the present disclosure.
Figure 12:
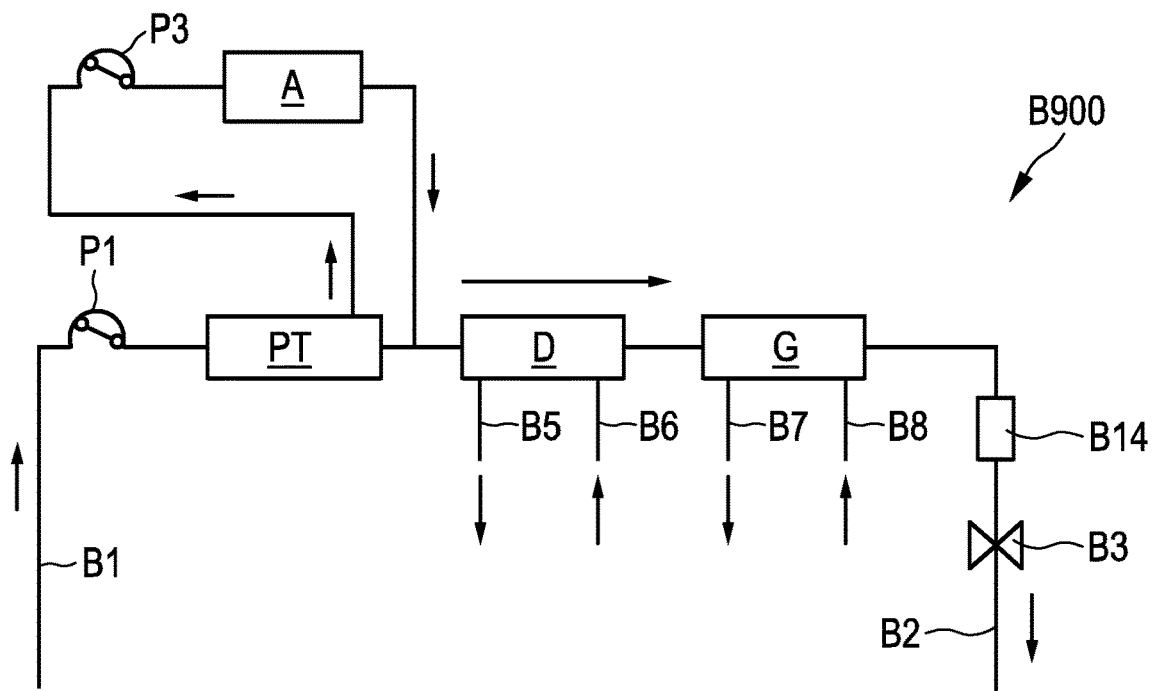
FIG. 12 is a schematic depiction of the basic structure of a ninth exemplary embodiment of a system according to the present disclosure.
Figure 13:
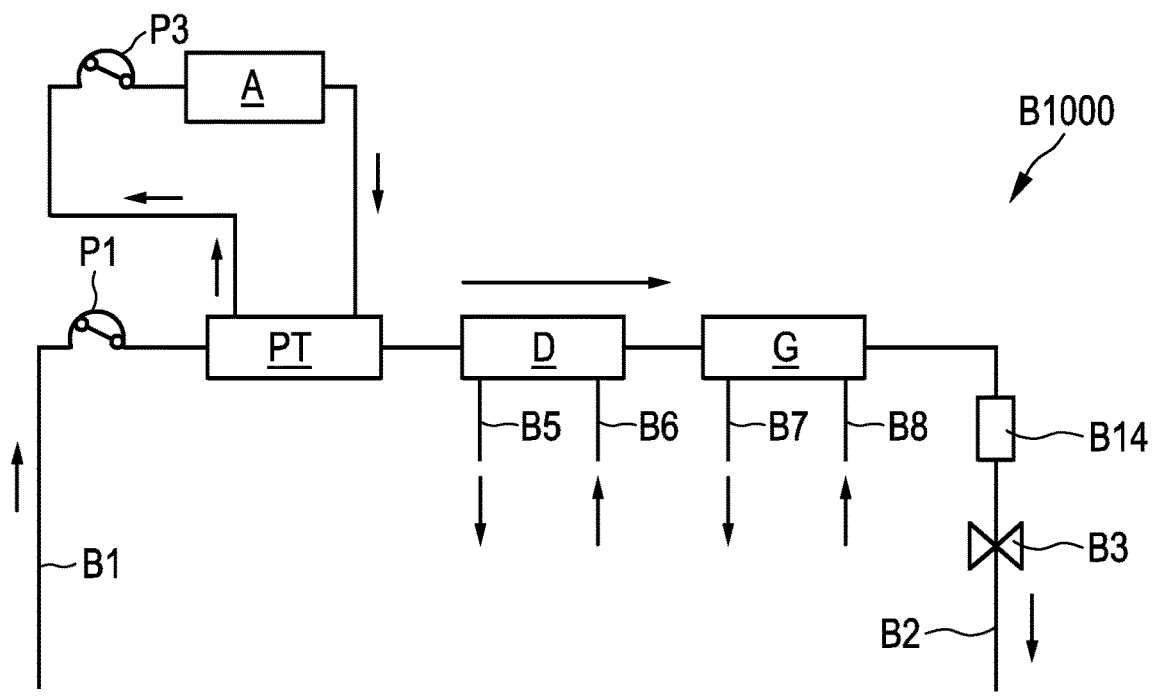
FIG. 13 is a schematic depiction of the basic structure of a tenth exemplary embodiment of a system according to the present disclosure.

The following will reference the accompanying figures in defining the present disclosure in greater detail based on a plurality of exemplary embodiments, wherein functionally identical components are indicated by the same reference numerals unless otherwise explicitly stated or indicated by the context. Shown are:

FIG. 4 a schematic depiction of the basic structure of a first exemplary embodiment of a system according to the present disclosure, FIG. 5 a schematic depiction of the basic structure of a second exemplary embodiment of a system according to the present disclosure, FIG. 6 a schematic depiction of the basic structure of a third exemplary embodiment of a system according to the present disclosure, FIG. 7 a schematic depiction of the basic structure of a fourth exemplary embodiment of a system according to the present disclosure, FIG. 8 a schematic depiction of the basic structure of a fifth exemplary embodiment of a system according to the present disclosure, FIG. 9 a schematic depiction of the basic structure of a sixth exemplary embodiment of a system according to the present disclosure, FIG. 10 a schematic depiction of the basic structure of a seventh exemplary embodiment of a system according to the present disclosure, FIG. 11 a schematic depiction of the basic structure of an eighth exemplary embodiment of a system according to the present disclosure, FIG. 12 a schematic depiction of the basic structure of a ninth exemplary embodiment of a system according to the present disclosure, and FIG. 13 in a schematic depiction of the basic structure of a tenth exemplary embodiment of a system according to the present disclosure.

FIG. 4 shows a schematic depiction of the basic structure of a first exemplary embodiment of a herein disclosed system B100 for extracorporeal blood treatment, wherein the system B100 comprises a first inlet formed by a supply line B1 for introducing a bloodstream to be treated into the system B100, three blood treatment apparatus A, D and G, as well as a first outlet formed by a return line B2 for extracting a treated bloodstream from the system B100.

A first blood treatment apparatus A is thereby an adsorber apparatus A designed for endotoxin adsorption. A second blood treatment apparatus D is designed as a dialysis apparatus D, in particular for hemodialysis. A third blood treatment apparatus G is a gas exchanger designed as an apparatus for reducing the carbon dioxide content from the bloodstream to be treated in accordance with the first aspect of the present disclosure.

The herein disclosed system B100 depicted in FIG. 4 is thereby designed to be introduced into a human or animal blood circuit so as to establish an extracorporeal blood circuit, whereby the supply line B1 can to that end be connected to a first blood vessel of the patient or animal to be treated, in particular a vein or an artery, for withdrawing a bloodstream to be treated and the return line B2 connected to the first blood vessel or a second blood vessel, in particular a vein, for returning a treated bloodstream into the intracorporeal blood circuit of the patient/animal.

To create the extracorporeal blood circuit, in particular to connect to the intracorporeal blood circuit of the patient or animal to be treated, the system can preferably be connected to a double lumen cannula which allows a veno-venous extracorporeal blood circuit to be established with only one vascular access. This thus results in extremely low stress on the patient or animal to be treated since two separate inlets into two separate vessels do not need to be positioned. Furthermore, the risk of infection is reduced.

According to the present disclosure, the three blood treatment apparatus A, D and G are thereby connected in series; i.e. sequentially, relative to a direction of blood flow of a bloodstream flowing through the system B100, as symbolized by the arrows in FIG. 4. The individual blood treatment apparatus A, D and G are thereby part of a common treatment apparatus according to the present disclosure and accommodated by a common base, in particular secured to a common carrier, wherein the individual components of the system B100 are connected to one another by corresponding hoses so as to be able to be flowed through sequentially; i.e. successively.

The herein disclosed series connection of an adsorber apparatus A, a dialysis apparatus D as well as a gas exchange apparatus G enables a combined blood treatment, in particular the combination of an adsorption treatment, in the present case the combination of sepsis therapy with dialysis therapy as well as the removal of $CO_2$ from the blood in one single common extracorporeal blood circuit. This can thereby avoid having to create a plurality of extracorporeal circuits for blood treatment and having to position a corresponding plurality of inlets in a patient or animal to be treated. A system B100 according to the present disclosure thus enables simultaneous blood treatment by means of adsorption, dialysis and gas exchange with the volume of blood of only one extracorporeal blood circuit.

The adsorber apparatus A in this exemplary embodiment of a herein disclosed system B100 is designed for sepsis therapy. Adsorber apparatus as such for this purpose are known in principle from the prior art. Since portions of the volume are taken from the blood mass flow during the blood treatment using the adsorber apparatus A, a further, in particular fourth, inlet 4 is connected downstream of the adsorber apparatus A in the blood flow direction to supply a substitute to compensate for this loss in volume, whereby in particular a liquid substitute, particularly an electrolyte solution, can be supplied.

In the herein disclosed system B100 depicted in FIG. 4, the dialysis apparatus D comprises a dialyzer for hemodialysis to which a dialysate or dialysis fluid respectively can be supplied via a fifth inlet B6 and effluent developing during the dialysis treatment can be discharged via a second outlet B5. Dialysis apparatus of this type are likewise generally known from the prior art.

The gas exchange apparatus G is depicted schematically in the herein disclosed system B100 shown in FIG. 4 as an apparatus having a first delimited region for receiving extracorporeal blood and a second delimited region for receiving the buffer solution described herein. The first and the second region adjoin one another in a contact zone and are only separated from each other by a membrane via which gas exchange can take place between the blood and the herein disclosed buffer solution. The herein disclosed buffer solution described in the present application can be an elimination medium component of the gas exchange apparatus for the extracorporeal reduction of the carbon dioxide content in the blood.

In a specifically designed embodiment of the herein disclosed apparatus, the gas exchanger G of the system 100 has a first delimited region for receiving the extracorporeal blood, an inlet port and an outlet port for the blood, and is designed such that the blood can flow through the region from the inlet port to the outlet port in a first direction of flow. The second delimited region for receiving the buffer solution has in this embodiment an inlet port B8 and an outlet port B7 for the buffer solution and is designed such that the buffer solution can flow through the region from the inlet port to the outlet port in a second direction of flow.

In order to convey the bloodstream to be treated through the system B100, a first pump P1 designed as a blood pump is provided, whereby the first blood pump P1 can be actuated to control and/or regulate the bloodstream by means of a control device (not shown here) which is likewise part of the herein disclosed system B100.

The first blood pump P1 can thereby be a peristaltic pump. In a particularly preferential embodiment, the herein disclosed system has a centrifugal pump as the first pump. This can be a diagonal pump designed as a rotor pump, preferably as described in DE 10 2010 024 650 A1. The size of the blood pump P1, in particular its connection cross-sections, is selected based on the volume of blood of the patient or animal to be treated.

In order to be able to establish an optimum blood flow for optimum treatment success at least at one of the three blood treatment apparatus A, D and/or G as well as for monitoring purposes, the system comprises a plurality of pressure sensor devices (not shown here), wherein a corresponding pressure sensor device is arranged immediately before and immediately after a blood treatment apparatus A, D or G in this exemplary embodiment of a herein disclosed system B100.

This enables determining a respective resulting pressure gradient across the associated blood treatment apparatus A, D or G. Said device can aid in deducing the state of the respective blood treatment apparatus A, D or G. In particular, the determined pressure gradient allows a conclusion to be drawn as to the extent to which the respective blood treatment apparatus A, D or G is affected by clotting.

Furthermore, a given transmembrane pressure in the respective blood treatment apparatus A, D and/or G can be determined in this way. Since the efficiency of the respective blood treatment basically depends on the respectively applied transmembrane pressure and same should be within a specific range for optimum treatment success depending on the respective blood treatment apparatus, it is in this way possible to set the blood flow at least for at least one of the three blood treatment apparatus A, D and G such that an advantageous transmembrane pressure is in each case established, in particular by a corresponding actuation of the blood pump P1.

The herein disclosed system B100 depicted in FIG. 4 further comprises a gas bubble detection device B14 arranged downstream of the three blood treatment apparatus A, D and G in the direction of blood flow for detecting a gas bubble in the bloodstream as well as a non-return valve B3 arranged downstream of the gas bubble detection device B14 in the return line 2. Should the gas bubble detection device 14 detect a gas bubble in the bloodstream, the non-return valve B3 is closed, the first blood pump P1 switched off and an alarm triggered. This can thereby prevent the gas bubble from being returned to the intracorporeal blood circuit of the patient or animal along with the bloodstream and resulting there in a life-threatening condition or even death.

The herein disclosed system B100 described here is thereby designed for a bloodstream ranging from 0.05 to 5l per minute, particularly for a bloodstream ranging from 0.1 to 3l, in particular ranging from 0.2 to 1l per minute, particularly for a range of from 0.2 to 0.5l per minute.

In order to avoid complications, the surfaces of the lumina of the system B100 which come into contact with the bloodstream can be provided with a biocompatible and at least partially with at least one functional coating, particularly with an antibacterial, anticoagulant and/or anti-inflammatory coating.

In the first exemplary embodiment of a herein disclosed system 100 for extracorporeal blood treatment depicted in FIG. 4, the adsorber apparatus A is arranged ahead of the dialysis apparatus D in the direction of blood flow, wherein the dialysis apparatus D is in turn arranged ahead of the gas exchange apparatus G in the blood flow direction. This arrangement has the advantage of an undiluted bloodstream being able to be supplied to the adsorber apparatus A, thereby being able to ensure the adsorption treatment's high effectiveness. Furthermore, an undesired non-specific binding of ions or pH shifts can occur in the adsorber apparatus A which can be compensated for by the dialysis treatment of the dialysis apparatus D performed downstream in the bloodstream given a sequence of individual blood treatment apparatus A, D and G as depicted in FIG. 4.

Furthermore, this arrangement of dialysis apparatus D after the adsorber apparatus A in the blood flow direction can act as a further safety system against an undesired intrusion of particles from the adsorber apparatus A arranged upstream.

The arrangement of the gas exchange apparatus G after the adsorber apparatus A in the blood flow direction has the advantage of the gas exchange apparatus G being able to compensate for carbon dioxide ($CO_2$) accumulating in the bloodstream from the supplying of the substitute after the adsorber apparatus A (which in the exemplary example shown in FIG. 4 can ensue via the fourth inlet B4 after the adsorber apparatus and ahead of the dialysis apparatus) as well as from a potentially carbon-laden ($CO_2$) dialysis fluid (which can be supplied to the system B100 in this exemplary example via the fifth inlet B6) prior to the treated bloodstream being returned to the intracorporeal blood circuit of the patient or animal respectively.

If the dialysis apparatus D in a herein disclosed system for extracorporeal blood treatment in which the blood treatment apparatus are arranged as described as per FIG. 4 is designed for hemodiafiltration instead of hemodialysis, a substitute, in particular an additional amount of substitute, can preferably also be supplied to the bloodstream via inlet B4 to compensate for the loss of fluid in the dialysis apparatus D. Alternatively or additionally, the system can also comprise a further inlet after the dialysis apparatus D in the blood flow direction for adding the substitute to compensate for the loss in fluid and/or volume in the adsorber apparatus A and/or the dialysis apparatus D.

In order to enable flexible adaptation of the herein disclosed system B100 to the respectively required blood treatment, the individual blood treatment apparatus A, D and G of the herein disclosed system 100 each have replaceable treatment modules, each comprising the entire treatment section and being able to be easily exchanged as a replacement part. The herein disclosed system B100 can in this way be easily and quickly adapted to the respective treatment required. Thus, for example, the adsorber apparatus A can be quickly and easily reconfigured from, for example, an adsorber apparatus A for endotoxin adsorption into an adsorber apparatus A for cytokine adsorption, for which specifically designed adsorber treatment modules are required depending on application.

Correspondingly, by changing the respective dialysis treatment module, the dialysis apparatus D of the herein disclosed system B100 can be reconfigured from a dialysis apparatus D designed for hemodialysis into a dialysis apparatus D designed for hemofiltration or hemodiafiltration.

The gas exchange apparatus G of the herein disclosed system B100 can also be adapted in the same way, wherein depending on the required treatment, a gas exchange treatment module designed to remove $CO_2$ from the bloodstream can be used.

Preferably, the individual inlets and outlets can likewise be adapted and/or reconfigured, particularly with regard to their arrangement within the system, in particular relative their arrangement before and/or after the respective blood treatment apparatus.

The system B100 can thereby be specifically configured for each treatment. Furthermore, the individual treatment modules can be replaced quickly and easily when clotting or the like occurs. In addition, the provision of a sterile system B100 for blood treatment can in this way be ensured in a particularly simple manner since all the components which come into contact with the bloodstream, in particular the respective blood treatment modules and their hose fittings, can be easily replaced prior to the start of treatment on a new patient or new animal respectively.

FIG. 5 shows a second exemplary embodiment of an herein disclosed system B200 for extracorporeal blood treatment, whereby components having the same functionality have the same reference numerals.

The structure of the second exemplary embodiment of a second system B200 for extracorporeal blood treatment likewise shown only schematically in FIG. 5 is principally similar to the first exemplary embodiment of a system 100 for extracorporeal blood treatment described as per FIG. 4, although differs from the system B100 described with reference to FIG. 4 in that the sequence of the three blood treatment apparatus A, D and G in the system B200 depicted in FIG. 5 is different and moreover that the dialysis apparatus D is not designed for hemodialysis, and thus does not have a dialyzer, but rather only for hemofiltration and thus has a hemofilter.

For this reason, the system B200 does not have a fifth inlet B6 for supplying a dialysate since hemofiltration does not require the supply of an additional dialysis fluid and only one resultant effluent from hemofiltration is to be discharged, which can likewise be discharged via the second outlet B5 in the system depicted in FIG. 5.

The embodiment of a system B200 for extracorporeal blood treatment depicted in FIG. 5, in which the dialysis apparatus D is arranged ahead of the adsorber apparatus A in the direction of blood flow and thus the bloodstream to be treated flows through the dialysis apparatus D prior to the adsorber apparatus A, has the advantage of the bloodstream being concentrated by the removal of the filtration volume (effluent) in the hemofilter of the dialysis apparatus D and thus a more concentrated bloodstream being able to be supplied to the adsorber apparatus A compared to the system B100 from FIG. 4. A higher effectiveness of the adsorption treatment can thereby be achieved. Consequently, improved adsorption treatment can be achieved with the system B200 depicted in FIG. 5.

The downstream arrangement of the gas exchange apparatus G in the blood flow direction can also compensate for an undesired loading or respectively enriching of the blood mass flow with carbon dioxide (($CO_2$) as a result of the addition of a ($CO_2$)-laden substitute via the fourth inlet B4 prior to the return into the intracorporeal blood circuit of the patient or of the animal to be treated in the second exemplary embodiment of an system depicted in FIG. 5.

Due a more concentrated bloodstream being supplied to adsorber apparatus A, the risk of clotting may increase, particularly in adsorber apparatus A. However, clotting can be quickly and reliably detected by the respective pressure sensor devices provided immediately before and immediately after the three blood treatment apparatus A, D and G and, in particular, largely prevented by the additional addition of an anticoagulant into the bloodstream, for example by the addition of citrate via inlet B9 (see FIG. 7). Furthermore, should clotting occur, the respective adsorber apparatus A or respective blood treatment apparatus A, D and/or G affected by clotting or the respective treatment module of same forming a treatment section can be respectively replaced.

FIG. 6 shows a third exemplary embodiment of a system B300 for extracorporeal blood treatment, whereby this system B300 is of basically similar structure to the two previously described systems B100 and B200, although respectively differs from the two previously described exemplary embodiments of systems B100 and B200 for extracorporeal blood treatment in the sequential arrangement of the individual blood treatment apparatus A, G and D.

In the third exemplary embodiment of a system 300 for blood treatment shown in FIG. 6, as in the system B100 depicted in FIG. 4, the blood mass flow to be treated likewise flows through the adsorber apparatus A first. Afterwards, however, the flow runs through the gas exchange apparatus G first and not until downstream thereof, the dialysis apparatus D.

Since the dialysis apparatus D in the exemplary embodiment of a system B300 depicted in FIG. 6 is likewise only designed for hemofiltration and not for hemodialysis, the bloodstream is now unable to become loaded past the gas exchange apparatus G because of an exchange with a $CO_2$-laden dialysate since no dialysate is supplied to said dialysis apparatus as it is not needed for hemofiltration.

The arrangement of the gas exchange apparatus G after the adsorber apparatus A ensures being able to compensate for a conceivable undesired $CO_2$ loading of the blood mass flow by the supplying of a $CO_2$-laden substitute via the fourth inlet B4. Here as well, with the arrangement of the dialysis apparatus D downstream of the adsorber apparatus A in the blood flow direction, the dialysis apparatus D can also act as a safety-related filtration stage relative to an undesired intrusion of particles into the adsorber apparatus A arranged upstream in the blood flow. Furthermore, undesired, non-specific additional ionic bonds and/or pH shifts potentially occurring in the adsorber apparatus A can also be compensated for by means of the dialysis apparatus D in this arrangement, or with this system B300 respectively. Moreover, the hemofilter downstream of the gas exchange apparatus G generates a back pressure in the gas exchanger G, which has an advantageous effect on the function of the gas exchanger G.

FIG. 7 shows a fourth exemplary embodiment of a system B400 for extracorporeal blood treatment, wherein this exemplary embodiment represents a particularly preferential embodiment of a system for extracorporeal blood treatment and is likewise based on the first exemplary embodiment of a system B100 as described with reference to FIG. 3. Additionally to the system B100 described as per FIG. 3, this system B400 comprises a second inlet B9 as well as a third inlet B11 via which a composition can in each case be supplied to the bloodstream.

A first composition, which is preferably accommodated in a bag B10, can thereby be supplied to the blood mass flow to be treated via the second inlet B9 with the aid of a second pump P2, wherein the system B400 is in this case designed such that the first composition can be supplied to the bloodstream immediately after it being drawn from the intracorporeal blood circuit of the patient to be treated or the animal to be treated, in particular still ahead of the first blood pump P1 in the blood flow direction and particularly ahead of the first blood treatment apparatus through which the bloodstream to be treated flows.

In particular, the system B400 is thereby designed to supply the bloodstream to be treated with a liquid citrate solution as an anticoagulant via the second inlet B9 with the aid of the second pump P2.

A second composition, in particular a calcium solution, can be supplied to the system via the third inlet B11 to compensate for the calcium loss occurring in the dialysis apparatus D during hemodialysis with the aid of a third pump P3. In this fourth exemplary embodiment of a system B400 for extracorporeal blood treatment depicted in FIG. 7, the second composition is thereby supplied via the third inlet B11 directly prior to the return of the treated bloodstream to the patient, in particular after the non-return valve B3. It is of course also possible for the third inlet to be arranged ahead of the non-return valve B3 in the blood flow direction.

The system B400 depicted in FIG. 7 is particularly suitable for an extracorporeal blood circuit treatment which has a veno-venous access; i.e. in particular for CVVHD, in which the bloodstream to be treated is taken from a vein of the patient or animal to be treated and the treated bloodstream is returned to a vein.

If the dialysis apparatus D in a system for extracorporeal blood treatment in which the blood treatment apparatus are arranged as described as per FIG. 7 is designed for hemodiafiltration instead of hemodialysis, a substitute can preferentially be supplied to the bloodstream preferably via an additional inlet B4 after the adsorber apparatus A and ahead of the dialysis apparatus D in the blood flow direction in order to compensate for the loss of fluid in the adsorber apparatus A and/or dialysis apparatus D. Alternatively or additionally, the system can also comprise an inlet B4 after the dialysis apparatus D in the blood flow direction for adding the substitute to compensate for the loss in fluid and/or volume in the adsorber apparatus A and/or dialysis apparatus D. Such a system is particularly suitable for post-CVVHDF.

FIG. 8 shows a fifth exemplary embodiment of a system B500 for extracorporeal blood treatment which is likewise based on the system B100 depicted in FIG. 4, although differs from the system B100 from FIG. 4 in that the adsorber apparatus A is arranged after the gas exchange apparatus G, particular after the gas exchange apparatus G and after the dialysis apparatus D. This arrangement has the advantage that, due to the resulting increased back pressure at the adsorber apparatus A, the pressure gradient in the gas exchange apparatus G on the gas exchange membrane rises, whereby improved gas exchange can be achieved.

FIG. 8 illustrates the substitute for compensating the volume loss in the adsorber apparatus A is thereby preferably added to the bloodstream ahead of the gas exchange apparatus G via inlet B4. Alternatively or additionally, adding it ahead of the dialysis apparatus D is also advantageously possible. The subsequently arranged gas exchange apparatus G can thereby compensate for an undesired $CO_2$ loading by the substitute.

FIG. 9 shows a sixth exemplary embodiment of a system B600 for extracorporeal blood treatment which is based on the system B500 depicted in FIG. 8, although differs from the system B500 from FIG. 8 in that the gas exchange apparatus G in this case is arranged ahead of the adsorber apparatus D, which in this case is only designed for hemofiltration and not for hemodialysis.

This arrangement has the advantage of the back pressure ahead of the dialysis apparatus D and ahead of the adsorber apparatus A having a respective increasing effect on the pressure gradient within the gas exchange apparatus G on the gas exchange membrane, whereby the efficiency of the gas exchange can be increased.

Preferably, the substitute to compensate for the loss of volume in the adsorber apparatus A is likewise added to the bloodstream ahead of the gas exchange apparatus G via inlet B4 so that an undesired $CO_2$ loading by the substitute can be compensated for by means of the subsequently arranged gas exchange apparatus G.

Due to the dialysis apparatus D being designed for hemofiltration, which does not require a dialysate, an undesired $CO_2$ loading by the substitute can be prevented.

FIG. 10 shows a seventh exemplary embodiment of a system B700 for extracorporeal blood treatment which is likewise based on the system B100 depicted in FIG. 4, however with a bypass device B13 having a bypass line B13A as well as a bypass valve B13B being additionally provided which enables the bloodstream to be treated to bypass the adsorber apparatus A. The system B700 has the advantage of blood treatment being possible both with or without adsorption treatment. As a result, the flexibility in terms of the possible applications of a herein disclosed system is significantly increased since an adsorption treatment is not indicated in all blood treatment cases or a clotted or an almost fully loaded or saturated adsorber can be circumvented.

The bypass valve B13B is thereby preferably designed such that a bloodstream to be treated is in each case either entirely conducted through the adsorber apparatus downstream of the bypass valve B13B in the direction of blood flow or completely bypasses the adsorber apparatus A via bypass line B13A.

In a particularly advantageous embodiment of a herein disclosed system, the system comprises an appropriately designed bypass device for each of the blood treatment devices A, D, G so that an adsorption treatment and/or a gas exchange and/or a dialysis treatment are all alternatively possible with a system according As herein disclosed FIG. 11 shows an eighth exemplary embodiment of a herein disclosed system B800 which is based on the system B100 from FIG. 4, whereby in this exemplary embodiment, instead of an adsorber apparatus A, the first blood treatment apparatus is a plasma separation apparatus PT in the form of a plasma filter PT by means of which separated blood plasma can be fed with the aid of a further, in particular third, pump P3 to a blood plasma disposal container W via a line B16 forming a fourth outlet for the removal of separated blood plasma.

Fresh plasma can be supplied to the bloodstream as a replacement for the amount of discharged blood plasma via a line B17 which forms a seventh inlet B17, in particular with the aid of a further, in particular fourth pump P4.

FIG. 12 shows a ninth exemplary embodiment of a system B900 which is based on the system B800 from FIG. 11, whereby in this exemplary embodiment, the separated plasma is not fed to a blood plasma disposal container W but rather is passed through a blood treatment apparatus in the form of an adsorber apparatus A by means of a hose line, in particular by means of a bypass line, wherein the treated plasma is returned to the rest of the bloodstream after the adsorption treatment, in particular into the main line.

FIG. 13 shows a tenth exemplary embodiment of a system B1000 which is based on the system B900 from FIG. 12, whereby in this exemplary embodiment, the separated plasma is not supplied to the rest of the bloodstream after the adsorption treatment but rather to the plasma separation apparatus PT for recirculation in a bypass circuit. Improved plasma separation and/or adsorption treatment can thereby be achieved.

REFERENCE NUMERAL LIST FOR FIGS. 4 TO 13

B100, B200, B300, system for extracorporeal blood treatment
B400, B500, B600,
B700, B800, B900,
B1000
B1 supply line (first inlet)
B2 return line (first outlet)
B3 non-return valve
B4 fourth inlet for supplying a substitute to the bloodstream
B5 second outlet for removing an effluent from the dialysis apparatus
B6 fifth inlet for supplying a dialysate to the dialysis apparatus
B7 third outlet for removing a $CO_2$-laden buffer solution from the gas exchange apparatus
B8 sixth inlet for supplying a herein disclosed buffer solution for reducing the $CO_2$ content in blood to the gas exchange apparatus
B9 second inlet for supplying a first composition to the bloodstream
B10 bag, filled with a first composition
B11 third inlet for supplying a second composition to the bloodstream
B12 bag, filled with a second composition
B13 bypass device
13A bypass line
13B bypass valve
14 gas bubble detection device
15 bag, filled with fresh blood plasma
16 fourth outlet for removing separated blood plasma
17 seventh inlet for the supplying of fresh blood plasma
A adsorber apparatus
D dialysis apparatus
G gas exchange apparatus
PT plasma separation apparatus
P1 first pump, blood pump
P2 second pump
P3 third pump
P4 fourth pump
P5 fifth pump
W blood plasma disposal container In a second aspect, the subject of the present disclosure is characterized by the features of the following embodiments 20 to 37:

Embodiment 20

A system (B100, B200, B300, B400, B500, B600, B700, B800, B900, B1000) for extracorporeal blood treatment, wherein the system (B100, B200, B300, B400, B500, B600, B700, B800, B900, B1000) comprises
a first inlet (B1) for introducing a bloodstream to be treated into the system (B100, B200, B300, B400, B500, B600, B700, B800, B900, B1000),
at least one first blood treatment apparatus (A, PT),
a second treatment apparatus (D),
a third blood treatment apparatus (G), and
a first outlet (B2) for extracting a treated bloodstream from the system (B100, B200, B300, B400, B500, B600, B700, B800, B900, B1000),
wherein the first blood treatment apparatus (A, PT) is or comprises an adsorber apparatus (A) for removing at least one exogenous and/or at least one endogenous pathogen and/or a plasma separation apparatus (PT) for separating blood plasma from the other blood components,
wherein the second blood treatment apparatus (D) is designed as a dialysis apparatus (D), in particular as a dialysis apparatus (D) for renal replacement therapy, and wherein the third blood treatment apparatus (G) is a gas exchange apparatus designed as an apparatus (10) for the extracorporeal reduction of carbon dioxide content in blood as described herein, in particular as a gas exchange apparatus (G) for at least partially removing CO2 from a bloodstream flowing through the first delimited region of the gas exchange apparatus (G) and a buffer solution according to the features as described herein, flowing through the second delimited region of the gas exchange apparatus, and
wherein the three blood treatment apparatus (A and/or PT, D, G) are sequentially connected in series between the first inlet (B1) and the first outlet (B2) of the system with respect to the blood flow direction of a bloodstream to be treated in a functional application state of the system (B100, B200, B300, B400, B500, B600, B700, B800, B900, B1000) and a bloodstream to be treated flows extracorporeally through same in succession.

Embodiment 21

The system (B100, B200, B300, B400, B500, B600, B700, B800, B900, B1000) as described herein, characterized in that the first blood treatment apparatus (A) is or comprises an adsorber apparatus (A) designed for endotoxin adsorption, cytokine adsorption and/or immunoadsorption, wherein the adsorber apparatus (A) is in particular designed to remove at least one pharmaceutical and/or pharmaceutical substance and/or at least one plant toxin and/or at least one organic toxin and/or at least one other toxic substance and/or to remove bacteria, viruses, fungi and/or other organisms and/or at least one immunocomplex and/or at least one immunoglobulin and/or at least one inflammatory response substance of the body and/or antibodies and/or at least one pathogen-associated molecular pattern and/or at least one so-called alarmin.

Embodiment 22

The system (B100, B200, B300, B400, B500, B600, B700, B800, B900, B1000) as described herein, characterized in that the system (B100, B200, B300, B400, B500, B600, B700, B800, B900, B1000) comprises at least one first pump (P1), in particular a pump (P1) designed as a blood pump, for conveying at least a portion of a bloodstream to be treated, wherein the first pump (P1) is preferably arranged between the first inlet (1) and the first of the three blood treatment apparatus (A, PT, D, G) in the direction of blood flow and is in particular designed to convey the entire bloodstream to be treated.

Embodiment 23

The system (B400) as described herein, characterized in that the system (B400) comprises a further, in particular second inlet (B9) for the addition of a first composition into the bloodstream, in particular into the bloodstream to be treated, wherein this further inlet (B9) is preferably arranged in the blood flow direction such that the composition is able to be supplied to the bloodstream ahead of the first pump (P1) and/or ahead of the first of the three blood treatment apparatus (A, PT, D, G) in the direction of blood flow.

Embodiment 24

The system (B400) as described herein, characterized in that the system (B400) comprises a further, in particular third inlet (B11) for adding a second composition into the bloodstream, in particular the treated bloodstream, wherein this further inlet (B11) is preferably arranged in the blood flow direction such that the composition is able to be supplied to the bloodstream after the dialysis apparatus (D), in particular after the last blood treatment apparatus (A, PT, D, G), in the direction of blood flow.

Embodiment 25

The system (B100, B200, B300, B400, B700, B800, B900, B1000) as described herein, characterized in that the adsorber apparatus (A) and/or the plasma separation apparatus (PT) is/are arranged ahead of the gas exchange apparatus (G) in the direction of blood flow.

Embodiment 26

The system (B500, B600) as described herein, characterized in that the adsorber apparatus (A) and/or the plasma separation apparatus (PT) is arranged after the gas exchange apparatus (G) in the direction of blood flow.

Embodiment 27

The system (B100, B400, B700, B800, B900, B1000) as described herein, characterized in that the adsorber apparatus (A) and/or the plasma separation apparatus (PT) is/are arranged ahead of the dialysis apparatus (D) in the direction of blood flow, wherein the dialysis apparatus (D) is preferably designed for hemodialysis and in particular comprises a dialyzer.

Embodiment 28

The system (B200, B500, B600) as described herein, characterized in that the adsorber apparatus (A) and/or the plasma separation apparatus (PT) is/are arranged after the dialysis apparatus (D) in the direction of blood flow, wherein the dialysis apparatus (D) is preferably designed for hemofiltration and in particular comprises a hemofilter.

Embodiment 29

The system (B100, B200, B400, B500, B800, B900, B1000) as described herein, characterized in that the dialysis apparatus (D) is arranged ahead of the gas exchange apparatus (G) in the direction of blood flow.

Embodiment 30

The system (B300, B600, B700) as described herein, characterized in that the dialysis apparatus (D) is arranged after the gas exchange apparatus (G) in the direction of blood flow, wherein the dialysis apparatus (D) is preferably designed for hemofiltration and comprises a hemofilter.

Embodiment 31

The system (B100, B200, B300, B400, B500, B600, B700, B800, B900, B1000) as described herein, characterized in that the system (B100, B200, B300, B400, B500, B600, B700, B800, B900, B1000) comprises at least one pressure sensor device for determining a flow pressure of the bloodstream at a defined point in the system (B100, B200, B300, B400, B500, B600, B700, B800, B900, B1000), wherein at least one pressure sensor device is preferably arranged directly in front of and/or directly after at least one treatment section of a blood treatment apparatus (A, PT, D, G) in the direction of blood flow.

Embodiment 32

The system (B100, B200, B300, B400, B500, B600, B700, B800, B900, B1000) as described herein, characterized in that the system (B100, B200, B300, B400, B500, B600, B700, B800, B900, B1000) comprises at least one gas bubble detection device (B14) for detecting a gas bubble in the bloodstream.

Embodiment 33

The system (B100, B200, B300, B400, B500, B600, B700, B800, B900, B1000) as described herein, characterized in that a treatment section of at least one blood treatment apparatus (A, PT, D, G) is at least partially, preferably entirely, formed by an exchangeable treatment module, in particular by a cartridge-like treatment module.

Embodiment 34

The system (B700) as described herein, characterized in that the system (B700) comprises at least one switchable bypass device (B13) for bypassing at least one blood treatment apparatus (A, D, G).

Embodiment 35

The system (B100, B200, B300, B400, B500, B600, B700, B800, B900, B1000) as described herein, characterized in that at least one component of the system (B100, B200, B300, B400, B500, B600, B700, B800, B900, B1000) comprises a biocompatible and preferably functional coating on a surface coming into contact with the bloodstream to be treated, in particular an antibacterial, anticoagulant and/or anti-inflammatory coating.

Embodiment 36

A treatment apparatus for extracorporeal blood treatment, characterized in that the treatment apparatus comprises a system (B100, B200, B300, B400, B500, B600, B700, B800, B900, B1000) designed as described herein, wherein the first, the second and the third blood treatment apparatus (A, PT, D, G) of the system (B100, B200, B300, B400, B500, B600, B700, B800, B900, B1000) are in particular arranged in a common housing and/or are accommodated by a common base.

Embodiment 37

A kit for extracorporeal blood treatment, wherein the kit comprises as components at least
one first blood treatment apparatus (A, PT),
a second blood treatment apparatus (D),
a third blood treatment apparatus (G), and
a tubing set having a first inlet (1) for introducing a bloodstream to be treated and a first outlet (2) for discharging a treated bloodstream via one or more tubes as well as
in particular an installation and/or operating manual,
wherein the first blood treatment apparatus (A, PT) is or comprises an adsorber apparatus (A) for removing at least one exogenous and/or at least one endogenous pathogen and/or a plasma separation apparatus (PT) for separating blood plasma from the other blood components,
wherein the second blood treatment apparatus (D) is designed as a dialysis apparatus (D), in particular as a dialysis apparatus (D) for renal replacement therapy, and
wherein the third blood treatment apparatus (G) is designed as an apparatus for the extracorporeal reduction of the carbon dioxide in blood (A10) as described herein, in particular as a gas exchange apparatus (G) for the at least partial removal of carbon dioxide from a bloodstream flowing through the gas exchange apparatus (G) with a buffer solution as described herein,
characterized in that the components of the kit can be connected to a system (B100, B200, B300, B400, B500, B600, B700, B800, B900, B1000) for extracorporeal blood treatment designed as described herein, in particular according to the installation and/or operating manual.

In a third aspect, the present disclosure relates to a functional unit for performing an extracorporeal blood treatment, a blood-guiding apparatus for interacting with the functional unit for performing extracorporeal blood treatment which comprises a blood treatment element, wherein the blood treatment element is an apparatus for the extracorporeal reduction of the carbon dioxide content in blood according to one embodiment pursuant to the first aspect of the present disclosure, as well as an arrangement comprising a functional unit for extracorporeal blood treatment and a blood-guiding apparatus, in each case for use with a buffer solution according to the first aspect of the present disclosure.

Consolidating different therapies into one single therapy which is for example able to be performed using a single medical treatment apparatus or a single medical treatment system respectively is known in the field of extracorporeal blood treatment. In other words, at least two separate blood treatment elements in one common extracorporeal blood circuit thereby have an effect on the drawn blood, preferably in different ways. Such therapy is referred to as combination therapy. Normally, therapies having causally related medical indications and which therefore frequently present together are combined. the combining of therapies for differing indications is also appropriate when the treatment technique warrants such a combination due to advantageous synergies.

Thus, in the field of extracorporeal blood treatments, for example, renal replacement therapies are combined with other extracorporeal blood therapies. For example, treatments for acute dialysis (CRRT) such as, for instance, hemodialysis (HD), hemodiafiltration (HDF), hemofiltration (HF), hemoperfusion (HP) or ISO-UF are used in combination with extracorporeal membrane oxygenation or $CO_2$ removal treatments respectively in one common extracorporeal blood circuit. Normally, a dialyzer and a blood treatment element for a further extracorporeal blood treatment such as e.g. a gas exchanger are arranged in series in a common extracorporeal blood circuit to that end.

Further known is that as flow rate increases, effectiveness of the gas exchange increases, in particular for the removal of $CO_2$ from the blood or for $O_2$ enrichment of the blood.

The inventor has recognized that the forced flow rate coupling in both the dialyzer and the gas exchanger due to the serial arrangement of the two components, regardless of their sequential arrangement, is problematic to operating the treatment apparatus with an effective gas exchange. For example, the flow rates used in continuous acute dialysis (CRRT) treatment methods do not typically exceed 200-300 ml/min. In contrast, the efficiency of the cited lung assist therapies is heavily dependent on blood flow. When reducing the carbon dioxide content of blood in an extracorporeal blood circuit, a blood flow of at least 500 ml/min is provided from a medical point of view. A combination of these kidney replacement and lung assist therapies in terms of $CO_2$ reduction in blood is thus always associated in the prior art with one of the underlying indications being treated at reduced efficiency.

It is presently a task to overcome the aforementioned disadvantages and enable an extracorporeal blood treatment using a combination of a dialyzer and a further blood treatment element for reducing the carbon dioxide content in blood (combination therapy) in the optimal efficiency range for each part of the therapy.

The invention solves this task by means of embodiments 38, 44, and 50. Advantageous embodiments of the invention are represented by the embodiments 39 to 43 and 45 to 49.

The functional unit according to the present disclosure for performing an extracorporeal blood treatment in which the blood is guided in a blood-guiding apparatus having a main blood line and at least one secondary line fluidly connected to the main blood line and wherein the main blood line comprises a dialyzer as well as a blood treatment element downstream of the dialyzer, wherein the blood treatment element (C103) is an apparatus for extracorporeally reducing the carbon dioxide content in the blood (C10) in accordance with one of the embodiments 8 to 19, comprises a control apparatus and a pump assembly configured to generate blood flows in the main blood line as well as in the at least one secondary line, wherein the control apparatus is configured to operate the pump assembly such that a first blood flow rate in the dialyzer (dialyzer flow rate) is decoupled from a second blood flow rate in the blood treatment element.

In the context of the present application, a "blood treatment element" or a "gas exchange" is understood as an apparatus for the extracorporeal reduction of the carbon dioxide content in blood according to the first aspect of the present disclosure, in particular as is defined in the embodiments 8 to 19. The apparatus for the extracorporeal reduction of the carbon dioxide content is characterized in that it is operated with the buffer solution according to the first aspect of the present disclosure, in particular as is defined by the features of at least one of the forms of use 1 to 6. Accordingly, the blood treatment element has a first delimited region for receiving extracorporeal blood and a second delimited region for receiving the herein disclosed buffer solution according to the first aspect of the present disclosure, wherein the first and second region adjoining each other in a contact zone are only separated from one another by a membrane via which gas exchange can occur between the blood and the buffer solution.

The herein disclosed blood-guiding apparatus for interacting with an herein disclosed functional unit for performing an extracorporeal blood treatment comprises a main blood line for fluidic connection to a dialyzer as well as fluidic connection to a blood treatment element downstream of the dialyzer, wherein the main blood line has a blood sampling port for connecting to a patient's blood sampling access at one end and a blood return port for connecting to a patient's blood return access at another end; at least one secondary line which leads away from the main blood line at a first branching point and reunites with the main blood line at a second branching point; and one or more pump assembly sections, designed to act on the pump assembly of the blood treatment apparatus.

The herein disclosed arrangement for blood treatment comprises a functional unit for performing extracorporeal blood treatment and an herein disclosed blood-guiding apparatus.

In other words, the herein disclosed functional unit for performing an extracorporeal blood treatment, the herein disclosed blood-guiding apparatus as well as the herein disclosed arrangement for blood treatment allow an extracorporeal blood treatment to be conducted using a common extracorporeal blood circuit having a series connection of dialyzer and treatment element for reducing carbon dioxide content in blood arranged downstream of the dialyzer with an eye to improving the efficiency of the treatment. A higher blood flow than for the dialyzer therapy thereby makes sense for the further extracorporeal blood treatment.

The blood treatment element for the further extracorporeal treatment is a gas exchanger for removing $CO_2$.

Within the meaning of the present description, "therapy" can encompass not only healing but also at least alleviation, symptomatic therapy, delay, dehabituation and diagnosis. In particular, blood therapy can be understood as any effect on the blood or change in the blood such as adding substances to the blood or extracting substances from the blood which is able to induce one of the above-cited or a corresponding effect.

The use of a common extracorporeal blood circuit for both treatments in the sense of a combination therapy is desirable as the invasive steps of drawing the blood as well as returning the blood thereby only need to be done once for both therapies and the patient is thus also only subjected to the accompanying treatment risks once.

In the series arrangement of the dialyzer and the blood treatment element in an extracorporeal blood circuit, both sequential arrangements are in principle possible. If the blood flows through the gas exchanger first and then the dialyzer during $CO_2$ removal, after passing through the gas exchanger, blood already low in $CO_2$ may then be re-enriched with $CO_2$ in the dialyzer. This is caused by the concentration gradients across the dialyzer membrane since dialysis solutions usually contain bicarbonate in which $CO_2$ is buffered. If the blood does not pass through the gas exchanger until after the dialyzer, this reaccumulation does not occur.

The functional unit for performing extracorporeal blood treatment can constitute the reusable machine side of the blood treatment arrangement. The blood-guiding apparatus can constitute a blood tubing set or a cassette with blood lines or a combination of blood tubes and at least one cassette with blood lines for equipping the blood treatment apparatus.

The blood treatment apparatus can thereby be designed as a medical disposable to be discarded after each treatment for hygienic reasons. In particular, the blood-guiding apparatus can also comprise one or more further fluid guides in addition to the blood guide such as a dialysate circuit or lines for conducting a buffer solution for reducing the carbon dioxide content in blood as is described in the first aspect of the present disclosure, in particular as defined by the features of the forms of use 1 to 6, for operating a gas exchanger or blood treatment element as described above.

The main blood line of the blood-guiding apparatus can comprise the respectively suitable connectors or connections for connecting to the dialyzer and/or connecting to blood treatment element. The design of these connectors, in particular for connecting to the dialyzer, can include for example a cylindrical shape having an outer diameter in the range of from 10.5-12.8 mm as well as a conical fluid channel having an inner diameter of 6.33 mm at the distal end of the connector. However, further designs which meet the requirements for the intended flows are also conceivable in accordance with the knowledge of the person skilled in the art. Furthermore, the blood-guiding apparatus can also incorporate the dialyzer and/or the blood treatment element if they are securely attached to the main blood line, for example glued or fused.

The herein disclosed apparatus for blood treatment and for blood guidance can be provided so as to act together and can together form an herein disclosed arrangement for treating blood. The blood treatment arrangement can have further components in addition to the functional unit and the blood-guiding apparatus.

The functional unit and the blood-guiding apparatus can each comprise complementary components intended to interact. Thus, the functional unit has a pump assembly while the blood-guiding apparatus has one or more pump assembly sections designed to act on the pump assembly of the blood treatment apparatus.

Optionally, the functional unit can in some embodiments comprise one or more pressure sensors while the blood-guiding apparatus can in some embodiments optionally comprise one or more pressure measuring sections which can be designed to measure the pressure by means of the cited pressure sensors of the functional unit for measuring pressure. The pressure measuring section can be a flexible membrane or a lead able to transmit the pressure in the blood-guiding apparatus to the pressure sensor via a compressible gas column.

Furthermore, the functional unit can in some embodiments optionally comprise an infusion pump for supplying medical fluid or two infusion pumps for supplying medical fluid or three infusion pumps for supplying medical fluid or four or more infusion pumps for supplying medical fluid, while the main blood line of the blood-guiding apparatus can in some embodiments optionally comprise one or more addition ports for medical anti-coagulation liquid as well as one or more furthermore optional addition ports for dilution liquid.

An addition port can thereby be understood both as a normal connection or connector on the main blood line of the blood-guiding apparatus, e.g. of Luer Lock design, but also as a detachable or securely attached access line to the main blood line. The above-cited infusion pumps of the blood treatment apparatus can thereby be provided so as to have a pumping effect on the access lines connected to the addition ports. The access lines can thereby each be connected to fluid reservoirs with the fluid to be added for the conveyance of same into the main blood line by means of the infusion pumps.

In one embodiment, the inventor proposes branching the main blood line of the common extracorporeal blood circuit at a first branching point upstream of the dialyzer, guiding a secondary line around the dialyzer and not rejoining it to the main blood line again until a branching point downstream of the dialyzer and upstream of the gas exchanger. The inventor thereby arranges the dialyzer in the main blood line upstream of the gas exchanger. This can mean being able to avoid the previously described reaccumulation of $CO_2$.

Furthermore, a pump assembly equipped to generate blood flows in the main blood line as well as in the secondary line can be arranged on the extracorporeal blood circuit. The pump assembly can be connected to a control apparatus to that end. The control apparatus is configured to control the operation of the pump assembly by means of appropriate signals. In terms of the description as a whole, the term "control" also includes the feasibility of regulation as an alternative.

The control apparatus is configured to operate the pump assembly such that a first blood flow rate in the dialyzer is decoupled from a second blood flow rate in the blood treatment element. To hereby be understood by "decoupled" is any desired flow rates being able to be generated in the dialyzer and in the blood treatment element by means of the control without the specifying of one flow rate limiting the choice of the other flow rate.

In further embodiments, the pump assembly can be designed to generate mutually independent blood flow rates in the main blood line and in the secondary line. To hereby be understood by "independent" is that the specifying of one of the two flow rates has no effect on the pump assembly settings in selecting the other flow rate.

The person skilled in the art recognizes that the pump assembly can be realized in a variety of ways so as to act in the aforementioned manner.

In general, the pump assembly has at least two elements which act on the flow in the two line sections. At least one of these elements is thereby usually an active element able to induce the flow in a line element, for example a pump. The second of the at least two elements can likewise be an active element for generating a flow or can be a passive element, the effect of which can be the flow through the element being definable or adjustable. This second element can for example be a throttle or a valve.

For example, the pump assembly can consist of an occluding blood pump in the main blood line upstream of the first branching point and a further occluding blood pump downstream of the first branching point and upstream of the dialyzer. Further exemplary embodiments of the pump assembly are specified in the figures and in the description of the figures. In addition to the exemplary embodiments described, however, the present disclosure also encompasses all other pump assemblies which are capable of conducting blood through the main blood line and/or the at least one secondary line.

In further embodiments of the present disclosure, the pump assembly can further be equipped to generate a blood flow in a second secondary line. The control apparatus can in this case be configured to operate the pump assembly such that the blood flow rate in at least one section of the main blood line is independent from at least one of the blood flow rates in the secondary lines.

In a further embodiment, the main blood line of the common extracorporeal blood circuit branches at a first branching point downstream of the blood treatment element for the further extracorporeal blood treatment, a secondary line leads around the blood treatment element and rejoins the main blood line again upstream of the blood treatment element and downstream of the dialyzer. In this case, the pump assembly effects a recirculation of the blood flow via the blood treatment element with the blood flow in the secondary line. The blood flow rate in the blood treatment element increases in comparison to the blood flow rate in the dialyzer by the amount of blood flow in the secondary line, which leads to the decoupling of the two flows and thus to the solution of the task.

In the case of $CO_2$ removal, the extracorporeal blood is initially reduced primarily by the $CO_2$ freely available in the plasma when passing through the gas exchanger. Free $CO_2$ is then subsequently released again into the plasma from the natural $CO_2$ buffer system of the blood. The initial decrease in the partial pressure of the free $CO_2$ will thus be recompensated again after some time. The inventor has recognized that blood which has already been treated in the gas exchanger is thus open to retreatment after a short time and for this reason, the above-described recirculation through the gas exchanger can be worthwhile.

In further embodiments of the present disclosure, the blood can also be guided in two secondary lines, wherein the first secondary line is diverted away from the main blood line at a first branching point upstream of the dialyzer and reunites with the main blood line again at a second branching point downstream of the dialyzer and upstream of the treatment element. The second secondary line can be diverted away from the main blood line at a recirculation branching point downstream of the blood treatment element and empties into a recirculation return port. The recirculation return port can thereby be arranged in the main blood line upstream of the connection point for the blood treatment element and downstream of the connection point for the dialyzer. Furthermore, the recirculation return port can also be arranged in the first secondary line upstream of the second branching point. In these embodiments, the second secondary line can recirculate the blood through the blood treatment element for the further blood treatment therapy and thus contribute to increasing the efficiency of this part of the therapy. In these embodiments, the pump assembly can also be equipped to generate a blood flow in the second secondary line. Moreover, the control apparatus can be configured to operate the pump assembly such that the blood flow rate in at least one section of the main blood line is independent of at least one of the secondary line blood flow rates.

Measures can be taken in extracorporeal blood therapies to counteract a coagulation of the blood. To that end, the patient is periodically treated systemically with an anticoagulant substance, for example heparin, or local anticoagulation occurs in the extracorporeal blood circuit, for example by means of heparin or the addition of citrate and calcium (CiCa anticoagulation). Anticoagulant coatings of the blood-guiding components of the extracorporeal blood circuit are also common. The CiCa anticoagulation method has been established in the field of acute dialysis for years, the dosage has been optimized and intensively reviewed in long-term studies. Normally, the addition of citrate in the extracorporeal blood circuit upstream of the dialyzer lowers the coagulating effect of the blood by binding calcium ions in so-called citrate calcium chelates. When the blood is returned, some of these citrate calcium chelates are reinfused into the patient where the citrate portions are metabolized in the liver and the calcium released again. Another portion of the chelates is removed from the extracorporeal blood circuit via the dialyzer membrane and discarded.

Since the patient loses a significant amount of calcium as a result of this process, it can be replaced prior to the blood reinfusion by the artificial addition of calcium. The rate of the citrate addition is usually linked to the blood flow in order to provide adequate anticoagulation for the corresponding volume of blood which comes into contact with the components of the extracorporeal blood circuit. The rate of calcium addition can be selected such that the calcium losses via the dialyzer membrane are evenly compensated. It is thus dependent on the blood flow through the dialyzer but also on multiple other parameters such as, for example, the rate of citrate addition as well as treatment-specific properties such as, for example, the selection of dialyzer membrane and the respective prevailing transmembrane pressure among other things.

The concentration of calcium ions can therefore be regularly monitored by taking samples during the CiCa CRRT and the rate of addition can be adjusted accordingly. On the other hand, however, experiences from the above-cited studies, which were processed in standard CiCa dosing protocols available to users, can also be utilized. A control apparatus which controls a corresponding addition of the anticoagulant substance can be provided to that end. This control can ensue on the basis of e.g. at least one or more of the above-described calcium ion concentration, blood flow, dialyzer membrane, and transmembrane pressure variables and/or standard protocols stored in the apparatus.

Should a further extracorporeal blood treatment be added to a common extracorporeal blood circuit for acute dialysis, completely new boundary conditions relative to citrate and calcium dosing in the CiCa anticoagulation can result. In particular, the dosage protocols established in long-term study results cannot necessarily be adopted in a series connection of dialyzer and blood treatment element for the further extracorporeal therapy since neither the influence of the blood treatment element on inducements to coagulate nor any calcium losses beyond those known in the dialyzer are taken into account.

The herein disclosed line routing optionally provides for the arrangement of an addition port for the addition of a first medical fluid for anticoagulation, for example citrate, in a section of the main blood line upstream of the dialyzer, the entire blood flow of which will then also pass through the dialyzer. The known dosing protocols for CiCa anticoagulation can thus continue to be used despite the combination therapy since only coagulation by the dialyzer initially needs to be taken into account. The components of the blood treatment element can be anticoagulated by means of coating.

The line routing further optionally provides for the arrangement of an addition port for the addition of a second medical fluid for anticoagulation, for example calcium, in the main blood line downstream of the blood treatment element.

In further embodiments of the present disclosure in which the first branching point is arranged upstream of the dialyzer and the first addition port for the first medical fluid for anticoagulation is thus downstream of the first branching point, a further addition port for a third medical fluid for anticoagulation, for example citrate, can be arranged on the main blood line upstream of the first branching point. Additionally adding citrate through this line, preferably small amounts of citrate, can rapidly generate an increased anticoagulant effect when needed in the entire extracorporeal blood circuit. The additional addition via the addition port upstream of the first branching point preferably occurs for small amounts of citrate since the maximum tolerated amount of citrate is metabolically limited and the greater effect on the dialyzer, which is generally not coated with an anticoagulant, is needed. It is therefore not necessary to deviate from the known calcium dosing algorithm in this case, even if small amounts of citrate are additionally added through this line.

The first and/or second and/or third medical fluid for anticoagulation can in each case also be heparin or another medical fluid having anticoagulant effect.

Pump sections for infusion pumps can be arranged in individual or all of the above-cited addition ports, e.g. for calcium or citrate, via which the respective medical fluid to be added can be conveyed from a reservoir to the main blood line through the addition line. In the embodiments in which the same medical fluid is conveyed through several addition lines, particularly in the case of citrate, same can also be conveyed with a common pump and/or from a common reservoir.

As described above, the blood treatment apparatus can comprise a pressure sensor for determining the transmembrane pressure, in particular for measuring the pressure in the main blood line between the dialyzer and the blood treatment element, where in some embodiments of the blood-guiding apparatus, a corresponding pressure measuring section can be arranged for capturing the pressure via the pressure sensor.

As described above, the blood treatment apparatus can comprise a further pressure sensor for determining the transmembrane pressure, in particular for measuring the pressure in the main blood line between the first branching point and the dialyzer. A corresponding pressure measuring section can be arranged in the blood-guiding apparatus at the cited point for capturing the pressure via the pressure sensor.

Two or more pressure sensors can also be provided for measuring the pressure at both of the above-cited points or additionally at other points. This enables a particularly precise determination of the transmembrane pressure as well as a better monitoring of the treatment processes via the threshold windows of the respective pressure values.

To measure the transmembrane pressure, one or more pressure sensors can be arranged on the dialysate side. The pressure upstream and/or downstream of the dialyzer can thus be measurable on the dialysate side.

To also enable the combination therapy of renal replacement therapies with hemofiltration or hemodiafiltration processes, the blood-guiding apparatus can further optionally have one or more addition ports for a dilution liquid on the main blood line. The respective corresponding infusion pumps on the blood treatment apparatus side can convey the dilution liquid, for example a substitute solution or dialysis solution, into the main blood line through these addition ports. According to the present disclosure the dilution liquid may be stored in one or more reservoirs, e.g. disposable bags. Alternatively, the blood treatment apparatus can be equipped to produce the substitute solution or dialysis solution respectively. To that end, the blood treatment apparatus can comprise a water treatment apparatus having, for example, a degassing apparatus and concentrate ports for connecting concentrate sources. An addition port for a dilution liquid can be arranged on the main blood line upstream of the dialyzer for predilution. For postdilution, an addition port for a dilution liquid can be arranged on the main blood line downstream of the dialyzer and upstream of the blood treatment element. There is yet another postdilution possibility for the herein disclosed combination therapy with dialyzer and blood treatment element. An addition port for a dilution liquid for postdilution can also be arranged in the main blood line downstream of the blood treatment element. Introducing the substitute, which customarily contains calcium, downstream of the blood treatment element has the advantage of the anticoagulant effect of the citrate occurring in as many parts of the extracorporeal blood circuit as possible.

The user can also selectively connect substitute lines to one or more of the cited addition ports for the dilution liquid. The dilution liquid can also be pumped from a common reservoir and/or by a common infusion pump.

In a further embodiment of the present disclosure, the dialyzer can be arranged in the secondary line and the blood treatment element for reducing the carbon dioxide content can be arranged in the main line. It is thus likewise possible to decouple the bloodstreams flowing through the dialyzer and the blood treatment apparatus and to set significantly different flow rates. Accordingly, a bloodstream at a significantly lower flow rate than the blood in the main blood line can be guided by the secondary line via a branching point in the main blood line downstream of the blood treatment element. The blood can flow in the secondary line through the dialyzer and be treated under mass transfer and join the main blood line via a branching point upstream of the blood treatment element. The flow rate of the blood in the treatment element for reducing the carbon dioxide content in blood is thereby the sum of the flow rate of the blood withdrawn from the patient and the blood flow rate set in the secondary line.

The herein disclosed blood-guiding apparatus for interacting with a previously described functional unit is accordingly characterized by a main blood line for the fluidic connection to a blood treatment element, wherein the blood treatment element is an apparatus for extracorporeally reducing the carbon dioxide content in blood according to one of the embodiments 8 to 19 and a secondary blood line for the fluidic connection to a dialyzer, wherein the main blood line has a blood sampling port for the connection to a patient's blood sampling access at one end and a blood return port for the connection to a patient's blood return access at another end, wherein the secondary line (C130), leads away from the main blood line (C101) at a first branching point (C104), preferably downstream of the blood treatment element for reducing carbon dioxide content, and reunites with the main blood line (C101) again at a second branching point (C105), preferably upstream of the blood treatment element for reducing carbon dioxide content.

Furthermore, according to the present embodiment, addition ports for adding a first and/or second medical fluid for anticoagulation can also be arranged on the blood-guiding apparatus. Accordingly, an addition port for a first medical fluid for anticoagulation, e.g. a citrate solution, can be arranged in the secondary line (C130) upstream of the dialyzer. Furthermore, a further addition port (C111) for a second medical fluid for anticoagulation, e.g. a calcium solution, can be arranged in the main blood line downstream of the connection point for the treatment element.

Further description are made in greater detail on the basis of exemplary embodiments as well as figures.

Figure 14:
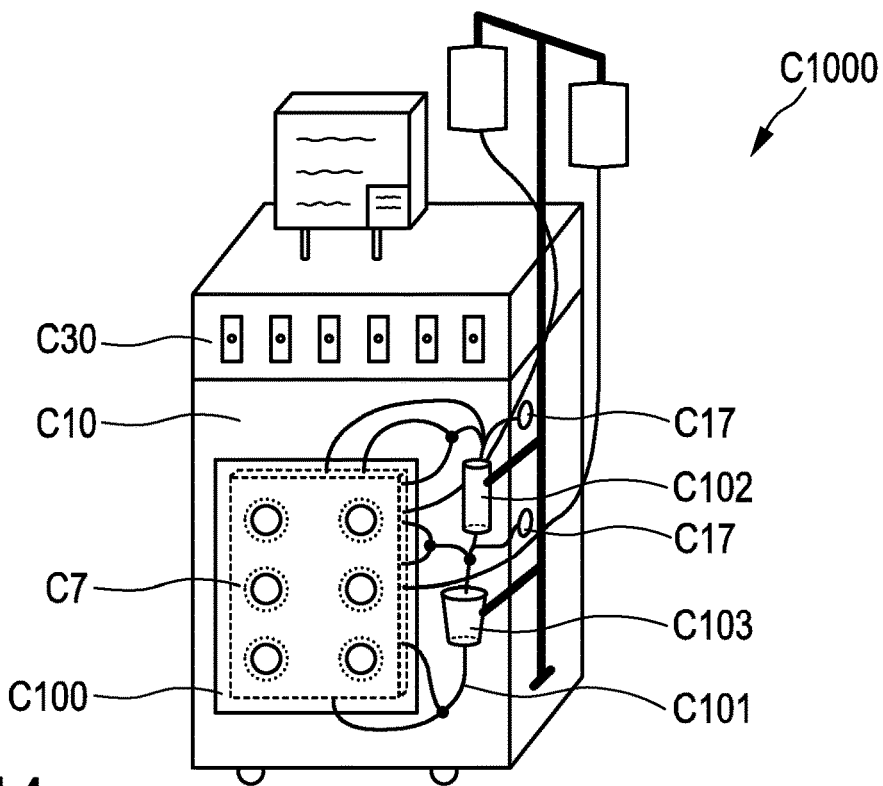
FIG. 14 is a schematic representation of an embodiment of a herein disclosed arrangement for treating blood.

Shown are:

FIG. 14 a schematic representation of an embodiment of an herein disclosed arrangement for treating blood.

Figure 15:
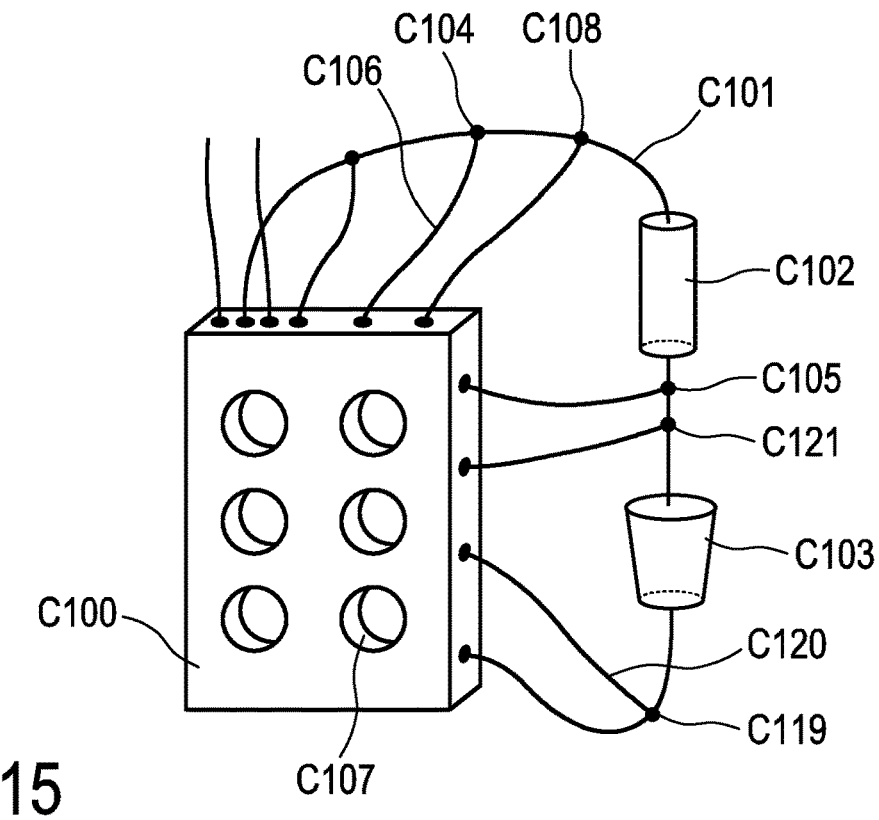
FIG. 15 is a schematic representation of an embodiment of a herein disclosed blood-guiding apparatus with connected dialyzer as well as connected blood treatment element.

FIG. 15 a schematic representation of an embodiment of an herein disclosed blood-guiding apparatus with connected dialyzer as well as connected blood treatment element.

Figure 16A:
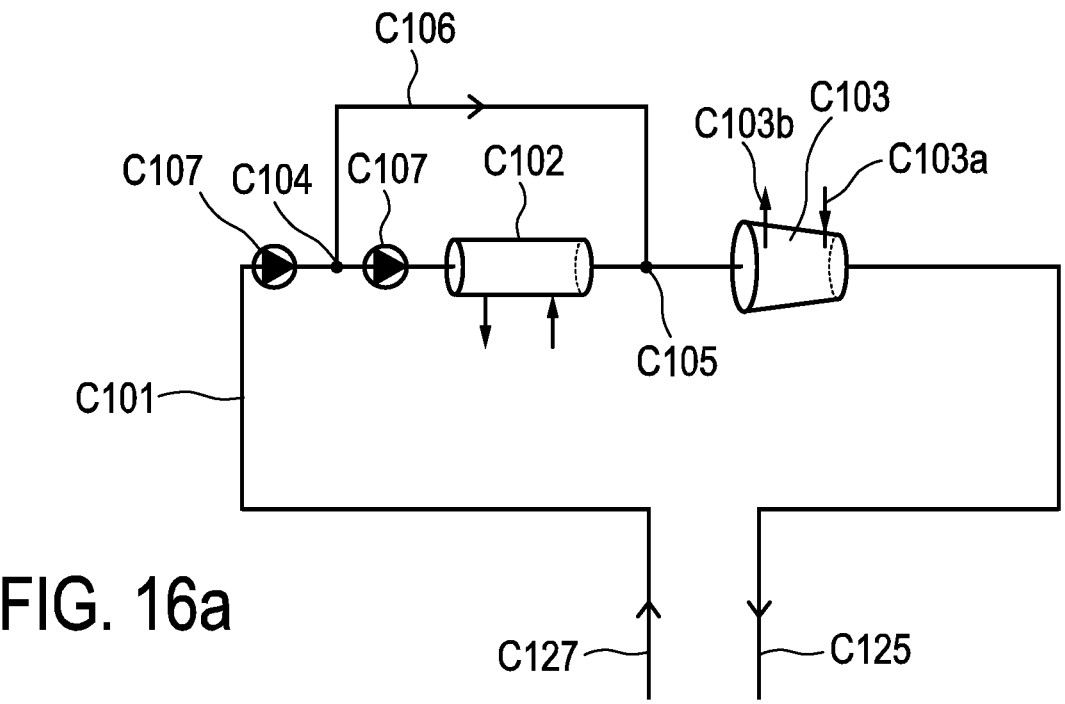
FIG. 16a is a flow diagram of a herein disclosed blood-guiding apparatus in schematic representation.

FIG. 16*a* the flow diagram of an herein disclosed blood-guiding apparatus in schematic representation.

Figure 16B:
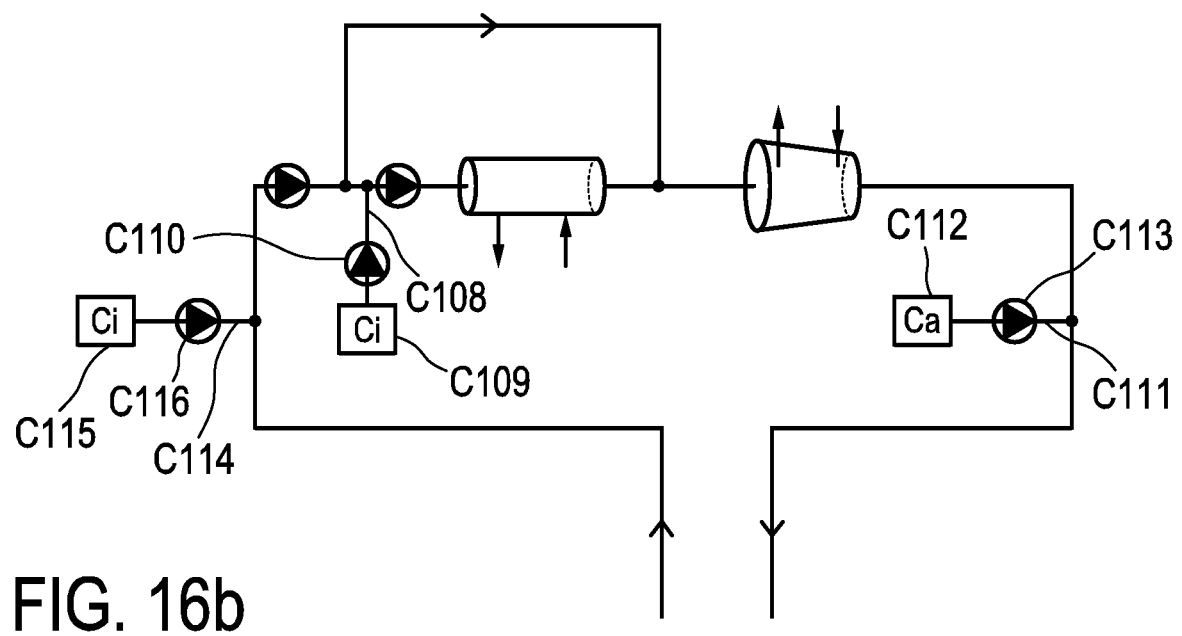
FIG. 16b is the flow diagram of the blood-guiding apparatus shown in FIG. 16a in schematic representation with further optional components.

FIG. 16*b* the flow diagram of the blood-guiding apparatus shown in FIG. 16*a* in schematic representation with further optional components.

Figure 17A:
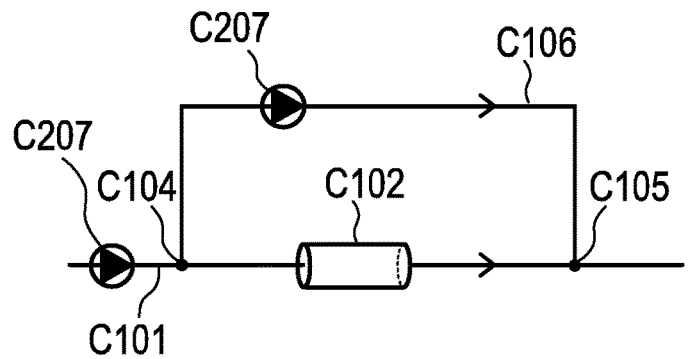
FIG. 17a is an example of an alternative embodiment variant of the pump assembly, represented by the pump assembly sections, in a schematic representation of the flow diagram.

FIG. 17*a* an example of an alternative embodiment variant of the pump assembly, represented by the pump assembly sections, in a schematic representation of the flow diagram.

Figure 17B:
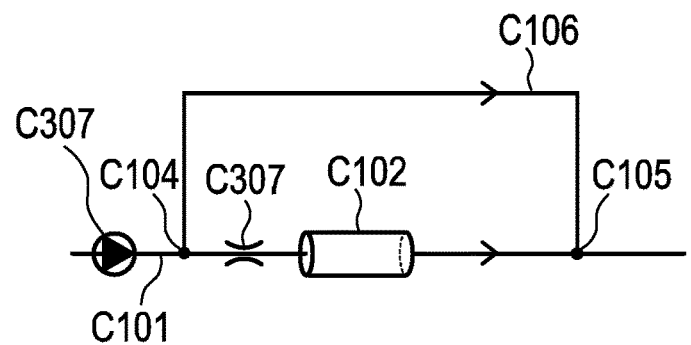
FIG. 17b is an example of a further alternative embodiment variant of the pump assembly, represented by the pump assembly sections, in a schematic representation of the flow diagram.

FIG. 17*b* an example of a further alternative embodiment variant of the pump assembly, represented by the pump assembly sections, in a schematic representation of the flow diagram.

Figure 17C:
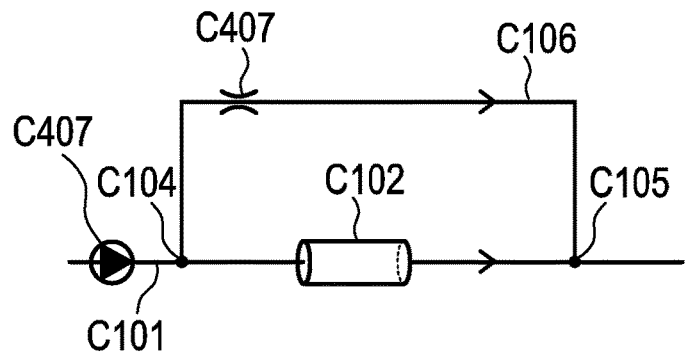
FIG. 17c is an example of a further alternative embodiment variant of the pump assembly, represented by the pump assembly sections, in a schematic representation of the flow diagram.

FIG. 17*c* an example of a further alternative embodiment variant of the pump assembly, represented by the pump assembly sections, in a schematic representation of the flow diagram.

Figure 17D:
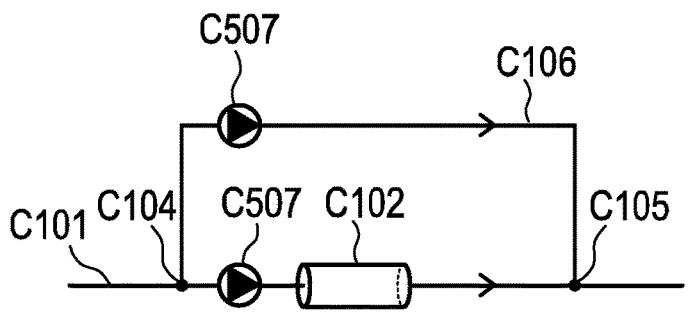
FIG. 17d is an example of a further alternative embodiment variant of the pump assembly, represented by the pump assembly sections, in a schematic representation of the flow diagram.

FIG. 17*d* an example of a further alternative embodiment variant of the pump assembly, represented by the pump assembly sections, in a schematic representation of the flow diagram.

Figure 18A:
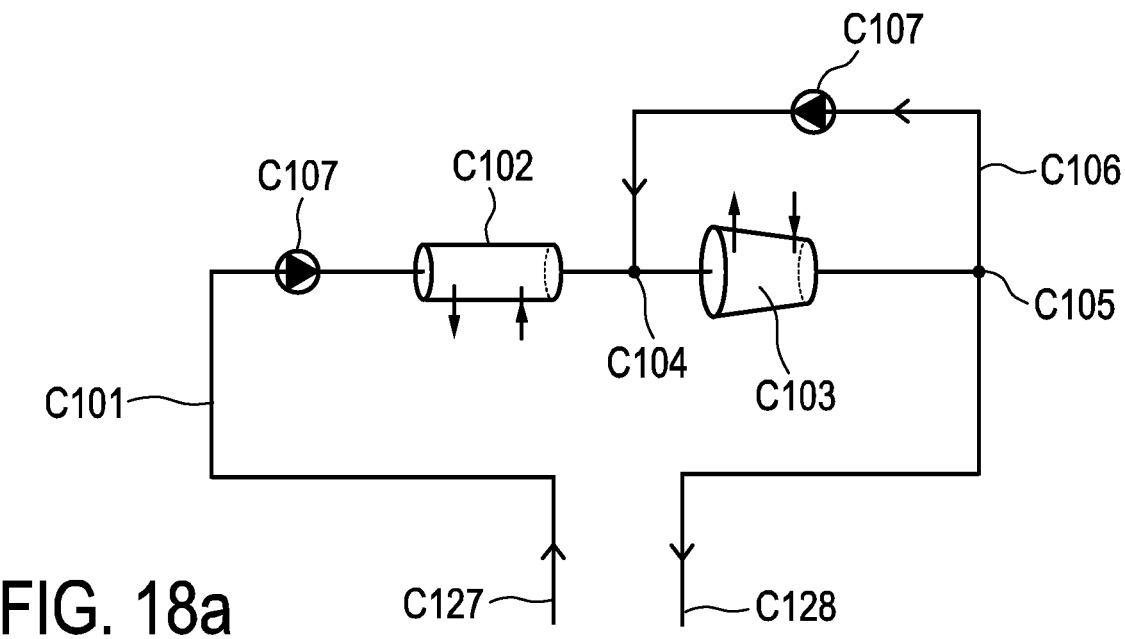
FIG. 18a is a flow diagram of a herein disclosed blood-guiding apparatus in an alternative embodiment in schematic representation.

FIG. 18*a* the flow diagram of a herein disclosed blood-guiding apparatus in an alternative embodiment in schematic representation.

Figure 18B:
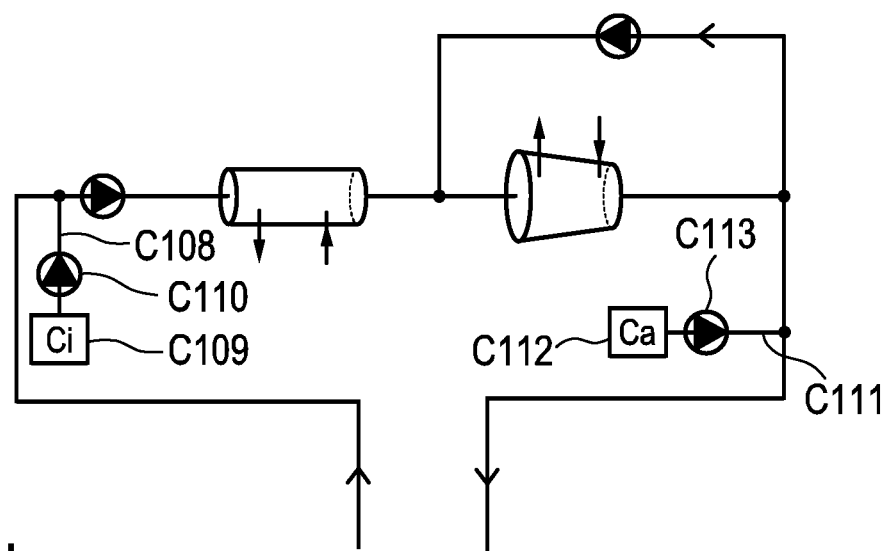
FIG. 18b is the flow diagram of the blood-guiding apparatus shown in FIG. 18a in schematic representation with further optional components.

FIG. 18*b* the flow diagram of the blood-guiding apparatus shown in FIG. 18*a* in schematic representation with further optional components.

Figure 19A:
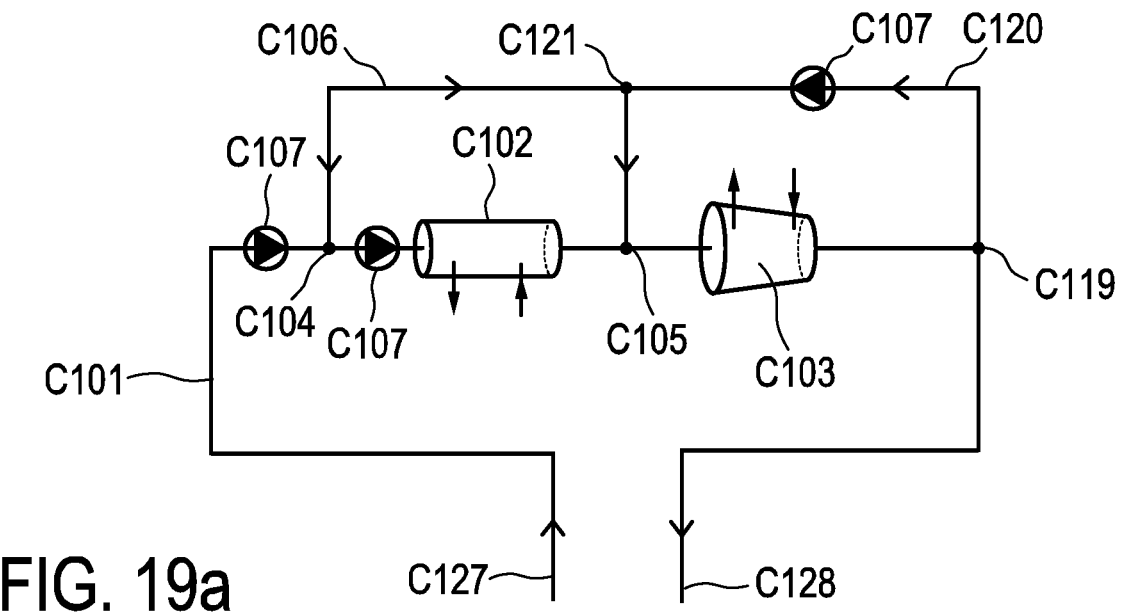
FIG. 19a is a flow diagram of a further alternative embodiment of a herein disclosed blood-guiding apparatus in schematic representation.

FIG. 19*a* the flow diagram of a further alternative embodiment of a herein disclosed blood-guiding apparatus in schematic representation.

Figure 19B:
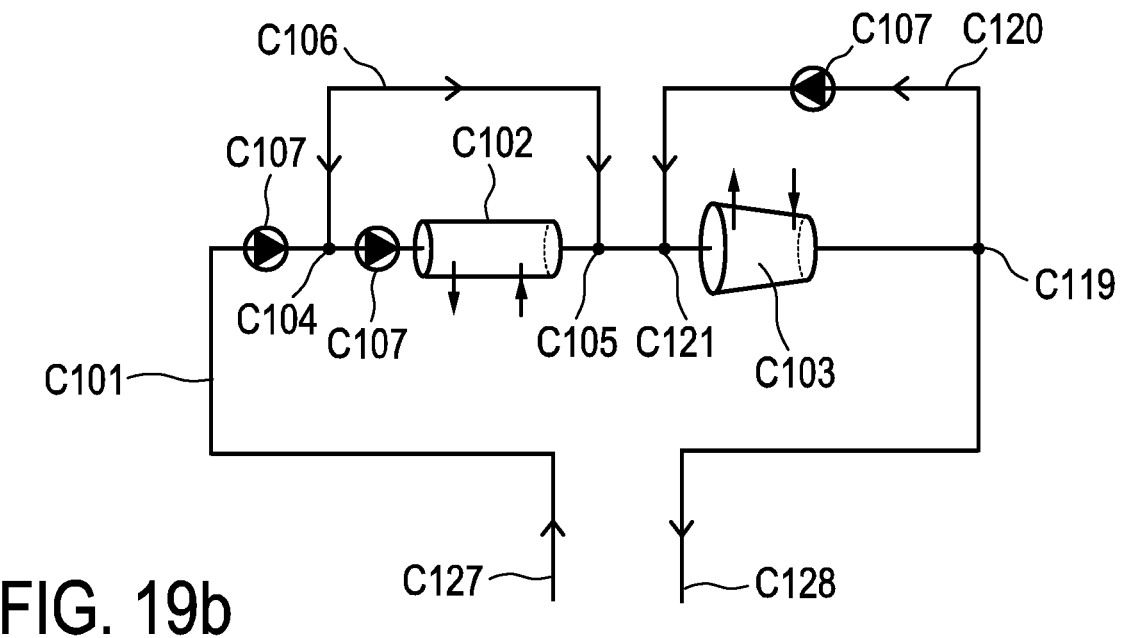
FIG. 19b is the flow diagram of the blood-guiding apparatus shown in FIG. 19a, with an alternative arrangement of the recirculation return port, in schematic representation.

FIG. 19*b* the flow diagram of the blood-guiding apparatus shown in FIG. 19*a* with an alternative arrangement of the recirculation return port in schematic representation.

Figure 20:
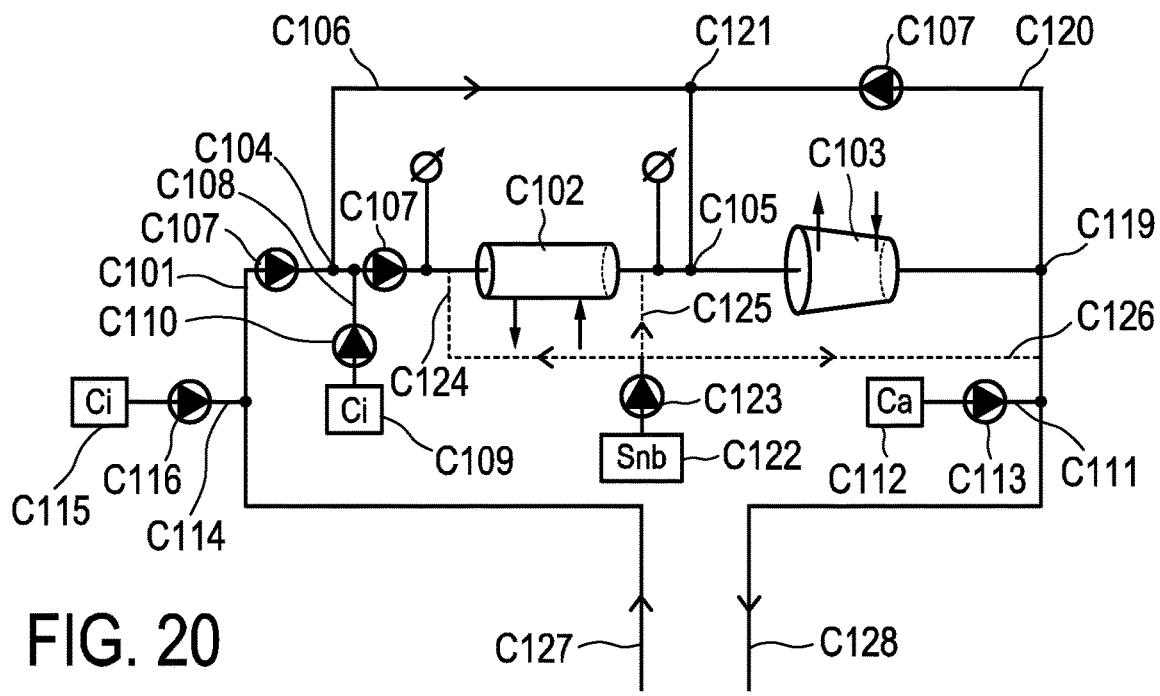
FIG. 20 is the flow diagram of the blood-guiding apparatus shown in FIG. 19a, in schematic representation, with further optional components.

FIG. 20 the flow diagram of the blood-guiding apparatus shown in FIG. 19*a* in schematic representation with further optional components.

Figure 21:
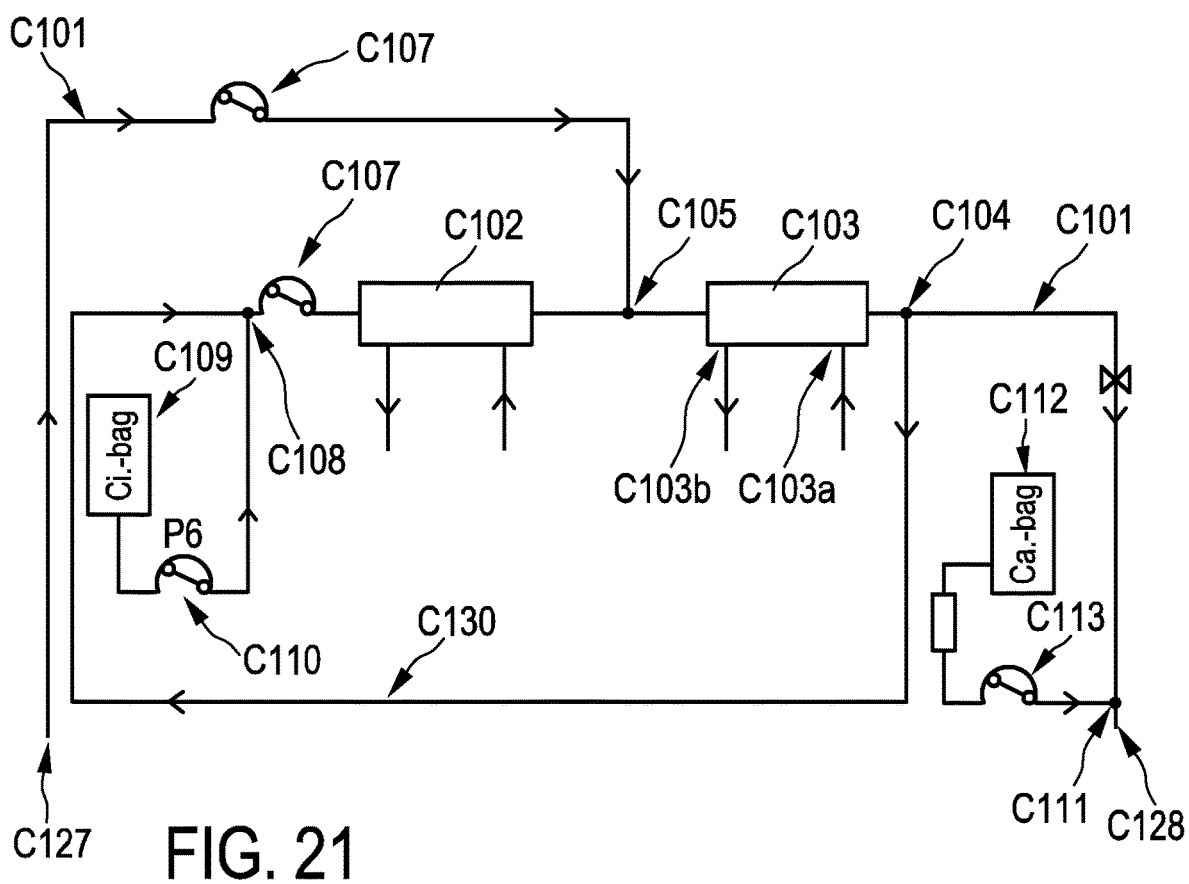
FIG. 21 is a flow diagram of a further embodiment of a blood treatment apparatus in schematic representation in which the dialyzer is arranged in the secondary line.

FIG. 21 the flow diagram of a further embodiment of a blood treatment apparatus in schematic representation in which the dialyzer is arranged in the secondary line.

As depicted in FIG. 14, the arrangement for blood treatment C1000 comprises a functional unit C10 as well as a blood-guiding apparatus C100. FIG. 14 shows the functional unit C10 in the form of a dialysis machine for acute dialysis which is equipped with a blood-guiding apparatus C100 designed as a cassette. The blood treatment apparatus comprises a control apparatus C30 as well as a pump assembly C7. FIG. 14 further shows the main blood line C101 of the blood-guiding apparatus C100, to which a dialyzer C102 as well as a blood treatment element C103 in the form of a gas exchanger are connected. The main blood line C101 can further comprise one or more pressure measuring sections, at which the pressure can be captured by means of the pressure sensors C17 optionally provided in the functional unit C10.

As herein disclosed, the blood guidance apparatus C100 can be designed as a medical disposable in the form of a blood cassette (FIG. 15). The blood guidance apparatus C100 can comprise one or more pump assembly sections C107 on which the pump assembly C7 of the blood treatment apparatus C10 can act in order to convey the fluid in the corresponding line section of the blood-guiding apparatus C100. FIG. 15 shows the main blood line C101, which leads away from the cassette body of the blood-guiding apparatus C100, the dialyzer C102 as well as the blood treatment element C103, here in the form of a gas exchanger, in succession and then leads back into the cassette body where the pump assembly sections C107 can be arranged. The first branching point C104 from which the first secondary line C106 leads away can be arranged upstream of the dialyzer C102. The second branching point C105 at which the first secondary line C106 rejoins the main blood line C101 can be arranged downstream of the dialyzer C102 and upstream of the blood treatment element C103. An addition port C108 for a first medical fluid for anticoagulation, e.g. citrate, can further be arranged upstream of the dialyzer C102. A recirculation branching point C119 from which the second secondary line C120 leads away can be arranged downstream of the blood treatment element C103. The second secondary line C120 opens into a recirculation return port C121 which can be arranged in the main blood line C101 upstream of the blood treatment element C103 and downstream of the dialyzer C102.

The blood-guiding apparatus C100 exhibits a main blood line C101, wherein the main blood line C101 has a blood sampling port C127 for connecting to a patient's blood sampling access at one end and a blood return port C128 for connecting to a patient's blood return access at another end. The blood drawn from the patient can be extracorporeally guided in the main blood line C101 to the dialyzer C102 and the blood treatment element C103 for the further extracorporeal blood treatment therapy as well as reinfused back into the patient, as depicted schematically in the flow diagram of FIG. 16a.

A dialyzer C102 is arranged in the main blood line. This customarily has a blood chamber and a dialysate chamber (not shown here), whereby the two chambers are separated by a semi-permeable membrane via which the blood can osmotically interact with the dialysis solution flowing in the dialysate circuit. As herein disclosed, the dialyzer can also be used for other common renal replacement or renal support therapies in dialysis such as e.g. hemodiafiltration, hemodialysis, hemoperfusion, hemofiltration, ISO-UF, etc., in particular also for treatment methods with no dialysis solution being conveyed on the dialysate side.

Downstream of the dialyzer C102, the main blood line C101 leads through a blood treatment element C103, here configured as a gas exchanger. This has a blood chamber and a gas chamber (not shown here), whereby the two chambers are separated by a semi-permeable membrane via which the blood can osmotically interact with the gas flowing in the gas line.

Both the dialyzer C102 and the gas exchanger C103 can thereby have a large number of individual membranes in the form of hollow fibers. In the context of the present disclosure, the individual chambers for blood, dialysate or gas can thereby each also consist of a large number of individual volumes located inside the hollow fibers, these being fluidly connected to one another at the end of the fibers.

The main blood line C101 has a first branching point C104 upstream of the dialyzer C102. A first secondary line C106 leads from this first branching point C104 to a second branching point C105 of the main blood line C101.

The blood-guiding apparatus further comprises pump assembly sections C107 at which the blood can be conveyed both through the main blood line C101 as well as through the first secondary line C106 by means of the pump assembly C7 of the functional unit C10. In the exemplary embodiment of FIG. 16a, the first pump assembly C7 is realized in the form of two occluding blood pumps, whereby one is arranged in the main blood line C101 upstream of the first branching point C104 and the second in the main blood line C101 downstream of the first branching point C104 and upstream of the dialyzer C102. In this exemplary embodiment, the first pump pumps for example at 500 ml/min while the second pump only pumps at 200 ml/min. A flow of 300 ml/min is thus set in the secondary line C106. A blood flow of 200 ml/min is established at the dialyzer C102 and the gas exchanger C103 is flowed through at 500 ml/min as the two flow components of 200 ml/min and 300 ml/min reunite again at the second branching point 105.

As can further be seen in FIG. 16a, the gas exchanger for reducing the carbon dioxide content of blood C103 has an inlet port C103a and an outlet port C103b. Buffer solution according to the first aspect of the present disclosure, in particular as defined by the features of at least one of the forms of use 1 to 6, is introduced into and discharged from the second delimited region of the gas exchanger via the inlet port and the outlet port. The gas exchanger C103 thereby corresponds in its functioning and design to the apparatus for reducing the carbon dioxide content in blood according to the implementation of the first aspect of the present disclosure in particular as illustrated in FIG. 3, further particularly as defined in at least one of the embodiments 8 to 19.

As depicted schematically in FIG. 16b, the blood-guiding apparatus can optionally comprise addition ports for medical anticoagulation liquid. Thus, an addition port C108 for citrate solution can be arranged downstream of the first branching point C104 and upstream of the dialyzer C102. This can also be configured as a citrate line C108 connected to a citrate reservoir C109. Furthermore, the functional unit C10 can have an infusion pump C110 which is designed to convey citrate from the reservoir C112 into the main blood line C101 via addition port C108. An addition port C111 for calcium solution can be arranged downstream of the blood treatment element C103. This can also be configured as a calcium line C111 connected to a calcium reservoir C112. Furthermore, the functional unit C10 can have a further infusion pump C113 designed to convey calcium from the reservoir C112 into the main blood line C101 via addition port C111.

FIG. 16b further shows a further optional citrate addition possibility. A third addition port C114 for medical anticoagulation liquid is to that end arranged in the main blood line upstream of the first branching point C104. The addition port C114 can also be configured as a citrate line connected to a citrate reservoir C115. Furthermore, the functional unit C10 can have a further infusion pump C116 designed to convey citrate from the reservoir C115 into the main blood line C101 via addition port C114. Alternatively (not shown here), the third addition line C114 can also be supplied from the first reservoir C109. Further alternatively, the third infusion pump C116 can also be omitted if the pressure generated by the first infusion pump C110 is used in a third addition line which branches off afterwards. The third addition line can thereby have a valve or a throttle which adjusts the pressure accordingly.

FIGS. 17a to 17d each schematically show a section of the main blood line C101 of the blood-guiding apparatus C100 in the area around the first branching point C104 and the second branching point C105 which, in this embodiment, contains the two flow paths over secondary line C106 as well as over the section of the main blood line 101 through the dialyzer C102. FIGS. 17a to 17d show various possible exemplary implementations of the pump assembly, represented by pump assembly sections C207, C307, C407, C507, for the action of the pump assembly C7 of the functional unit C10.

While the pump assembly of the embodiment specified in FIG. 16a, represented by pump assembly sections C107, has an occluding blood pump in the main blood line C101 upstream of the first branching point C104 and a further occluding blood pump in the main blood line C101 between the dialyzer C102 and the first branching point C104, FIG. 17a shows a variant of the pump assembly, represented by pump assembly sections C207, which likewise has a first blood pump in the main blood line C101 upstream of the first branching point C104 albeit with an alternative arrangement of the further occluding blood pump in the secondary line C106.

In the pump assembly examples shown in FIGS. 17b and 17c, represented by pump assembly sections C307, C407, the further blood pumps in the secondary line C106 or respectively in the main blood line C101 between the dialyzer C102 and the first branching point C104 are each replaced by throttling elements.

FIG. 17d shows a further exemplary embodiment of a first pump assembly, represented by pump assembly sections C507, which has two occluding blood pumps, whereby one is arranged in secondary line C106 and the other is located in the main blood line C101 between the dialyzer C102 and the first branching point C104.

All of the pump assemblies according to the present disclosure can both generate a blood flow in the main blood line C101 as well as also conduct a partial flow having a defined flow rate over the secondary line C106 such that the ratio between the total flow in the main blood line C101 upstream of the first branching line C104, or downstream of the second branching line C105 respectively, and in the region of the dialyzer C102 is thereby adjustable. The present disclosure is not limited to the embodiments of the pump assembly C7 shown in FIGS. 17a to 17d. As one skilled in the art recognizes, there are numerous other possibilities in the prior art for controlling the ratio of the flows in the two line sections. In some embodiments, the pump assembly C7 can control the flows of the two line sections independently of each other. The pump assembly C7 can comprise various fluidic components including occluding pumps, non-occluding pumps, clamps, valves, throttles, etc. The components of the pump assembly C7 can be arranged or act at other points within the extracorporeal blood circuit.

As shown schematically in FIG. 18a on the basis of the flow diagram, the blood-guiding apparatus C100 can also exhibit an alternative flow routing. In this example, the first branching point C104, at which the secondary line C106 branches off from the main blood line C101, is arranged downstream of the blood treatment element C103. In this example, the second branching point C105, at which the secondary line C106 again reunites with the main blood line C101, is furthermore arranged upstream of the blood treatment element C103 and downstream of the dialyzer C102.

As shown schematically in FIG. 18b, the blood-guiding apparatus can optionally have addition ports for medical anticoagulation liquid. Thus, an addition port C108 for citrate solution can be arranged upstream of the dialyzer C102. This can also be configured as a citrate line C108 connected to a citrate reservoir C109. Furthermore, the functional unit C10 can have an infusion pump C110 designed to convey citrate from the reservoir C112 into the main blood line C101 via the addition port C108. An addition port C111 for calcium solution can be arranged downstream of the blood treatment element C103. This can also be configured as a calcium line C111 connected to a calcium reservoir C112. The functional unit 10 can furthermore have a further infusion pump C113 designed to convey calcium from the reservoir C112 into the main blood line C101 via addition port C111.

FIG. 19a schematically shows a further alternative embodiment of a herein disclosed blood-guiding apparatus on the basis of the flow diagram, whereby in addition to the features of FIG. 16a, a second branching line C120 is provided here for the repeated recirculation of the blood through the blood treatment element C103, designed here as a gas exchanger. The second secondary line C120 leads off from the main blood line C101 at a recirculation branching point C119 and opens into a recirculation return port C121. In the example of FIG. 19a, the recirculation return port C121 is arranged in the first secondary line C106 upstream of the second branching point C105. The example of FIG. 19b shows an alternative line routing to that end and differs from that shown in FIG. 19a in that the recirculation return port C121 is arranged directly in the main blood line C101 downstream of the dialyzer C102 and upstream of the blood treatment element C103. In these embodiments of FIGS. 19a and 19b, the pump assembly C7 of the functional unit C10 can be further equipped to generate a blood flow in the second secondary line C120. To that end, the pump assembly C7 of the functional unit 10 in FIGS. 19a and 19b—represented here by pump assembly sections C107—has a further occluding pump in the second secondary line C120. Moreover, the control apparatus C30 of the functional unit C10 can be configured to operate the pump assembly C7 such that the blood flow rate in at least one section of the main blood line C101 is independent of at least one of the blood flow rates in the secondary lines C106, C120.

FIG. 20 schematically shows an embodiment of the blood-guiding apparatus from FIG. 19a with additional optional components. The addition ports C108, C111, C114, the corresponding infusion pumps C110, C113, C116 as well as reservoirs C109, C112, C115 already described with respect to the exemplary embodiment of FIG. 19b can also be provided in the embodiment with the two secondary lines C106, C120.

FIG. 20 furthermore shows two optional pressure measurements C117, C118 in the main blood line C101 downstream as well as upstream of the dialyzer C102. On the one hand, the pressure downstream of the dialyzer and optionally also upstream of the dialyzer is helpful in determining the transmembrane pressure. This represents an important parameter which for example provides information about imminent filter clogging over the course of the dialysis therapy. The transmembrane pressure can also be taken into account when determining the calcium addition rate via the second addition port C111. On the other hand, the pressures in the respective flow sections are also helpful in monitoring the therapy via a threshold window.

FIG. 20 furthermore shows optional components which also allow hemofiltration and/or hemodiafiltration on the renal replacement therapy side. To that end, the extracorporeal blood circuit can comprise one or more addition ports C124, C125, C126 for dilution liquid, optionally also designed as a substitute line, through which substitution fluid can be added into the main blood line C101 from a reservoir C122 by means of a further infusion pump C123. The substitute line can thereby be connected in predilution C124, then empty into the main blood line C101 upstream of the dialyzer C102. The substitute line can also be connected in postdilution. The blood circuit according to the present disclosure offers two possible connection positions in postdilution. In a first option, the postdilution line C125 can open into the main blood line C101 between the dialyzer C102 and the blood treatment element C103. In a second option, the postdilution line C126 can also open into the main blood line C101 downstream of the gas exchanger. The latter variant C126 thereby offers the advantage that the substitution solution, which normally contains calcium, only reduces the anticoagulant effect of the citrate in the rearward part of the extracorporeal blood circuit.

Alternatively, the user can also selectively connect the substitute line to one or more of the cited positions. In a combination of predilution and postdilution, two independently conducting infusion pumps for the dilution liquid is also selectively possible (not shown).

FIG. 21 schematically shows an embodiment of a blood-guiding apparatus in which the dialyzer is arranged in a secondary line C130. The secondary line C130 branches off from the main blood line C101 at the branching point C104 downstream of the blood treatment element C103 for reducing the carbon dioxide content in blood and reunites with the main blood line C101 at the branching point C105 upstream of the blood treatment element C103. Arranged in secondary line C130 is a dialyzer C102 as well as a pump assembly section C107 which regulates in conjunction with a pump assembly C7 and an adjustable blood flow in the secondary line C130. An addition port for a first medical anticoagulation liquid, in particular a citrate solution, is furthermore situated in the secondary blood line C130, via which a first medical fluid, in particular a citrate solution, can be infused into the bloodstream of the secondary line C130 from a reservoir C109 for anticoagulation by means of an infusion pump C110.

In accordance with the FIG. 21 embodiment, a pump assembly section C107 is arranged in the main blood line upstream of the branching point C105 and the blood treatment element C103 with which blood can be drawn from a patient via blood sampling port C127 in conjunction with a pump assembly C7 and a blood flow in the main blood line can be regulated. The blood-guiding apparatus has an addition port for a second medical anticoagulation fluid C111, in particular a calcium solution, downstream of the blood treatment element C103, via which the second medical fluid, in particular the calcium solution, can be infused into the bloodstream of the main blood line from a reservoir C112. Furthermore, the main blood line C130 has a blood return port via which the treated blood can be returned to the patient.

Furthermore, the blood treatment element C103 comprises an inlet port C103a and an outlet port C103b via which a buffer solution according to one of the embodiments pursuant to the first aspect of the present disclosure for reducing the carbon dioxide content in blood can flow through a second delimited region (not shown) of the blood treatment element C103.

The blood-guiding apparatus according to FIG. 21 has the advantage of being able to decouple the bloodstreams to be treated in the dialyzer C102 and in the treatment element C103 from one another, as is necessary from a medical and therapeutic standpoint for the combined treatment of blood by dialysis and reduction of carbon dioxide content. In one preferential extracorporeal blood treatment of a patient using the blood-guiding apparatus shown schematically in FIG. 21, the various required blood flows can be set and regulated in the various different sections of the secondary line C130 and the main blood line C101. In particular, a blood flow of 500 ml/min can be set in the main blood line C101 upstream of the blood treatment element C103 while a blood flow of 200 ml/min can be set in the secondary line. The blood flows in the main blood line C101 and the secondary line C130 are joined via branching point C105 so that a blood flow of 700 ml/min is established in the section of the main blood line between the branching point C105 upstream of the blood treatment element C103 and the branching point C104 downstream of the blood treatment element C103. The blood treatment element C103 is thereby flowed through at the high blood flow necessary from a therapeutic standpoint, whereas the dialyzer C102 is flowed through at a lower blood flow necessary from a therapeutic standpoint. A blood flow of 500 ml/min is established downstream of branching point C104 and downstream of the blood treatment element C103 by the cited setting of the blood flows in the main blood line and secondary line.

The functional device C10 comprises a control apparatus C30. The control apparatus C30 can be configured to control and regulate a treatment method. According to one method encompassed by the present disclosure, the pump assembly C7 can generate a blood flow in the main blood line C101 of between 0 and 300 ml/min in the region of the dialyzer C102 in all the exemplary embodiments. Moreover, a blood flow greater than 500 ml/min can be generated in the region of the blood treatment element C103. In the example of FIGS. 16a and 16b, the flow rate in the main blood line C101 ahead of the first branching point C104 corresponds to the flow rate in the blood treatment element C103. The desired dialyzer flow rate can be set by means of pump assembly C7. The flow rate in the secondary line C106 thus results as the difference between the flow rates in the blood treatment element C103 and the dialyzer.

The flow rate in the blood treatment element C103 can also be greater than 800 ml/min, greater than 1 l/min or greater than 2 l/min in all the embodiments of the present disclosure. All these flow rates and even greater are possible according to the present disclosure in the scope of using a blood treatment element C103.

The dialyzer flow rate can also be in the range of between 100 and 250 ml/min in all the embodiments. It can also be in the range of 175 to 225 ml/min or amount to exactly 200 ml/min.

The flow rate of the first medical fluid for anticoagulation, for example citrate, conveyed into the main blood line C101 by means of the first infusion pump C110 can be regulated by the control apparatus C30 as a function of the dialyzer flow rate.

The flow rate of the second medical fluid for anticoagulation, for example calcium, conveyed into the main blood line C101 by means of the second infusion pump C113 can be regulated by the control apparatus C30 as a function of the dialyzer flow rate. The regulating can additionally take other dependencies into account such as, for example, the flow rate of the first medical anticoagulation fluid, the flow rate of the third medical anticoagulation fluid, the transmembrane pressure (TMP), the type of dialyzer, and/or other parameters, optionally also to be selected or supplied by the user.

The flow rate of the third medical fluid for anticoagulation, for example citrate, can be controlled by direct user selection. It can also be regulated as a function of the flow rate in the blood treatment element C103 or the difference between the flow rates in the blood treatment element 103 and the dialyzer.

In a third aspect, the subject of the present disclosure is characterized by the features of the following embodiments 38 to 50:

Embodiment 38

A functional unit (C10) for performing an extracorporeal blood treatment in which the blood is guided in a blood-guiding apparatus (C100) having a main blood line (C101) and at least one secondary line (C106, C130) which is fluidly connected to the main blood line (C101) and wherein the main blood line (C101) comprises a dialyzer (C102) as well as a blood treatment element (C103) downstream of the dialyzer (C102), or
- wherein the main blood line (C101) comprises a treatment element (C103) and the secondary line (130) comprises a dialyzer,
- wherein the blood treatment element (C103) comprises an apparatus for the extracorporeal reduction of the carbon dioxide content in blood (10) as described herein, and wherein the functional unit (C10) comprises:
- a control apparatus (C30); and
- a pump assembly (C7) which is configured to generate blood flows in the main blood line (C101) as well as in the at least one secondary line (C106),
- wherein the control apparatus (C30) is configured to operate the pump assembly (C7) such that a first blood flow rate in the dialyzer (C102) is decoupled from a second blood flow rate in the blood treatment element (C103).

Embodiment 39

The functional unit (C10) as described herein,
- wherein the pump assembly (C7) is designed to generate mutually independent blood flow rates in the main blood line (C101) and in the at least one secondary line (C106).

Embodiment 40

The functional unit (C10) as described herein, wherein the extracorporeal blood treatment apparatus (C100) further comprises a second secondary line (C120) which is fluidly connected to the main blood line (C101),
- wherein the pump assembly (C7) is further equipped to generate a blood flow in the second secondary line (C120), and
- wherein the control apparatus (C30) is configured to operate the pump assembly (C7) such that the blood flow rate in at least one section of the main blood line (C101) is independent from at least one of the blood flow rates in the secondary lines (C106, C120).

Embodiment 41

The functional unit (C10) as described herein, wherein the functional unit (C10) comprises:
- an infusion pump (C110) for supplying medical fluid into the main blood line (C101) or into the secondary line (130),
- two infusion pumps (C110, C113) for supplying medical fluid into the main blood line (C101), or for supplying medical fluid into the main blood line (C101) and the secondary line (C130),
- three infusion pumps (C110, C113, C116) for supplying medical fluid into the main blood line (C101), or
- four or more infusion pumps (C110, C113, 116, C123) for supplying medical fluid into the main blood line (C101).

Embodiment 42

The functional unit (C10) as described herein, wherein the control apparatus (C30) is configured to regulate the feed rate of at least one of the infusion pumps as a function of the blood flow rate in the dialyzer (C102), in particular wherein the control apparatus (C30) is configured to regulate each feed rate of at least two of the infusion pumps as a function of the blood flow rate in the dialyzer (C102).

Embodiment 43

The functional unit (C10) as described herein, wherein the functional unit (C10) comprises a pressure sensor (C17) for determining the pressure in the main blood line (C101) downstream of the dialyzer (C102) as well as upstream of the blood treatment element (C103).

Embodiment 44

A blood-guiding apparatus (C100) for interacting with a functional unit (C10) as described herein, comprising:
- a main blood line (C101) for fluidic connection to a dialyzer (C102) as well as for fluidic connection to a blood treatment element (C103) downstream of the dialyzer (C102), wherein the blood treatment element (C103) is an apparatus for the extracorporeal reduction of the carbon dioxide content in blood (10) as described herein, wherein the main blood line (C101) has a blood sampling port (C127) for connecting to a blood sampling access of a patient at one end and a blood return port (C128) for connecting to a blood return access of the patient at another end, and at least one secondary line (C106) which leads away from the main blood line (C101) at a first branching point (C104) and reunites with the main blood line (C101) at a second branching point (C105); or
- a main blood line (C101) for fluidic connection to a blood treatment element (C103), wherein the blood treatment element (C103) is an apparatus for the extracorporeal reduction of the carbon dioxide content in blood (10) as described herein, and comprises a secondary blood line (C130) for fluidic connection to a dialyzer, wherein the main blood line (C101) has a blood sampling port (C127) for connecting to a blood sampling access of a patient at one end and a blood return port (C128) for connecting to a blood return access of the patient at another end, wherein the secondary line (C130) which leads away from the main blood line (C101) at a first branching point (C104) reunites again with the main blood line (C101) at a second branching point (C105);
- and one or more pump assembly sections (C107), designed to act on the pump assembly (C7) of the blood treatment apparatus (C10).

Embodiment 45

The blood-guiding apparatus (C100) as described herein, wherein the first branching point (C104) is arranged upstream of the connection point for the dialyzer (C102), and
- the second branching point (C105) is arranged downstream of the connection point for the dialyzer (C102)

as well as upstream of the connection point for the blood treatment element (C103); or wherein the first branching point (C104) is arranged downstream of the connection point for the blood treatment element (C103), and the second branching point (C105) is arranged upstream of the connection point for the blood treatment element (C103) as well as downstream of the connection point for the dialyzer (C102).

Embodiment 46

The blood-guiding apparatus (C100) as described herein, comprising a second secondary line (C120) which leads away from the main blood line (C101) at recirculation branching point (C119) and opens into a recirculation return port (C121), wherein the first branching point (C104) is arranged upstream of the connection point for the dialyzer (C102), and wherein the second branching point (C105) is arranged downstream of the connection point for the dialyzer (C102) as well as upstream of the connection point for the blood treatment element (C103), and wherein the recirculation branching point (C119) is arranged downstream of the connection point for the blood treatment element (C103), and wherein the recirculation return port (C121) in the main blood line (C101) is arranged upstream of the connection point for the blood treatment element (C103) as well as downstream of the connection point for the dialyzer (C102), or wherein the recirculation return port (C121) in the first secondary line (C106) is arranged upstream of the second branching point (C105).

Embodiment 47

The blood-guiding apparatus (C100) as described herein, wherein the main blood line (C101) comprises:

an addition port (C108) for a first medical anticoagulation liquid upstream of the connection point for the dialyzer (C102); and/or an addition port (C111) for a second medical anticoagulation liquid downstream of the connection point for the treatment element (C103); or wherein the main blood line (C101) comprises:

an addition port (C108) for a first medical anticoagulation liquid downstream of the first branching point (C104) as well as upstream of the connection point for the dialyzer (C102); and/or an addition port (C111) for a second medical anticoagulation liquid downstream of the connection point for the treatment element (C103);

or an addition port (C108) for a first medical anticoagulation liquid upstream of the dialyzer (C102) in the secondary line (C130) as well as an addition port (C111) for a second medical anticoagulation liquid downstream of the connection point for the treatment element (C103);

and/or an addition port (C114) for a third medical anticoagulation liquid upstream of the first branching point (C104).

Embodiment 48

The blood-guiding apparatus (C100) according to one implementation as described herein, wherein the main blood line (C101) comprises a pressure measuring section (C117) downstream of the connection point for the dialyzer (C102) as well as upstream of the connection point for the blood treatment element (C103) for determining the pressure in the main blood line (C101).

Embodiment 49

The blood-guiding apparatus (C100) according to one implementation as described herein, wherein the main blood line (C101) comprises:

an addition port (C124) for a dilution liquid upstream of the connection point for the dialyzer (C102); and/or an addition port (C125) for a dilution liquid downstream of the connection point for the dialyzer (C102) as well as upstream of the connection point for the blood treatment element (C103); and/or an addition port (C126) for a dilution liquid downstream of the connection point for the blood treatment element (C103).

Embodiment 50

An arrangement for blood treatment (C1000), comprising:
a functional unit (C10) as described herein; and
a blood-guiding apparatus (C100) as described herein.

In a fourth aspect, the present disclosure relates to an inventive treatment system for reducing the carbon dioxide content in blood in an extracorporeal blood circuit, comprising an apparatus for the extracorporeal reduction of the carbon dioxide content in blood comprising a first delimited region (1) for receiving extracorporeal blood and a second delimited region (2) for receiving a buffer solution, wherein the first (1) and second region (2) adjoining each other in a contact zone are only separated by a membrane (3), via which gas exchange can occur between the blood and the buffer solution, and wherein the buffer solution is an aqueous solution in gas exchange with the blood of the patient conducted in an extracorporeal circuit and contains a buffer A and a buffer B, wherein buffer A consists of at least one buffer substance having a pK value of 7.9±0.2 at 37° C., and buffer B consists of at least one buffer substance having a pK value of 6.9±0.2 at 37° C., and wherein the solution has a post-titration pH value in the range of 8.25 to 8.35 at a carbon dioxide partial pressure of $pCO_2$=0.2 mmHg±0.2.

a first inlet for introducing a bloodstream to be treated into the treatment system, wherein the first inlet is in fluid communication with the first inlet port at the first delimited region of the apparatus for the extracorporeal reduction of the carbon dioxide content in blood via a fluid line, a first outlet for extracting a treated bloodstream from the blood treatment system, wherein the first outlet is in fluid communication with the outlet port at the first delimited region of the apparatus for the extracorporeal reduction of the carbon dioxide content in blood via a fluid line, a source for a buffer solution according to the features of at least one of the forms of use 1 to 6, wherein the source for a buffer solution is in fluid communication with the inlet port at the second delimited region of the apparatus for the extracorporeal reduction of the carbon dioxide content in blood via a fluid line, a container for collecting used buffer solution, wherein the container for collecting the used buffer solution is in fluid communication with the outlet port at the second delimited region of the apparatus for the extracorporeal reduction of the carbon dioxide content in blood via a fluid line, or a recirculation apparatus instead of the container for collecting used buffer solution, wherein the recirculation apparatus comprises a fluid line which returns the used buffer solution to the source of the buffer solution, characterized in that the treatment system comprises balancing devices by means of which the amount of buffer solution introduced from the source of buffer solution and the amount of used buffer solution can be balanced.

As previously defined, a "gas exchanger" in the context of the present disclosure is understood as an apparatus for the extracorporeal reduction of carbon dioxide content in blood in accordance with at least one of the embodiments 8 to 19.

In one embodiment, the treatment system according to the fourth aspect is characterized in that the balancing device is a gravimetric balancing device, in particular characterized in that the balancing device comprises a scale for weighing the amount of buffer solution used from buffer solution source as well as in that the balancing device comprises a scale for weighing the amount of the used buffer solution in the container for collecting the used buffer solution.

In a further embodiment, the treatment system according to the fourth aspect is characterized in that the balancing device is a volumetric balancing device which uses balance chambers to balance the volume of the buffer solution used from the buffer solution source and the volume of the used buffer solution or uses flow meters to balance the used volume of buffer solution taken from the buffer solution source and the amount of used buffer solution.

The inventive treatment system can be used with a dialysis machine as is used in acute dialysis. The inventive blood treatment system thereby offers the advantage of being able to be operated with a conventional dialysis machine. Such dialysis machines already have the protective systems required by the known standards for detecting air and blood loss in the extracorporeal blood circuit. The inventive treatment system and associated method for the extracorporeal reduction of carbon dioxide in a patient's blood can for example be used and operated in combination with the well-known "multiFiltratPRO" or "multiFiltrate" dialysis machines from the Fresenius Medical Care Deutschland GmbH company.

The inventive treatment system makes use of a gas exchanger which, as per the above-described definitions, exhibits the features of the apparatus for reducing the carbon dioxide content in blood as defined in embodiments 8 to 19. Such a gas exchanger comprises a gas-permeable membrane, in particular a gas-selective membrane. Such membranes are for example described in EP 277 801 A2 or DE 100 34 098 A1. A buffer solution is routed along the second delimited region of the gas exchanger. The patient's blood is pumped in counterflow in the first delimited region of the gas exchanger.

The inventive treatment system is largely unchanged from a treatment system for use in dialysis. The pumps used on the machine side can be operated to a therapeutically effective degree at a pumping rate ranging from 10 ml/min to 600 ml/min in order to conduct the buffer solution through the second delimited region of the apparatus for reducing carbon dioxide in the blood or the gas exchanger respectively. Used as the buffer solution is a buffer solution according to the first aspect of the invention, thus in particular a buffer solution having the features according to at least one of the forms of use 1 to 6.

In order to prevent the buffer solution from entering the patient's blood via the membrane of the gas exchanger, the fourth aspect of the present disclosure provides for balancing the buffer solution fed in and out of the gas exchanger. The buffer solution supplied to the gas exchanger corresponds to the buffer solution withdrawn from the source of buffer solution. The buffer solution discharged from the gas exchanger corresponds to the used buffer solution collected in the container for collecting used buffer solution. Known dialysis machines for acute dialysis have two scales which measure the dialysis fluid fed in and out of the dialyzer during dialysis therapy and accordingly regulate the pumps for the supply and discharge of the dialysis fluid.

The present treatment system has the advantage of being able to balance the volumes of buffer solution introduced and used in a gas exchanger during an extracorporeal blood treatment for reducing the carbon dioxide content in the blood of a patient by means of a buffer solution for $CO_2$. In particular, the buffer solutions used for the therapy is not to have any physiological components which are prohibited from entering into the patient's blood circulation as they can lead to situations which endanger the patient's health. In particular, a membrane defect can allow buffer solution to intrude into the extracorporeal blood circuit and end up in the patient's body. The balancing can determine a loss of buffer solution able to intrude into the extracorporeal blood circuit. This balancing can also ensue by means of balance chambers or by flow meters suitably arranged in the treatment system instead of scales. The inventive treatment system thus has a safety system with which it can be determined whether buffer solution has breached the patient's blood circuit. If the balancing device of the inventive treatment system accordingly determines that less used buffer solution is drained from the gas exchanger than is introduced into the gas exchanger, an alarm can be triggered by an electronic control unit of the inventive treatment system and further extracorporeal treatment e.g. stopped.

Figure 22:
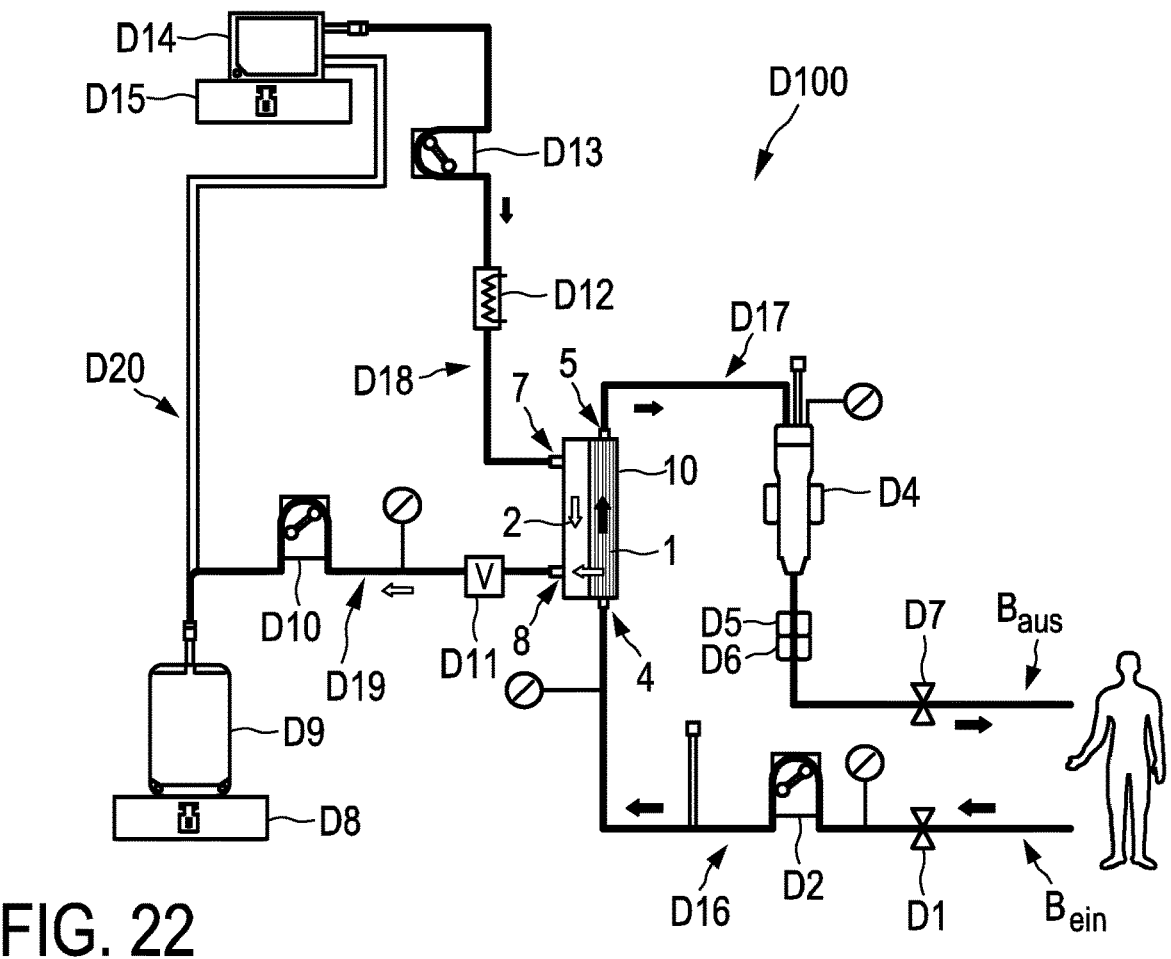
FIG. 22 is a schematic representation of an embodiment of the present invention, showing a treatment system for reducing carbon dioxide content in blood.

Further details and embodiments of the inventive treatment system will be explained referencing FIG. 22. The treatment system shown schematically in FIG. 22 is not to be understood as a definitive embodiment. Rather, it is clear to one skilled in the art that in the context of the present fourth aspect of the disclosure, further embodiments can be derived from the schematic illustration of FIG. 22 by adding or omitting individual features.

FIG. 22 shows an inventive treatment system (D100) for reducing the carbon dioxide content in blood in schematic representation. The depicted treatment system is composed of components that can be arranged on a dialysis machine and a treatment product. In certain embodiments, scales D8, D15, occlusion apparatus D1, D7, a blood leak detector D11, an optical detector D5, an air bubble detector D6, pumps D13, D10, D2 and a heating apparatus D12 are arranged on a dialysis machine. A gas exchanger, 10, drip chamber D4, container for buffer solution D9, source for buffer solution D14, and fluid lines D16 to D20 can be arranged on a treatment product. In accordance with the inventive treatment system, the components on the machine side and the components of the treatment product are designed to act together in the extracorporeal reduction of carbon dioxide in the blood of a patient.

In particular, pumps D2, D10 and D13 are designed to interact with fluid lines D16, D19 and D18 in order to effect the conveyance of blood from the patient $B_{in}$ into the treatment system and back to the patient $B_{out}$ as well as the conveyance of buffer solution from the source of buffer solution D14 to the gas exchanger 10 and from the gas exchanger 10 into the container D9 for collecting used buffer solution. In one embodiment, the fluid lines consist of flexible plastic tubes. Such fluid tubes are known in dialysis technology. They are characterized by being able to be squeezed together by the application of force so that no fluid can flow through the lumen of the flexible plastic tubes. Such tubes are further characterized in that they have a restoring force so that after an occlusion of the plastic tube, fluid can again flow through the lumen. The pumps can be designed as gear pumps, membrane pumps or peristaltic pumps. In one embodiment, pumps D2, D10 and D13 are designed as peristaltic pumps.

Furthermore, the heating apparatus D12 interacts with fluid line D18, which leads from the buffer solution source D14 to the gas exchanger 10, by warming the buffer solution flowing through the fluid line D18.

Furthermore, the scales D8, D15 for balancing the buffer solution interact with the source D14 of the buffer solution and the container for collecting used buffer solution in that the buffer solution in the buffer solution source D14 and the buffer solution in the container for collecting the buffer solution are weighed and can be balanced by means of an electronic control or processing unit in the dialysis machine (not shown in FIG. 22). In one embodiment, the buffer solution source D14 is a fluid bag containing the buffer solution. In a further embodiment, the container for collecting the used buffer solution is likewise a fluid bag. In the context of the present fourth aspect of the disclosure, the term "used buffer solution" denotes buffer solution which has passed through the second delimited region 2 of the gas exchanger for reducing carbon dioxide in the blood of a patient. In preferential embodiments in which the membrane 3 of the gas exchanger 10 is gas-permeable but fluid-tight, a volume store can in each case be arranged in fluid line D18 and/or fluid line D19 (not shown in FIG. 22). The volume store(s) serve to compensate for the difference in volume caused by potential process-related different feed rates of pumps D13 and D10. Provided membrane 3 of the gas exchanger 10 has no membrane defects during the therapeutic operation of the treatment system D100, the part of the treatment system through which the buffer solution flows is constant in volume.

Furthermore, the occlusion apparatus interact with the fluid lines D16 and D17 by preventing blood flow through the fluid lines by occluding said fluid lines. This is then particularly necessary when an electronic monitoring unit of the dialysis machine identifies an alarm during therapy to reduce the carbon dioxide content in the blood of a patient and the therapy needs to be ended or interrupted so as to not risk the patient's health. In one embodiment, the occlusion apparatus are mechanically operated or electromagnetically operated hose clamps on the machine which interact with fluid lines D16 and D17, designed as flexible plastic tubes, as being able to block or unblock them, particularly to the flow of blood.

Furthermore, the optical detector D5 and the air bubble detector D6 interact with fluid line D17. The interacting of the fluid line D17 with detectors D5 and D6 is orchestrated such that the detectors D5 and D6 can detect potential blood clots and air bubbles in the treated blood returned to the patient via outlet $B_{out}$. An electronic monitoring unit of the dialysis machine can evaluate the signals of the detectors D5 and D6 and trigger an alarm which e.g. activates occlusion apparatus D1 and D7 so as to be able to stop an administering of blood clots and/or air bubbles to the patient via outlet $B_{out}$.

Furthermore, the blood leak detector D11 interacts with fluid line D19. The interacting of the fluid line D19 with the blood leak detector is orchestrated such that the detector D1 can detect blood components in the buffer solution conducted from the gas exchanger 10 to the container D9 for collecting used buffer solution through fluid line D19. The detection of blood components in the buffer solution in fluid line D19 can be monitored and evaluated by an electronic monitoring unit of the dialysis machine so that the occlusion apparatus D1 and D7 can be activated if necessary and the therapy can be stopped. Blood components in fluid line D19 indicate a defective membrane in the gas exchanger D10 so that the dialysis machine can trigger an alarm via the blood leak detector D11 signal.

In one method for reducing carbon dioxide in the blood of a patient using a treatment system according to the invention, blood is drawn from the patient and introduced into the treatment system D100 via an inlet $B_{in}$. The blood drawn from the patient is conveyed via pump D1 which interacts with fluid line D16 to convey blood from the patient into the first delimited region of the gas exchanger. The blood flowing into the first delimited region 1 of the gas exchanger 10 via inlet port 4 flows along membrane 3 of the gas exchanger and is brought into gas exchange relationship with the buffer fluid flowing through the second delimited region 2 of the gas exchanger 10. The buffer solution, containing the buffer substances as described in the first aspect of the disclosure, compensates for carbon dioxide that diffuses across the membrane into the second delimited region. The blood reduced in carbon dioxide is discharged via the outlet port 5 at the first delimited region 1 of the gas exchanger 10 and flows into the drip chamber D4 via fluid line 17 in order to separate any potential air bubbles in the blood. The blood continues to flow through fluid line D17 to the outlet $B_{out}$ to the patient and is checked for blood clots and air bubbles via the optical detector D5 and the air bubble detector D6.

At the same time, in one method for reducing carbon dioxide in the blood of a patient using an inventive treatment system, buffer solution as described in the first aspect of the present disclosure flows through fluid line D18 from the source of buffer solution into the second delimited region 2 of the gas exchanger via pump D13, which interacts with fluid line D18. The carbon dioxide diffusing from the blood in the first delimited region 1 into the second delimited region 2 of the gas exchanger 10 via the membrane wall 3 of the gas exchanger 10 is compensated for by the buffer solution in the second delimited region and removed via outlet port 8. Pump D10 facilitates the discharging of used buffer solution from the second delimited region 2 of the gas exchanger 10 to the container D9 or to the recirculation apparatus. The used buffer solution is checked for blood components by the blood leak detector and evaluated by an electronic monitoring unit of the dialysis machine.

In an alternative embodiment, the used buffer solution can be recirculated. Meaning that, provided the buffer capacity for carbon dioxide has not yet been reached, the buffer solution can be returned to source D14. If the used buffer fluid has been recirculated to source D14, the buffer solution can be reused. A further pump which conveys the buffer solution back to the buffer solution source D14 can be arranged in fluid line D20 to that end (not shown in FIG. 22). The reducing of $CO_2$ in the patient's blood can be regulated by correspondingly regulating the supply and discharge pumps D13, D10 and the pump in fluid line D20 (not shown in FIG. 21).

The inventive treatment system D100 comprises a balancing device. In accordance with FIG. 22, the scales D8 and D15 are part of the balancing device. During the method of reducing carbon dioxide in the blood of a patient using a treatment system according to the invention, the amount of buffer solution taken from source 14 and the amount of buffer solution collected in container D9 are weighed. The amounts of buffer solution measured by the scales D8 and D15 are compared. The results of the weighings are evaluated by an electronic monitoring unit of the dialysis machine. If the results of the weighings determine that a lesser amount of buffer solution within a specific tolerance range is collected in container D9 in a predetermined sequence of successive weighings than is withdrawn from source D14, an alarm can be triggered via the dialysis machine. It can in this way be checked whether buffer solution is entering the blood circuit while the patient is being treated.

pH sensors can be fixed to fluid line D18 ahead of the inlet port 7 of the gas exchanger 10 in the buffer solution's direction of flow and in fluid line D19 after the outlet port 8 of the gas exchanger 10 in the buffer solution's direction of flow, by means of which the pH values of the buffer solution flowing to the gas exchanger and the buffer solution flowing from the gas exchanger are determined (not shown in FIG. 22). These pH sensors serve in monitoring and can be used to regulate the flow rate of the buffer solution. In particular, the progress of reducing the carbon dioxide in the blood of a patient can be tracked and monitored by measuring the pH and the change in the buffer solution's pH over the treatment period. Furthermore able to be monitored is whether the buffer solution provided in the source D14 still has sufficient buffer capacity to effect a therapeutically effective reduction of the carbon dioxide content in the patient's blood. Such monitoring of the buffer solution's pH value can be particularly relevant in the previously described recirculation of the buffer solution. For exact pH measuring, a temperature sensor which measures the temperature of the buffer solution in the area of the pH measurement can be further provided. The measured temperature as well as the measured pH values can be processed by an electronic monitoring or evaluating unit of the dialysis machine in order to predetermine the further course of the treatment.

Furthermore, pH sensors can be arranged in fluid line D16 ahead of the inlet port 4 of the gas exchanger 10 in the blood's direction of flow and in fluid line D17 after the outlet port of the gas exchanger in the blood's direction of flow (not shown in FIG. 22). In addition, $pCO_2$ pressure sensors which serve to measure the $CO_2$ partial pressure can also be arranged there (not shown in FIG. 22). For exact pH measuring, a temperature sensor can be arranged in the area of the pH measurement. The measurement results of the pH sensors, the temperature sensor and the $pCO_2$ sensor can be processed by a monitoring or evaluating unit of the dialysis machine and thereby used to control the further course of the treatment.

FIG. 22 REFERENCE NUMERAL LIST

D1 occlusion apparatus for blocking/enabling a bloodstream to the gas exchanger 10 through fluid line D16

D2 pump for conveying blood to the gas exchanger through fluid line D16

10 gas exchanger for reducing the carbon dioxide content in the blood of the patient D4 drip chamber for the separation of air bubbles in the blood in fluid line D17 for returning treated blood to the patient D5 optical detector for the detection of blood clots in the blood in fluid line D17 for returning treated blood to the patient D6 air bubble detector for the detection of air bubbles in the blood in fluid line D17 for returning treated blood to the patient D7 occlusion apparatus for blocking/enabling a bloodstream through fluid lines D17 for returning treated blood to the patient D8 scale for weighing the volume of used buffer solution in container D9 for collecting used buffer solution D9 container for collecting used buffer solution D10 pump for conveying buffer solution through fluid line D19 from the gas exchanger into the container D9 for collecting buffer solution D11 blood leak detector for the detection of membrane defects in the gas exchanger 10

D12 heating apparatus for warming the buffer solution in fluid line D18 prior to the buffer solution entering the gas exchanger D13 pump for conveying buffer solution into the gas exchanger D14 source for buffer solution D15 scale for determining the volume taken from source D14 for buffer solution D16 fluid line for conveying blood from a patient to the first delimited region 1 of the gas exchanger 10 via a blood inlet $B_{in}$ D17 fluid line for conveying blood from the first delimited region 1 of the gas exchanger 10 to the patient via outlet $B_{out}$ D18 fluid line for conveying buffer solution from a source 14 for buffer solution into the second delimited region of the gas exchanger 10

D19 fluid line for conveying used buffer solution from the second delimited region of the gas exchanger into the container for collecting used fluid, or for conveying used buffer solution into a recirculation apparatus for returning used buffer solution to the source of the buffer solution D20 fluid line for conveying used buffer solution from a recirculation apparatus for returning used buffer solution to the source of the buffer solution D100 treatment system for reducing the carbon dioxide content of blood in an extracorporeal blood circuit In a fifth aspect, the present invention relates to a inventive treatment system for reducing the carbon dioxide content in blood in an extracorporeal blood circuit, comprising an apparatus for the extracorporeal reduction of the carbon dioxide content in blood comprising a first delimited region (1) for receiving extracorporeal blood and a second delimited region (2) for receiving a buffer solution, wherein the first (1) and second region (2) adjoining each other in a contact zone are only separated by a membrane (3), via which gas exchange can occur between the blood and the buffer solution, and wherein the buffer solution is an aqueous solution in gas exchange with the blood of the patient conducted in an extracorporeal circuit and contains a buffer A and a buffer B, wherein buffer A consists of at least one buffer substance having a pK value of 7.9±0.2 at 37° C., and buffer B consists of at least one buffer substance having a pK value of 6.9±0.2 at 37° C., and wherein the solution has a post-titration pH value in the range of 8.25 to 8.35 at a carbon dioxide partial pressure of $pCO_2$=0.2 mmHg±0.2, a first inlet for introducing a bloodstream to be treated into the treatment system (E100), wherein the first inlet is in fluid communication with the first inlet port at the first delimited region of the apparatus for the extracorporeal reduction of the carbon dioxide content in blood via a fluid line, a first outlet for extracting a treated bloodstream from the treatment system, wherein the first outlet is in fluid communication with the outlet port at the first delimited region of the apparatus for the extracorporeal reduction of the carbon dioxide content in blood via a fluid line, a source for a buffer solution for reducing the carbon dioxide content in blood, wherein the source is in fluid communication with the inlet port at the second delimited region of the apparatus for the extracorporeal reduction of the carbon dioxide content in blood via a fluid line, a container for collecting used buffer solution, wherein the container for collecting used buffer solution is in fluid communication with the outlet port at the second delimited region of the apparatus for the extracorporeal reduction of the carbon dioxide content in the blood via a fluid line (E19), or characterized in that a means for reducing the pressure in the fluid line in fluid communication with the inlet port at the second delimited region of the apparatus for the extracorporeal reduction of the carbon dioxide content in blood is arranged in the fluid line in fluid communication with the inlet port at the second delimited region of the apparatus for the extracorporeal reduction of the carbon dioxide content in blood ahead of the inlet port.

As has already been previously defined, in the context of the present disclosure, a "gas exchanger" is understood as an apparatus for the extracorporeal reduction of the carbon dioxide content in blood in accordance with at least one of the embodiments 8 to 19.

When operating a treatment apparatus for reducing the $CO_2$ content in blood of the type described above, a buffer solution is routed along the gas-permeable membrane of the gas exchanger and brought into gas exchange relationship with the blood to be treated via the membrane. A higher pressure prevails within the gas exchanger in the first delimited region through which blood flows during the therapeutic treatment than in the second delimited region through which the buffer solution flows. The direction of flow of the buffer solution and of the blood are thereby preferably opposite. Conceivable buffer solutions for reducing the carbon dioxide content in blood are buffer solutions able to bind $CO_2$, also including those having a non-physiological composition. Safety precautions must therefore be taken to prevent the non-physiological buffer solution from entering into the blood circuit via the membrane wall of the gas exchanger. Particularly should membrane defects occur, there is the risk that the buffer solution will pass over to the blood side of the extracorporeal blood circuit and be infused into the patient.

For reasons of safety and medical therapy, it is therefore advantageous for a higher pressure to prevail in the fluid lines of the treatment system conducting the blood than in the fluid lines conducting the buffer solution. In the event of a defective membrane, for example a rupture in a fiber of a hollow fiber membrane when a hollow fiber membrane filter is used as the gas exchanger, there is most notably a leakage of blood from the first delimited region into the second delimited region of the gas exchanger. The infiltrating blood can then be detected by means of a blood leak detector in the fluid line in fluid communication with the outlet port at the second delimited region of the gas exchanger for the extracorporeal reduction of the carbon dioxide content in the blood. In addition, a higher gas exchange rate is effected by means of a higher pressure in the fluid lines conducting the blood compared to the fluid lines conducting the buffer solution and thus an improved reduction of the carbon dioxide content in the blood.

In order to prevent the buffer solution from entering the patient's blood via the membrane of the gas exchanger, the present fifth aspect proposes reducing the pressure in the fluid lines through which the buffer solution flows in order to effect a higher pressure in the fluid lines through which the blood flows. The pressure in the fluid lines through which the buffer solution flows is effected by a means for reducing the pressure arranged in the fluid line in fluid communication with the inlet port at the second delimited region of the gas exchanger.

The means for reducing the pressure can be a throttling element, e.g. a non-return valve.

The present treatment system according to the fifth aspect of the present disclosure has the advantage of no non-physiological buffer solution being able to intrude into the blood circuit and into the patient's body due to the arrangement of the means for reducing pressure during an extracorporeal blood treatment for reducing the carbon dioxide content in the blood of a patient by means of a buffer solution. In addition, the pressure difference between the first delimited region and the second delimited region of the gas exchanger is increased and thus the $CO_2$ gas exchange rate increased.

Further details and embodiments of the inventive treatment system will be explained referencing FIG. 23. The treatment system shown schematically in FIG. 22 is not to be understood as a definitive embodiment. Further embodiments can be derived from FIG. 23 by adding or omitting individual features in the context of the present fifth aspect of the present disclosure.

Figure 23:
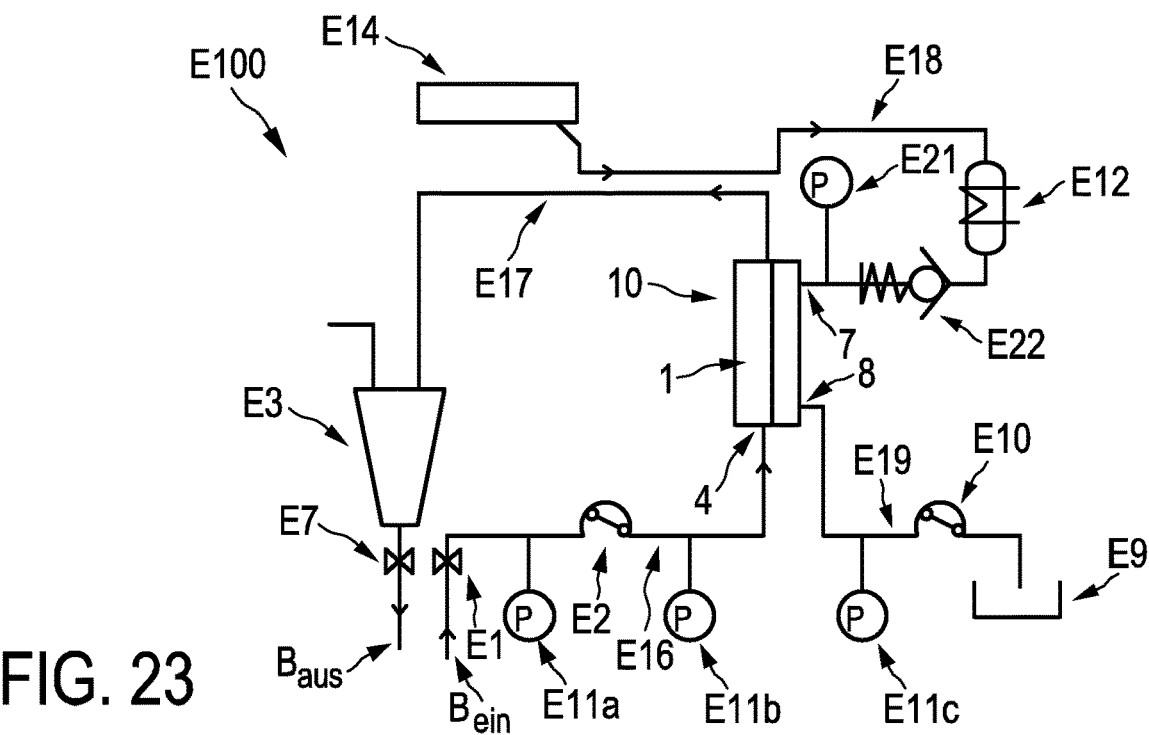
FIG. 23 is a schematic representation of a further embodiment of the present invention, showing a treatment system for reducing carbon dioxide content in blood.

FIG. 23 shows an inventive treatment system (E100) for reducing the carbon dioxide content in blood in schematic representation. The depicted treatment system consists of interacting machine-side components and components of a treatment product. The occlusion apparatus E1, E7, pressure sensors E11$a$, E11$b$, E11$c$ and E21, pumps E2 and E10, and heating apparatus E12 components can thereby be arranged on a dialysis machine. The gas exchanger 10, drip chamber E3, container for collecting buffer solution E9, source for buffer solution E14, fluid lines E16 to E19, and pressure reducing means E22 components can be arranged on a treatment product. According to the inventive treatment system, the components of the machine and the components of the treatment system are designed to interact functionally in the extracorporeal reduction of carbon dioxide in the blood of a patient.

In particular, pumps E2 and E10 are designed to interact with fluid lines E16 and E18 in order to effect the conveying of blood from the patient $B_{in}$ into the treatment system and back to the patient $B_{out}$ as well as the conveying of buffer solution from the source of the buffer solution E14 to the gas exchanger 10 and from the gas exchanger 10 into the container E9 for collecting used buffer solution. In one embodiment, the fluid lines consist of flexible plastic tubes. Such fluid tubes are known in dialysis technology. They are characterized by being able to be squeezed together by the application of force so that no fluid can flow through the lumen of a flexible plastic tube. Such tubes are further characterized in that they have a restoring force so that the lumen of a plastic tube opens after occlusion and fluid can flow through the lumen. When flexible plastic tubes are used, the pumps can be designed as peristaltic pumps. Alternatively, gear pumps or membrane pumps can also be used. In one embodiment, pumps E2 and D10 are designed as peristaltic pumps.

Furthermore, the heating apparatus E12 interacts with the fluid line E18 by warming the buffer solution guided from the source of the buffer solution D14 to the gas exchanger 10 flowing through fluid line D18. The heating apparatus can comprise machine-side thermal elements which serve as a source of thermal energy. Furthermore, the treatment product can comprise a flexible bag section in the region of the heating apparatus so that the thermal energy provided by the machine can act on the buffer solution over a larger surface section.

Furthermore, the occlusion apparatus interact with fluid lines E16 and E17 by preventing blood flow through fluid lines E16 and E17 by occluding said fluid lines. This is then particularly necessary when an electronic monitoring unit of the dialysis machine identifies an alarm during therapy to reduce the carbon dioxide content in the blood of a patient and the therapy needs to be ended or interrupted so as to not endanger the patient. In one embodiment, the occlusion apparatus are mechanically operated or electromagnetically operated hose clamps on the machine side which interact with fluid lines E16 and E17, which can be designed as flexible plastic tubes, as being able to block or unblock them, particularly to the flow of blood.

Furthermore, an optical detector and an air bubble detector (not shown in FIG. 23) can interact with fluid line E17. The interacting of the fluid line E17 with said detectors is orchestrated such that the detectors can detect potential blood clots and air bubbles in the treated blood returned to the patient via outlet $B_{out}$. An electronic monitoring unit of the dialysis machine can evaluate the signals of the cited detectors and trigger an alarm which e.g. activates occlusion apparatus E1 and E7 so as to be able to stop an administering of blood clots and/or air bubbles to the patient via outlet $B_{out}$.

Furthermore, a blood leak detector (not shown in FIG. 23) can interact with fluid line E19. The interacting of the fluid line E19 with the blood leak detector is orchestrated such that the blood leak detector can detect blood components in the buffer solution conducted from the gas exchanger 10 to the container E9 for collecting used buffer solution through fluid line E19. The detection of blood components in the buffer solution in fluid line D19 can be monitored and evaluated by an electronic monitoring unit of the dialysis machine so that the occlusion apparatus E1 and E7 can be activated if necessary and the therapy can be stopped. Blood components in fluid line E19 indicate a defective membrane in the gas exchanger 10 so that the dialysis machine can trigger an alarm via the blood leak detector signal.

In one method for reducing carbon dioxide in the blood of a patient using an inventive treatment system according to the present fifth aspect, blood is drawn from the patient and introduced into the treatment system E100 via an inlet $B_{in}$. The blood drawn from the patient is conveyed via pump E2 which interacts with fluid line E16 to convey blood from the patient into the first delimited region of the gas exchanger 10. The blood flowing into the first delimited region 1 of the gas exchanger 10 via inlet port 4 flows along membrane 3 of the gas exchanger and is brought into gas exchange relationship with the buffer fluid flowing through the second delimited region 2 of the gas exchanger 10. The buffer solution, containing the buffer substances as described in the first aspect of the present disclosure, compensates for carbon dioxide that diffuses across the membrane into the second delimited region. The blood reduced in carbon dioxide is discharged via the outlet port 5 at the first delimited region 1 of the gas exchanger 10 and flows into the drip chamber E4 via fluid line E17 in order to separate any potential air bubbles in the blood. The blood continues to flow through fluid line E17 to the outlet $B_{out}$ to the patient and is checked for blood clots and air bubbles when necessary via an optical detector and/or the air bubble detector D6.

At the same time, in one method for reducing carbon dioxide in the blood of a patient using an inventive treatment system, buffer solution as described for example in the first aspect of the present disclosure flows through fluid line E18 from the source of buffer solution into the second delimited region 2 of the gas exchanger via pump E13, which interacts with fluid line E19. The pressure of the buffer solution in fluid line E18 is reduced as it passes through the means for reducing the pressure so that there is a lower fluid pressure in the second delimited region 2 of the gas exchanger 10 than in the first delimited region of the gas exchanger through which blood flows. In one embodiment, the pressure reducing means is a non-return valve. The pressure in fluid line E18 is reduced in the direction of the buffer solution's direction of flow to the gas exchanger by the opening pressure of the non-return valve. In an alternative embodiment, the means for reducing the pressure can also be designed as a peristaltic pump which interacts with fluid line E18.

Furthermore, a pressure sensor E21 which interacts with fluid line E21 can be arranged between the means for pressure reduction E22 and the inlet port 7 at the second delimited region of the gas exchanger 10. The measured values recorded at said pressure sensor E21 can be evaluated via an electronic monitoring and control unit of the dialysis machine. The dialysis machine can, for example, regulate the pump output of pumps E2 or E10 based on the measured pressure values of sensor E21. The pressure monitoring can be helpful in comparing and setting the pressure determined at the pressure sensor E21 to the pressure of blood in one of the regions of fluid line E16, E17 or in the first delimited region 1 of the gas exchanger 10 such that the pressure in the fluid lines E16 and E17 and in the first delimited region 1 of the gas exchanger is higher than the pressure measured at the pressure sensor E21.

In particular, further pressure sensors E11a, E11b and E11c can be arranged in the inventive treatment device in order to monitor and regulate the required pressures in the treatment apparatus E100. In one embodiment, a pressure sensor E11 is arranged on fluid line E16 between the pump E2 and the occlusion apparatus E1 in order to measure the blood pressure in the inlet area of the treatment apparatus. In a further embodiment, a pressure sensor E11b is arranged between the gas exchanger 10 and the pump E2 in order to measure the blood pressure in the fluid line E16 ahead of the gas exchanger. In a further embodiment, a pressure sensor E11c is arranged on fluid line E19 between the pump E9 and the gas exchanger.

The carbon dioxide diffusing from the blood in the first delimited region 1 into the second delimited region 2 of the gas exchanger 10 via the membrane wall 3 of the gas exchanger 10 is compensated for by the buffer solution in the second delimited region and removed via outlet port 8. Used buffer solution is thereby drained from the second delimited region 2 of the gas exchanger 10 to the container E9 via pump E10. The used buffer solution is checked for blood components by the blood leak detector and evaluated by an electronic monitoring unit of the dialysis machine.

According to one embodiment of the fourth aspect of the present disclosure, the inventive treatment system E100 can comprise a balancing device. The amount of buffer solution taken from the source E14 and the amount of buffer solution collected in the container E9 can accordingly be determined and balanced by weighing or by flow sensors.

pH sensors can be fixed to fluid line E18 ahead of the inlet port 7 of the gas exchanger 10 in the buffer solution's direction of flow and in fluid line D19 after the outlet port 8 of the gas exchanger 10 in the buffer solution's direction of flow (not shown in FIG. 23), by means of which the pH values of the buffer solution flowing to the gas exchanger and the buffer solution flowing from the gas exchanger are determined (not shown in FIG. 22). These pH sensors serve in monitoring and can be used to regulate the flow rate of the buffer solution. In particular, the progress of reducing the carbon dioxide in the blood of a patient can be tracked and monitored by measuring the pH and the change in the buffer solution's pH over the treatment period. Furthermore able to be monitored is whether the buffer solution provided in the source D14 still has sufficient buffer capacity to effect a therapeutically effective reduction of the carbon dioxide content in the patient's blood. For exact pH measuring, a temperature sensor which measures the temperature of the buffer solution in the area of the pH measurement can be further provided. The measured temperature as well as the measured pH values can be processed by an electronic monitoring or evaluating unit of the dialysis machine in order to predetermine the further course of the treatment.

Furthermore, pH sensors can be arranged in fluid line E16 ahead of the inlet port 4 of the gas exchanger 10 in the blood's direction of flow and in fluid line D17 after the outlet port of the gas exchanger in the blood's direction of flow (not shown in FIG. 23). In addition, $pCO_2$ pressure sensors can also be arranged there to measure the $CO_2$ partial pressure (not shown in FIG. 23). For exact pH measuring, a temperature sensor can be arranged in the area of the pH measurement. The measurement results of the pH sensors, the temperature sensor and the $pCO_2$ sensor can be processed by a monitoring/evaluating unit of the dialysis machine and thereby used to control the further course of the treatment.

Lowering the height h of the buffer solution source E14 relative to the gas exchanger can effect a lowering of the buffer solution's pressure level in fluid line E18. Ideally, the buffer solution source E14 is thereby situated below the gas exchanger (not shown in FIG. 23).

FIG. 23 REFERENCE NUMERAL LIST

E1 occlusion apparatus for blocking/enabling a bloodstream to the gas exchanger 10 through fluid line E16
E2 pump for conveying blood to the gas exchanger through fluid line E16
10 gas exchanger for reducing the carbon dioxide content in the blood of the patient
E3 drip chamber for the separation of air bubbles in the blood in fluid line E17 for returning treated blood to the patient
E7 occlusion apparatus for blocking/enabling a bloodstream through fluid lines E17 for returning treated blood to the patient
E9 container for collecting used buffer solution
E10 pump for conveying buffer solution through fluid line E19 from the gas exchanger into the container E9 for collecting buffer solution E
E12 heating apparatus for warming the buffer solution in fluid line D18 prior to the buffer solution entering the gas exchanger 10
E14 source for buffer solution
E16 fluid line for conveying blood from a patient to the first delimited region 1 of the gas exchanger 10 via a blood inlet $B_{in}$
E17 fluid line for conveying blood from the first delimited region of the gas exchanger 10 to the patient via outlet $B_{out}$
E18 fluid line for conveying buffer solution from a source 14 for buffer solution into the second delimited region 2 of the gas exchanger 10
E19 fluid line for conveying used buffer solution from the second delimited region 2 of the gas exchanger 10 into the container for collecting used fluid, or for conveying used buffer solution into a recirculation apparatus for returning used buffer solution to the source 14 of the buffer solution
E11a pressure sensor for measuring the pressure in fluid line E16 after the blood inlet $B_{in}$ and ahead of pump E2 for conveying blood in fluid line E16
E11b pressure sensor for measuring the pressure in fluid line E16 ahead of inlet port 4 of the gas exchanger 10 in the first delimited region 1 of the gas exchanger and after pump E2 for conveying blood in fluid line E16
E11c pressure sensor for measuring the pressure in fluid line E19 between the inlet port 8 of the second delimited region of the gas exchanger 10 and pump E10 for conveying buffer solution in fluid line E19
E21 pressure sensor for measuring the pressure in fluid line E18 between the inlet port 7 at the second delimited region of the gas exchanger and the means for reducing the pressure E22 in fluid line E18
E22 means for reducing the pressure in fluid line E18
E100 treatment system for reducing the carbon dioxide content of blood in an extracorporeal blood circuit In a fourth and fifth aspect, the subject of the present invention is characterized by the features of the following embodiments 51 to 58:

Embodiment 51

A treatment system (D100) for the reduction of the carbon dioxide content in blood in an extracorporeal blood circuit, comprising
an apparatus for the extracorporeal reduction of the carbon dioxide content in blood (10) as described herein,
a first inlet ($B_{in}$) for introducing a bloodstream to be treated into the treatment system (D100), wherein the first inlet is in fluid communication with the first inlet port (4) at the first delimited region (1) of the apparatus for the extracorporeal reduction of the carbon dioxide content in blood (10) via a fluid line (D16),
a first outlet ($B_{out}$) for extracting a treated bloodstream from the treatment system (D100), wherein the first outlet is in fluid communication with the outlet port (5) at the first delimited region (1) of the apparatus for the extracorporeal reduction of the carbon dioxide content in blood (10) via a fluid line (D17), a source for a buffer solution (D14) for reducing the carbon dioxide content in blood, wherein the source (D14) is in fluid communication with the inlet port (7) at the second delimited region (2) of the apparatus for the extracorporeal reduction of the carbon dioxide content in blood (10) via a fluid line (D18), a container (D9) for collecting used buffer solution, wherein the container for collecting the used buffer solution (D9) is in fluid communication with the outlet port (8) at the second delimited region (2) of the apparatus for the extracorporeal reduction of the carbon dioxide content in blood (10) via a fluid line (D19), or a recirculation apparatus instead of the container for collecting used buffer solution, wherein the recirculation apparatus comprises a fluid line (D20) which returns the used buffer solution to the source of the buffer solution, characterized in that the treatment system comprises a balancing device, by means of which the amount of buffer solution used from the source of buffer solution and the amount of used buffer solution can be balanced.

Embodiment 52

The treatment system as described herein, characterized in that the balancing device is a gravimetric balancing device, n particular characterized in that the balancing device comprises a scale (D15) for weighing the amount of buffer solution in the buffer solution source, as well as in that the balancing device comprises a scale (D8) for weighing the amount of the used buffer solution in the container for collecting the used buffer solution; or characterized in that the balancing device is a volumetric balancing device which uses balance chambers to balance the volume of the buffer solution used from the buffer solution source (D14) and the volume of the used buffer solution, or uses flow meters to balance the used volume of the buffer solution taken from the source for a buffer solution and the amount of used buffer solution.

Embodiment 53

A treatment system (E100) for the reduction of the carbon dioxide content in blood in an extracorporeal blood circuit, comprising an apparatus for the extracorporeal reduction of the carbon dioxide content in blood (10) as described herein, a first inlet ($B_{in}$) for introducing a bloodstream to be treated into the treatment system (E100), wherein the first inlet is in fluid communication with the first inlet port (4) at the first delimited region (1) of the apparatus for the extracorporeal reduction of the carbon dioxide content in blood (10) via a fluid line (E16), a first outlet ($B_{out}$) for extracting a treated bloodstream from the treatment system (E100), wherein the first outlet is in fluid communication with the outlet port (5) at the first delimited region (1) of the apparatus for the extracorporeal reduction of the carbon dioxide content in blood (10) via a fluid line (E17), a source for a buffer solution (E14) for reducing the carbon dioxide content in blood, wherein the source (D14) is in fluid communication with the inlet port (7) at the second delimited region (2) of the apparatus for the extracorporeal reduction of the carbon dioxide content in blood (10) via a fluid line (E18), a container (E9) for collecting used buffer solution, wherein the container for collecting the used buffer solution (E9) is in fluid communication with the outlet port (8) at the second delimited region (2) of the apparatus for the extracorporeal reduction of the carbon dioxide content in blood (10) via a fluid line (E19), or characterized in that a means for reducing the pressure (E22) in the fluid line (E18) in fluid communication with the inlet port (7) at the second delimited region (2) of the apparatus for the extracorporeal reduction of the carbon dioxide content in blood (10) is arranged on the fluid line (E18) in fluid communication with the inlet port (7) at the second delimited region (2) of the apparatus for the extracorporeal reduction of the carbon dioxide content in blood ahead of the inlet port (7).

Embodiment 54

The treatment apparatus as described herein, characterized in that the means for reducing the pressure (E22) is a valve which opens upon a predetermined pressure in the fluid line (E18), in particular characterized in that the means for reducing the pressure is a non-return valve.

Embodiment 55

The treatment apparatus as described herein, characterized in that a pressure sensor is arranged between the inlet port (7) and the means for reducing the pressure (E22) in the fluid line (E18) in fluid communication with the inlet port (7) at the second delimited region (2) of the apparatus for the extracorporeal reduction of the carbon dioxide content in blood (10).

Embodiment 56

The treatment system as described herein, characterized in that pH sensors are arranged ahead of the inlet port (7) on the fluid line (D18, E18) in fluid communication with the inlet port (7) at the second delimited region (2) of the apparatus for the extracorporeal reduction of the carbon dioxide content in blood (10) and after the outlet port (8) on the fluid line (D19, E19) in fluid communication with the outlet port (8) at the second delimited region of the apparatus for the extracorporeal reduction of the carbon dioxide content in blood (10).

Embodiment 57

The treatment system as described herein, characterized in that pH sensors are arranged ahead of the inlet port (4) on the fluid line (D16, E16) in fluid communication with the inlet port (4) at the first delimited region (I) of the apparatus for the extracorporeal reduction of the carbon dioxide content in blood (10) and after the outlet port (5) on the fluid line (D17, E17) in fluid communication with the outlet port (5) at the first delimited region (1) of the gas exchanger.

Embodiment 58

The treatment system as described herein, characterized in the buffer solution is designed for the reduction of the carbon dioxide content in blood as described herein.

The invention claimed is:

1. A treatment system for reduction of carbon dioxide content in blood, of a patient, in an extracorporeal blood circuit, comprising:

a source of buffer solution for reducing carbon dioxide content in blood;

an apparatus for extracorporeal reduction of carbon dioxide content in blood, comprising a first delimited region for receiving extracorporeal blood and a second delimited region for receiving buffer solution from the source of buffer solution;

a buffer inlet for introducing the source of buffer solution into the second delimited region, the buffer inlet being in fluid communication with a buffer inlet port at the second delimited region;

a buffer outlet for extracting used buffer from the apparatus for the extracorporeal reduction of carbon dioxide content in blood, the buffer outlet being in fluid communication with a buffer outlet port at the second delimited region, wherein the first delimited region and the second delimited region adjoin each other in a contact zone and are only separated by a membrane via which gas exchange occurs between the blood of the patient and the buffer solution, the buffer solution is an aqueous solution in gas exchange contact with the blood of the patient in an extracorporeal circuit, the buffer solution contains a buffer A and a buffer B, buffer A consists of at least one buffer substance having a pK value of 7.9±0.2 at 37° C., buffer B consists of at least one buffer substance having a pK value of 6.9±0.2 at 37° C., the buffer solution has a post-titration pH value in the range of 8.25 to 8.35 at a carbon dioxide partial pressure of pCO2=0.2 mmHg±0.2, and the source of buffer solution is in fluid communication with the buffer inlet port at the second delimited region, via a buffer inlet line;

a blood inlet for introducing a stream of the blood of the patient to be treated, into the treatment system, wherein the blood inlet is in fluid communication with a blood inlet port at the first delimited region, via a blood inlet line;

a blood outlet for extracting a treated bloodstream from the treatment system, wherein the blood outlet is in fluid communication with a blood outlet port at the first delimited region, via a blood outlet line;

a container for collecting used buffer solution, wherein the container for collecting the used buffer solution is in fluid communication with the buffer outlet port at the second delimited region, via a buffer outlet line;

an electronic monitoring and control unit;

a means for reducing the pressure in the buffer inlet line in fluid communication with the buffer inlet port at the second delimited region;

a first pressure sensor arranged between the buffer inlet port and the means for reducing the pressure in the buffer inlet line, the first pressure sensor being configured to record and send measured buffer inlet line pressure values to the electronic monitoring and control unit; and a second pressure sensor arranged along the blood inlet line ahead of the blood inlet port, the second pressure sensor being configured to record and send measured blood inlet line pressure values to the electronic monitoring and control unit, wherein the means for reducing the pressure in the fluid line comprises a throttling element, the means for reducing the pressure in the fluid line is arranged on the buffer inlet line, ahead of the buffer inlet port, so as to reduce the pressure in the buffer inlet line and in the buffer outlet line, and the electronic monitoring and control unit is configured to receive the measured buffer inlet line pressure values, to receive the measured blood inlet line pressure values, and to control a further course of treatment in order to effect a higher pressure in the blood inlet line than in the buffer inlet line and to effect a higher gas exchange rate and improved reduction of carbon dioxide content in the blood of the patient.

2. The treatment system according to claim 1, wherein the means for reducing the pressure is a valve that opens upon a predetermined pressure in the fluid line that is in fluid communication with the buffer inlet port.

3. The treatment system according to claim 1, wherein the membrane comprises at least one polymer selected from the group of polypropylene (PP), polymethylpentene (PMP), polysulfone (PSU), and optionally PVP, or a mixture from the group of aforementioned polymers.

4. The treatment system according to claim 1, wherein the membrane is formed from a plurality of hollow fibers.

5. The treatment system according to claim 1, wherein the membrane is coated with silicone.

6. The treatment system according to claim 4, wherein the inner surface and/or the outer surface of the hollow fibers are coated with silicone.

7. The treatment system according to claim 1, wherein the first delimited region for receiving the extracorporeal blood has the blood inlet port for extracorporeal blood and the blood outlet port for the extracorporeal blood, and is configured such that the extracorporeal blood can flow through the first delimited region from the blood inlet port to the blood outlet port in a first flow direction, and the second delimited region for receiving the buffer solution has the buffer inlet port and the buffer outlet port for the buffer solution and is configured such that the buffer solution can flow through the second delimited region from the buffer inlet port to the buffer outlet port in a second flow direction, and wherein the first flow direction and the second flow direction are oriented to run opposite to each other.

8. The treatment system according to claim 1, wherein an exchange surface via which gas exchange occurs through the membrane, in the contact zone, amounts to at least 0.3 $m^2$.

9. The treatment system according to claim 1, wherein an exchange surface via which gas exchange can occur through the membrane, in the contact zone, amounts to at most 5 $m^2$.

10. The treatment system according to claim 1, wherein pH sensors are arranged ahead of the buffer inlet port on the buffer inlet line in fluid communication with the buffer inlet port at the second delimited region, and after the buffer outlet port on the buffer outlet line in fluid communication with the buffer outlet port at the second delimited region.

11. The treatment system according to claim 1, wherein pH sensors are arranged ahead of the blood inlet port on the blood inlet line that is in fluid communication with the blood inlet port at the first delimited region, and after the blood outlet port on the blood outlet line that is in fluid communication with the blood outlet port at the first delimited region.

12. The treatment system according to claim 1, wherein the buffer solution is designed for the reduction of the carbon dioxide content in blood.

13. The treatment system according to claim 1, wherein the membrane is formed from silicone-coated hollow fibers.

14. The treatment system according to claim 1, wherein the means for reducing the pressure is a non-return valve.

15. The treatment system according to claim 1, wherein the membrane comprises a mixture of polysulfone and polyvinylpyrrolidone.

16. The treatment system according to claim 1, wherein an exchange surface via which gas exchange occurs through the membrane, in the contact zone, amounts to at least 2 m$^2$.

17. The treatment system according to claim 1, wherein an exchange surface via which gas exchange occurs through the membrane, in the contact zone, amounts to at most 3 m$^2$.

* * * * *